United States Patent
Tremblay et al.

(10) Patent No.: US 9,822,170 B2
(45) Date of Patent: Nov. 21, 2017

(54) CO-USE OF A CLUSTERIN INHIBITOR WITH AN EGFR INHIBITOR TO TREAT CANCER

(71) Applicant: ALETHIA BIOTHERAPEUTICS INC., Montreal (CA)

(72) Inventors: Gilles Bernard Tremblay, La Prairie (CA); Elisabeth Viau, Laval (CA); Mario Filion, Longueuil (CA)

(73) Assignee: Alethia Biotherapeutics Inc., Montreal (CA)

( * ) Notice: Subject to any disclaimer, the term of this patent is extended or adjusted under 35 U.S.C. 154(b) by 5 days.

(21) Appl. No.: 14/374,967

(22) PCT Filed: Feb. 22, 2013

(86) PCT No.: PCT/CA2013/000167
§ 371 (c)(1),
(2) Date: Jul. 28, 2014

(87) PCT Pub. No.: WO2013/123588
PCT Pub. Date: Aug. 29, 2013

(65) Prior Publication Data
US 2015/0044220 A1  Feb. 12, 2015

Related U.S. Application Data

(60) Provisional application No. 61/601,786, filed on Feb. 22, 2012.

(51) Int. Cl.
| | |
|---|---|
| *C07K 16/18* | (2006.01) |
| *A61K 31/5377* | (2006.01) |
| *A61K 39/395* | (2006.01) |
| *C07K 16/28* | (2006.01) |
| *A61K 45/06* | (2006.01) |
| *A61K 31/506* | (2006.01) |
| *A61K 31/517* | (2006.01) |
| *A61K 39/00* | (2006.01) |

(52) U.S. Cl.
CPC ............ *C07K 16/18* (2013.01); *A61K 31/506* (2013.01); *A61K 31/517* (2013.01); *A61K 31/5377* (2013.01); *A61K 39/3955* (2013.01); *A61K 45/06* (2013.01); *C07K 16/2863* (2013.01); *A61K 2039/505* (2013.01); *A61K 2039/507* (2013.01); *C07K 2317/21* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,595,756 A * | 1/1997 | Bally et al. ............ | 424/450 |
| 5,654,407 A | 8/1997 | Boyle et al. | |
| 6,342,221 B1 | 1/2002 | Thorpe et al. | |
| 6,383,808 B1 | 5/2002 | Monia et al. | |
| 6,464,975 B2 | 10/2002 | Millis | |
| 6,812,339 B1 | 11/2004 | Venter et al. | |
| 6,818,749 B1 | 11/2004 | Kashmiri et al. | |
| 6,900,187 B2 | 5/2005 | Gleave et al. | |
| 7,279,294 B2 | 10/2007 | Morin et al. | |
| 7,285,541 B2 | 10/2007 | Gleave et al. | |
| 7,309,487 B2 | 12/2007 | Inana et al. | |
| 7,537,931 B2 | 5/2009 | Adams et al. | |
| 7,569,551 B2 | 8/2009 | Gleave et al. | |
| 7,585,937 B2 | 9/2009 | Kungl | |
| 7,597,888 B2 | 10/2009 | Gill et al. | |
| 7,691,382 B2 | 4/2010 | Dobson | |
| 8,025,878 B2 | 9/2011 | Gellerfors et al. | |
| 8,044,179 B2 | 10/2011 | O'Connor-McCourt et al. | |
| 8,168,427 B2 | 5/2012 | Sahin et al. | |
| 8,426,562 B2 | 4/2013 | O'Connor-McCourt et al. | |
| 8,748,398 B2 | 6/2014 | Lee | |
| 8,802,826 B2 | 8/2014 | Tremblay et al. | |
| 2003/0118592 A1 | 6/2003 | Ledbetter et al. | |
| 2003/0133939 A1 | 7/2003 | Ledbetter et al. | |
| 2003/0134301 A1 | 7/2003 | Brooksbank et al. | |
| 2003/0162702 A1 | 8/2003 | Millis | |
| 2003/0211476 A1 | 11/2003 | O'Mahony et al. | |
| 2004/0082534 A1 | 4/2004 | Gleave et al. | |

(Continued)

FOREIGN PATENT DOCUMENTS

| | | |
|---|---|---|
| EP | 1603514 A2 | 12/2005 |
| EP | 1716227 A2 | 11/2006 |

(Continued)

OTHER PUBLICATIONS

Vajdos et al. (J Mol Biol. Jul. 5, 2002;320(2):415-28 at 416).*
Brown et al. (J Immunol. May 1996;156(9):3285-91.*
Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Aagaard et al (Advanced Drug Delivery Reviews 59 (2007) 75-86).*
Warzocha et al (Leukemia and Lymphoma, Val. 24. pp. 267-281).*
McKeague et al (J Nucleic Acids. 2012;2012:748913. Epub Oct. 24, 2012).*
Guido et al (Curr Med Chem. 2008;15(1):37-46).*
Clark et al (J. Med. Chem., 2014, 57 (12), pp. 5023-5038).*
Sporn et al, "Chemoprevention of Cancer," Carcinogenesis, vol. 21 (2000), 525-530.*
Auerbach et al (Cancer and Metastasis Reviews, 2000, 19: 167-172).*

(Continued)

*Primary Examiner* — Brian J Gangle
*Assistant Examiner* — Andrea McCollum
(74) *Attorney, Agent, or Firm* — Janique Forget

(57) ABSTRACT

Epidermal growth factor receptor (EGFR) expression and phosphorylation is increased in cancer cells treated with anti-clusterin antibodies. Such treatment is also accompanied with the reappearance of an epithelial phenotype of the cancer cell, as determined by an increased E-cadherin expression at the surface of cancer cells. Clusterin inhibitors may thus induce reversal of the epithelial to mesenchymal phenotype and restore sensitivity of cancer cells to EGFR inhibitors. Combinations of a clusterin inhibitor and an EGFR as well as their use in treatment of cancer are thus provided herewith.

17 Claims, 6 Drawing Sheets

(56) References Cited

U.S. PATENT DOCUMENTS

| | | |
|---|---|---|
| 2004/0220131 A1 | 11/2004 | Jackson et al. |
| 2004/0224914 A1 | 11/2004 | Jackson et al. |
| 2005/0048490 A1 | 3/2005 | Azimzai et al. |
| 2005/0152903 A1 | 7/2005 | Newman et al. |
| 2005/0208558 A1 | 9/2005 | Venter et al. |
| 2005/0222027 A1 | 10/2005 | Chiang et al. |
| 2005/0255114 A1 | 11/2005 | Labat et al. |
| 2006/0029956 A1 | 2/2006 | Beyer et al. |
| 2006/0088532 A1 | 4/2006 | Alitalo et al. |
| 2006/0122141 A1 | 6/2006 | Gleave |
| 2006/0251668 A1 | 11/2006 | Goletz et al. |
| 2006/0258852 A1 | 11/2006 | Lugovskoy et al. |
| 2007/0003547 A1 | 1/2007 | Foote |
| 2007/0015145 A1 | 1/2007 | Woolf et al. |
| 2007/0042945 A1 | 2/2007 | Bodary et al. |
| 2007/0071675 A1* | 3/2007 | Wu et al. ............ 424/1.49 |
| 2007/0082337 A1 | 4/2007 | Sorek et al. |
| 2007/0083334 A1 | 4/2007 | Mintz et al. |
| 2007/0099242 A1 | 5/2007 | Heinecke et al. |
| 2007/0105114 A1 | 5/2007 | Li et al. |
| 2007/0117746 A1 | 5/2007 | Dobson |
| 2007/0134260 A1 | 6/2007 | Feger et al. |
| 2007/0224201 A1 | 9/2007 | Wu et al. |
| 2008/0014198 A1 | 1/2008 | Gleave et al. |
| 2008/0064651 A1 | 3/2008 | Gleave et al. |
| 2008/0070995 A1 | 3/2008 | Westbrook et al. |
| 2008/0119425 A1 | 5/2008 | Gleave et al. |
| 2008/0253963 A1 | 10/2008 | Morin et al. |
| 2008/0261912 A1 | 10/2008 | Gleave et al. |
| 2008/0274996 A1 | 11/2008 | Gleave et al. |
| 2008/0286834 A1 | 11/2008 | Halenbeck et al. |
| 2008/0293070 A1 | 11/2008 | Sekaly et al. |
| 2008/0307537 A1 | 12/2008 | Bachoo |
| 2008/0317771 A1 | 12/2008 | Spagnoli et al. |
| 2009/0005541 A1 | 1/2009 | Kungl |
| 2009/0018026 A1 | 1/2009 | Kim et al. |
| 2009/0048171 A1 | 2/2009 | Dobson |
| 2009/0053828 A1 | 2/2009 | Regnier et al. |
| 2009/0081685 A1 | 3/2009 | Beyer et al. |
| 2009/0104215 A1* | 4/2009 | Ekiel ............ A61K 31/00 424/185.1 |
| 2009/0117578 A1 | 5/2009 | Metz et al. |
| 2009/0144839 A1 | 6/2009 | Inana et al. |
| 2009/0181380 A1 | 7/2009 | Belouchi et al. |
| 2009/0203639 A1 | 8/2009 | Van Criekinge et al. |
| 2009/0208921 A1 | 8/2009 | Tempst et al. |
| 2009/0215709 A1 | 8/2009 | Van Criekinge et al. |
| 2009/0238832 A1 | 9/2009 | Bodary-Winter et al. |
| 2009/0258089 A1 | 10/2009 | Gleave et al. |
| 2009/0280124 A1 | 11/2009 | Labat et al. |
| 2009/0292008 A1 | 11/2009 | Gleave et al. |
| 2010/0075866 A1 | 3/2010 | Hood et al. |
| 2010/0086541 A1 | 4/2010 | Wu et al. |
| 2011/0033471 A1 | 2/2011 | O'Connor-McCourt et al. |
| 2012/0071635 A1 | 3/2012 | O'Connor-McCourt et al. |
| 2015/0044220 A1 | 2/2015 | Tremblay et al. |
| 2015/0111250 A1 | 4/2015 | O'Connor-McCourt et al. |

FOREIGN PATENT DOCUMENTS

| | | |
|---|---|---|
| EP | 1940457 A2 | 7/2008 |
| EP | 2008100 A2 | 12/2008 |
| EP | 2014675 A1 | 1/2009 |
| EP | 2071336 A1 | 6/2009 |
| EP | 2087152 A1 | 8/2009 |
| WO | WO-91/05043 A1 | 4/1991 |
| WO | WO-00/34469 A1 | 6/2000 |
| WO | WO-01/66689 A2 | 9/2001 |
| WO | WO-02/22635 A1 | 3/2002 |
| WO | WO-02/072830 A2 | 9/2002 |
| WO | WO-03/016475 A2 | 2/2003 |
| WO | WO-03/054152 A2 | 7/2003 |
| WO | WO-03/080672 A1 | 10/2003 |
| WO | WO-2004/005934 A2 | 1/2004 |
| WO | WO-2004/050707 A2 | 6/2004 |
| WO | WO-2004066941 A2 | 8/2004 |
| WO | WO-2005/016962 A2 | 2/2005 |
| WO | WO-2005/049806 A2 | 6/2005 |
| WO | WO-2005/058959 A2 | 6/2005 |
| WO | WO-2005/060457 A2 | 7/2005 |
| WO | WO-2005/080434 A1 | 9/2005 |
| WO | WO-2006/010047 A2 | 1/2006 |
| WO | WO-2006/035237 A2 | 4/2006 |
| WO | WO-2006/037604 A1 | 4/2006 |
| WO | WO-2006/056054 A1 | 6/2006 |
| WO | WO-2006/081430 A2 | 8/2006 |
| WO | WO-2006/089586 A1 | 8/2006 |
| WO | WO-2006/113671 A2 | 10/2006 |
| WO | WO-2007/030930 A1 | 3/2007 |
| WO | WO-2007/047995 A2 | 4/2007 |
| WO | WO-2007/123976 A2 | 11/2007 |
| WO | WO-2008/021290 A2 | 2/2008 |
| WO | WO-2008/049239 A1 | 5/2008 |
| WO | WO-2008/085035 A1 | 7/2008 |
| WO | WO-2008/104808 A2 | 9/2008 |
| WO | WO-2009/034562 A2 | 3/2009 |
| WO | WO-2009/061382 A2 | 5/2009 |
| WO | WO-2009/090553 A2 | 7/2009 |
| WO | WO-2009/093246 A2 | 7/2009 |
| WO | WO-2009/116860 A1 | 9/2009 |
| WO | WO-2009/117030 A2 | 9/2009 |
| WO | WO2009/148252 | 12/2009 |
| WO | WO-2010/030980 A2 | 3/2010 |
| WO | WO-2010/118521 A1 | 10/2010 |
| WO | WO-2011/063523 A1 | 6/2011 |
| WO | WO-2013/123588 A1 | 8/2013 |

OTHER PUBLICATIONS

Gura T (Science, 1997, 278(5340): 1041-1042, encloses 1-5).*
Jain RK (Scientific American, Jul. 1994,58-65).*
Larue et al (Oncogene. Nov. 14, 2005;24(50):7443-54).*
Adamo, V. et al., Gefitinib in lung cancer therapy, Cancer Biology & Therapy, 8:206-212 (2009).
Akashi, Y. et al., Enhancement of the antitumor activity of ionising radiation by nimotuzumab, a humanised monoclonal antibody to the epidermal growth factor receptor, in non-small cell lung cancer cell lines of differing epidermal growth factor receptor status, British Journal of Cancer, 98(4):749-755 (2008).
Al Moustafa, A. et al., Black Cellular Spreading and Motility Assay, BioTechniques, 27(1):60-62 (1999).
Bailey, R. et al., Clusterin, a Binding Protein with a Molten Globule-like Region, Biochemistry,40:11828-11840 (2001).
Barr, S. et al., Bypassing cellular EGF receptor dependence through epithelial-to-mesenchymal-like transitions, Clinical and Experimental Medicine, 25:685-693 (2008).
Bendig, M.M. et al., Humanization of a Rodent Monoclonal Antibodies by CDR Grafting, Methods: A Companion to Methods in Enzymology, 8:83-93 (1995).
Bird, R.E. et al., Single-Chain Antigen-Binding Proteins, Science, 242(4877):423-426 (1988).
Bodey, B. et al., Failure of Cancer Vaccines: The Significant Limitations of this Approach to Immunotherapy, Anticancer Research, 20:2665-2676 (2000).
Brown, M. et al., Tolerance to single, but not multiple, amino acid replacements in antibody VH CDR 2: a means of minimizing B cell wastage from somatic hypermutation? J Immunol., 156(9):3285-3291 (1996).
Casset, F. et al., A peptide mimetic of an anti-CD4 monoclonal antibody by rational design, Biochemical and Biophysical Research Communications, 307:198-205 (2003).
Cervellera, M. et al. Direct Transactivation of the Anti-apoptotic Gene Apolipoprotein J (Clusterin) by B-MYB, The Journal of Biological Chemistry, 275(28):21055-21060 (2000).
Chatterjee, M.B. et al., Idiotypic antibody immunotherapy of cancer, Cancer Immunology and Immunotherapy, 38:75-82 (1994).
Chen, Y. et al., Selection and Analysis of an Optimized Anti-VEGF Antibody: Crystal Structure of an Affinity-matured Fab in Complex with Antigen, The Journal of Molecular Biology, 293:865-881 (1999).

(56) References Cited

OTHER PUBLICATIONS

Chi, K.N. et al., A Phase I Pharmacokinetic and Pharmacodynamic Study of OGX-011, a 2'-Methoxyethyl Antisense Oligonucelotide to Clusterin, in Patients With Localized Prostate Cancer, Journal of the National Cancer Institute, 97(17):1287-1296 (2005).
Chou, T-Y. et al., Clusterin silencing in human lung adenocarcinoma cells induces a mesenchymal-to-epithelial transition through modulating the ERK/Slug pathway, Cellular Signaling, 21(5):704-711 (2009).
Chung, J. et al. Enhanced chemosensitivity of bladder cancer cells to cisplatin by suppression of clusterin in vitro, Cancer Letters, 203:155-161 (2004).
Clackson, T. et al., Making antibody fragments using phage display libraries, Nature, 352:624-628 (1991).
Colman, P.M., Effects of amino acid sequence changes on antibody-antigen interactions, Research in Immunology, 145:33-36 (1994).
Costanzo, R. et al., Gefitnib in non small cell lung cancer, Journal of Biomedicine and Biotechnology, 2011:815269 (2011).
Dall'Acqua W.F. et al., Antibody humanization by framework shuffling, Methods, 36:43-60 (2005).
De Gruijl, T.D. et al., Cancer vaccine strategies get bigger and better, Nature Medicine, 5:1124-1125 (1999).
De Pascalis, R. et al., Grafting of "Abbreviated" Complementarity-Determining Regions Containing Specificity-Determining Residues Essential for Ligand Contact to Engineer a Less Immunogenic Humanized Monoclonal Antibody, The Journal of Immunology, 169:3076-3084 (2002).
Deng, H.B. et al., Increased Expression of Dihydrodiol Dehydrogenase Induces Resistance to Cisplatin in Human Ovarian Carcinoma Cells, The Journal of Biological Chemistry, 277(17):15035-15043 (2002).
Donnelly, J., Cancer vaccine targets leukemia, Nature Medicine, 11(9):1354-1356 (2003).
Dunker, A.K. et al., Intrinsically disordered protein, Journal of Molecular Graphics and Modelling, 19(1):26-59, (2001).
Durocher, Y. et al., High-level and high-throughput recombinant protein production by transient transfection of suspension-growing human 293-EBNA1 cells, Nucleic Acids Research, 30(2):1-9 (2002).
EMBL Accession No. AF139227.1, Mus musculus anti-fluorescein immunoglobulin light chain mRNA partial cds, first referenced 1999.
EMBL Accession No. AJ965435.1, Synthetic construct for anti-von Willebrand factor A3-domain scFV antibody, first referenced 2005.
Enjalbert, B. et al., Stress-induced Gene Expression in *Candida albicans*: Absence of a General Stress Response; Molecular Biology of the Cell, 14:1460-1467 (2003).
ENSEMBL Protein ID: ENSCAFP00000012350, Jun. 8, 2010.
ENSEMBL Protein ID:ENSCAFP00000034804 Jun. 8, 2010.
ENSEMBL Protein ID:ENSECAP00000005450 Jun. 8, 2010.
ENSEMBL Protein ID:ENSEEUP00000006956 Jun. 8, 2010.
ENSEMBL Protein ID:ENSFCAP00000013377 Jun. 8, 2010.
ENSEMBL Protein ID:ENSMICP00000007021 Jun. 8, 2010.
ENSEMBL Protein ID:ENSMLUP00000006142 Jun. 8, 2010.
ENSEMBL Protein ID:ENSMMUP00000032168 Jun. 8, 2010.
ENSEMBL Protein ID:ENSMMUP00000032169 Jun. 8, 2010.
ENSEMBL Protein ID:ENSMMUP0000028339 Jun. 8, 2010.
ENSEMBL Protein ID:ENSMMUP0000032167 Jun. 8, 2010.
ENSEMBL Protein ID:ENSMMUP0000032170 Jun. 8, 2010.
ENSEMBL Protein ID:ENSMUSP00000022616 Jun. 8, 2010.
ENSEMBL Protein ID:ENSOCUP00000005178 Jun. 8, 2010.
ENSEMBL Protein ID:ENSOPRP00000000527 Jun. 8, 2010.
ENSEMBL Protein ID:ENSPPYP00000020696 Jun. 8, 2010.
ENSEMBL Protein ID:ENSPTRP00000034422 Jun. 8, 2010.
ENSEMBL Protein ID:ENSPTRP00000056651 Jun. 8, 2010.
ENSEMBL Protein ID:ENSRNOP00000022095 Jun. 8, 2010.
Essabbani, A., et al. Identification of Clusterin Domain Involved in NF-κB Pathway Regulation, The Journal of Biological Chemistry, 285(7):4273-4277 (2010).
Ezzell, C., Cancer "Vaccines": An Idea Whose Time Has Come?, The Journal of NIH Research, 7:46-49 (1995).
Fassina, A. et al., Epithelial-mesenchymal transition in malignant mesothelioma, Modern Pathology, 25(1):86-99 (2012).
Forni, G. et al., Immunoprevention of Cancer: Is the Time Ripe?, Cancer Research, 60:2571-2575 (2000).
GenBank accession No. AAA30846, Hartmann, K. et al. J. Biol. Chem. 266 (15), pp. 9924-9931 (1991).
GenBank accession No. AAA31013, Diemer, V. J. Biol. Chem. 267 (8), pp. 5257-5264 (1992).
GenBank accession No. AAA35692, Jenne, D.E. and Tschopp, J. Journal Proc. Natl. Acad. Sci. U.S.A. 86 (18), pp. 7123-7127 (1989).
GenBank accession No. AAA37284, Hodgdon, B. A. et al. "Secretion of sulfated glycoprotein . . . " Apr. 27, 1993.
GenBank accession No. AAA37422, French, L.E. et al., J. Cell biol. 122 (5), pp. 1119-1130 (1993).
GenBank accession No. AAA41273, Collard, M. W. and Griswold, M. D. J. Biochemistry 26 (12), pp. 3297-3303 (1987).
GenBank accession No. AAA42298, Wong, P. et al. J. Biol. Chem. 268 (7), pp. 5021-5031 (1993).
GenBank accession No. AAA42299, Wong, P. et al. J. Biol. Chem. 268 (7), pp. 5021-5031 (1993).
GenBank accession No. AAA51765, de Silva, H.V. et al., J. Biochemistry 29 (22), pp. 5380-5389 (1990).
GenBank accession No. AAA60321, Danik, M. et al. J. Proc. Natl. Acad. Sci. U.S.A. 88 (19), pp. 8577-8581 (1991).
GenBank accession No. AAA60567, Glew, M.D. et al. Partial mucleotide sequence of the human SP40, 40 gene Jan. 13, 1995.
GenBank accession No. AAA80313, Barber, J. A. et al., "Nucleotide sequence of the complementary DNA . . . " Nov. 1, 1995.
GenBank accession No. AAB06507, Wong P. et al. Eu. J. Biochem. 221 (3), 917-925 (1994).
GenBank accession No. AAB06508, Wong, P. et al. Eur. J. Biochem. 221 (3) pp. 917-925 (1994).
GenBank accession No. AAB25217, Choi-Miura, N.H. et al. J. Biochem. 112 (4), pp. 557-561 (1992).
GenBank accession No. AAB30623, Jordan-Starck, T.C. et al. J. Lipid Res. 35 (2), pp. 194-210 (1994).
GenBank accession No. AAD24461, Miyata, M. et al., Direct submission, Submitted Jan. 8, 1999, First Deaprtment of Internal Medecine, Kagoshima University.
GenBank accession No. AAF06365, Jordan-Starck, T.C. et al., Direct Submission, submittted Sep. 2, 1999, Molecular Developmental Biology.
GenBank accession No. AAF67184, You K.H. and Jeon J.H. Direct Submission, submitted Mar. 22, 2000, Department of Biology, Chungnam National University.
GenBank accession No. AAF67185, You K.H. and Jeon J.H. Direct Submission, submitted Mar. 22, 2000, Department of Biology, Chungnam National University.
GenBank accession No. AAG31162,Park, J. H. et al. Direct Submission Submitted Oct. 19, 2000 Protein Eng. Laboratory, Korea Res.lnst. of Bioscience and Biotechnology.
GenBank accession No. AAH10514, Strausberg R.L. et al., J. Proc. natl. Acad. Sci. U.S.A. 99 (26), pp. 16899-16903 (2002).
GenBank accession No. AAH19588, Strausberg R.L. et al., J. Proc. natl. Acad. Sci. U.S.A. 99 (26), pp. 16899-16903 (2002).
GenBank accession No. AAH61534, Strausberg R.L. et al., J. Proc. natl. Acad. Sci. U.S.A. 99 (26), pp. 16899-16903 (2002).
GenBank accession No. AAH75668, Strausberg, R. L. et al. J., Direct Submission, Proc. Natl. Acad. Sci. U.S.A. 99 (26), pp. 16899-16903 (2002), NIH MGC Project, Jun. 29, 2004.
GenBank accession No. AAP88927, Rieder, M.J. et al., Direct Submission, Submitted Jul. 11, 2003, Genome Sc., University of Washigton.
GenBank accession No. AAT08041, Kim, J.W., Direct Submission, Submitted Dec. 26, 2003, J. Obstet. & Gynecol.Catholic University Medical College.
GenBank accession No. AAV67360-Dorus, S. et al. Direct Submission, Department of Human Genetics, Medical Institute, University of Chicago, Submitted Jun. 14, 2004.

(56) References Cited

OTHER PUBLICATIONS

GenBank accession No. AAX36279-Hines, L. et al, Biological Chemistry and Molecular Pharmacology, Harvard Institute of Proteomics, submitted Jan. 4, 2005.
GenBank accession No. AAX41112-Hines, L. et al. Direct Submission, Biol. Chem. and Mol. Pharmacology, Harvard Institute of Proteomics, submitted Jan. 4, 2005.
GenBank accession No. AAX42684-Hines, L. et al. "Direct Submission" Biol.Chem. and Mol. Phar., Harvard Inst. of Proteomics, submitted Jan. 5, 2005.
GenBank accession No. ABM82371, Rolfs, A. et al., Direct Submission, submitted Jan. 22, 2007.
GenBank accession No. ABM85549, Rolfs, A. et al., Direct Submission, submitted Jan. 22, 2007.
GenBank accession No. BAA03162, You, K. -H. Direct Submission, Submitted Jan. 18, 1993.
GenBank accession No. BAE88332, Chien, H. -C. et al. Direct Submission, submitted Mar. 19, 2004.
GenBank accession No. BAE88970, Chien, H. -C. et al. Direct Submission, submitted Mar. 19, 2004.
GenBank accession No. BAG36598, Isogai, T. and Yamamoto J., Direct Submission, submitted Jan. 11, 2008.
GenBank accession No. BAG52708, Isogai, T. and Yamamoto, J., Direct Submission, submitted Jul. 4, 2002, Helix Research Institute, Genomics Laboratory.
GenBank accession No. CAA31618, Bettuzzi, S., Direct Submission, submitted Oct. 11, 1988) Ben May Institute, University of Chicago.
GenBank accession No. CAA32847, Kirszbaum, L., Direct Submission, submitted Mar. 17, 1999, Clin. Invest. 81, pp. 1858-1864 (1988).
Genbank Accession No. CAC20421; submitted Jan. 2000.
GenBank accession No. CAI45990, Bloecker H. et al., Direct Submission, submitted Jan. 20, 2005, MIPS, Ingolstaedter Landstr. 1.
Gleave, M. et al., Use of antisense oligonucleotides targeting the cytoprotective gene, clusterin, to enhance androgen- and chemosensitivity in prostate cancer. World Journal of Urology, 23(1):38-46 (2005).
Gleave, M.E. et al., Targeting anti-apoptotic genes upregulated by androgen withdrawal using antisense oligonucleotides to enhance androgen- and chemo-sensitivity in prostate cancer, Investigational New Drugs, 20:145-158 (2002).
Gleave, M.E. et al., Use of antisense oligonucleotides targeting the antiapoptotic gene, clusterin/testosterone-repressed prostate message 2, to enhance androgen sensitivity and chemosensitivity in prostate cancer, Urology, 58(Supplement 2A):39-48 (2001).
Hara, I. et al., Introduction of *Clusterin* Gene into Human Renal Cell Carcinoma Cells Enhances Their Resistance to Cytotoxic Chemotherapy through Inhibition of Apoptosis both in vitro and in vivo, Japanese Journal of Cancer Research, 92:1220-1224 (2001).
He, H-Z. et al., Alterations in expression, proteolysis and intracellular localizations of clusterin in esophageal squamous cell carcinoma, World Journal of Gastroenterology, 10(10):1387-1391 (2004).
Herbst, R. and Sandler, A., Bevacizumab and erlotinib: A promising new approach to the treatment of advanced NSCLC, Oncologist, 13:1166-1176 (2008).
Holm, P. et al., Functional mapping and single chain construction of the anti-cytokeratin 8 monoclonal antibody TS1, Molecular Immunology, 44:1075-1084 (2007).
Humphreys, D. et al., Effects of Clusterin Overexpression on TNFα- and TGFβ-Mediated Death of L929 Cells, Biochemistry, 36(49):15233-15243 (1997).
Huston, J.S. et al., Protein engineering of antibody binding sites: Recovery of specific activity in an anti-digoxin single-chain Fv analogue produced in *Escherichia coli*, Proceedings of the National Academy of Sciences, 85:5879-5883 (1988).

Hwang, W.Y.K. et al., Use of human germline genes in a CDR homology-based approach to antibody humanization, Methods: A Companion to Methods in Enzymology, 36:35-42 (2005).
International Search Report for PCT/CA2006/0001505, 5 pages (dated Dec. 27, 2006).
International Search Report for PCT/CA2013/000167, 5 pages (dated Jun. 4, 2013).
IPI No. IPI00198667.7, Mar. 14, 2003.
IPI No. IPI00291262.3, Jun. 6, 2003.
IPI No. IPI00320420.3, Jun. 11, 2003.
IPI No: IPI00400826.1, Mar. 3, 2004.
IPI No: IPI00795633.1, Oct. 31, 2006.
IPI No. IPI00753742.1, May 10, 2006.
Jo, H. et al., Cancer Cell-Derived Clusterin Modulates the Phosphatidylinositol-3'-Kinase-Akt Pathway through Attenuation of Insulin-Like Growth Factor 1 during Serum Deprivation, Molecular and Cellular Biology, 28(13):4285-4299 (2008).
Johnson, G. et al., The Kabat Database and a Bioinformatics Example, Methods in Molecular Biology, Antibody Engineering: Methods and Protocols, 248:11-25 (2004).
Jones, D.T., GenTHREADER: An Efficient and Reliable Protein Fold Recognition Method for Genomic Sequences, Journal of Molecular Biology, 287:797-815 (1999).
Jones, P.T. et al., Replacing the complementarity-determining regions in a human antibody with those from a mouse, Nature 321:522-525 (1986).
July, L.V. et al., Clusterin Expression Is Significantly Enhanced in Prostate Cancer Cells Following Androgen Withdrawal Therapy, The Prostate, 50:179-188 (2002).
July, L.V. et al., Nucleotide-based therapies targeting clusterin chemosensitize human lung adenocarcinoma cells both in vitro and in vivo, Molecular Cancer Therapeutics, 3(3):223-232 (2004).
Kalluri, R. and Weinberg, RA, The basics of epithelial-mesenchymal transition, Journal of Clinical Investigation, 119(6):1420-1428 (2009).
Kang, Y.K. et al., Overexpression of Clusterin in Human Hepatocellular Carcinoma, Human Pathology,35(11):1340-1346 (2004).
Kashmiri, S.V.S. et al., SDR grafting—a new approach to antibody humanization, Methods, 36:25-34 (2005).
Kim, S.J. et al., Antibody Engineering for the Development of Therapeutic Antibodies, Molecular Cells, 20(1):17-29 (2005).
Kruger S. et al., Value of clusterin immunoreactivity as a predictive factor in muscle-invasive urothelial bladder carcinoma, Urology, 67(1):105-109 (2006).
Kurahashi, T. et al., Expression of the secreted form of clusterin protein in renal cell carcinoma as a predictor of disease extension, BJU International, 96:895-899 (2005).
Kurisaki, K. et al., Nuclear factor YY1 Inhibits Transforming Growth Factor β- and Bone Morphogenetic Protein-Induced Cell Differentiation, Molecular and Cellular Biology, 23(13):4494-4510 (2003).
Lau, S.H. et al., Clusterin plays an important role in hepatocellular carcinoma metastasis, Oncogene, 25:1242-1250 (2006).
Lee, C-H. et al., Suppression of clusterin expression enhanced cisplatin-induced cytotoxicity on renal cell carcinoma cells, Urology, 60(3):516-520 (2002).
Lee, JM et al., The epithelial-mesenchymal transition: new insights in signaling, development, and disease, Journal of Cellular Biology, 172(7):973-981 (2006).
Lee, K-H. et al., Increased Vaccine-Specific T Cell Frequency After Peptide-Based Vaccination Correlates with Increased Susceptibility to In Vitro Stimulation but Does Not Lead to Tumor Regression, The Journal of Immunology, 163:6292-6300 (1999).
Lenferink, A.E.G. et al., Clusterin Mediates Tumor Promoting, But Not Tumor Suppressing, Effects of TGF-β1, National Research Council of Canada May 2004, Poster at NRC AGM, 2.
Lenferink, A.E.G. et al., Investigation of three new mouse mammary tumor cell lines as models for transforming growth factor (TGF)-β and Neu pathway signaling studies: identification of a novel model for TGF-β-induced epithelial-to-mesenchymal transition, Breast Cancer Research, 6:R514-R530 (2004).

(56) References Cited

OTHER PUBLICATIONS

Lenferink, A.E.G. et al., Transcriptome profiling of a TGF-β-induced epithelial-to-mesenchymal transition reveals extracellular clusterin as a target for therapeutic antibodies, Oncogene, 29(6):831-844 (2010).
Li, X. et al., Predicting Protein Disorder for N-, C- and Internal Regions, Genome Informatics, 10:30-40 (1999).
Lo, B.K.C., Antibody Humanization by CDR Grafting, Methods in Molecular Biology, 248:135-159 (2004).
Lupas, A., Prediction and Analysis of Coiled-Coil Structures, Methods in Enzymology, 266:513-524 (1996).
MacCallum, R.M. et al., Antibody-antigen Interactions: Contact Analysis and Binding Site Topography, Journal of Molecular Biology, 262:732-745 (1996).
Mirshahadi, H. and Hsueh, C., Updates in non-small cell lung cancer—insights from the 2009 45th annual meeting of the American Society of Clinical Oncology, Journal of Hematology & Oncology, 3:18 (2010).
Miyake, H. et al., Acquisition of Chemoresistant Phenotype by Overexpression of the Antiapoptotic Gene *Testosterone-repressed Prostate Message-2* in Prostate Cancer Xenograft Models, Cancer Research, 60:2547-2554 (2000).
Miyake, H. et al., Introducing the clusterin gene into human renal cell carninoma cells enhances their metastatic potential, The Journal of Urology, 167:2203-2208 (2002).
Miyake, H. et al., Overexpression of clusterin in transitional cell carcinoma of the bladder is related to disease progression and recurrence, Urology, 59(1):150-154 (2002).
Miyake, H. et al., Resistance to cytotoxic chemotherapy-induced apoptosis in human prostate cancer cells is associated with intracellular clusterin expression, Oncology Reports, 10:469-473 (2003).
NCBI accession No. NM_001831.2, first referenced 1990.
NCBI accession No. NM_013492.2, first referenced 1989.
NCBI accession No. NP_001822, first referenced 1990.
NCBI accession No. NP_038520, first referenced 1989.
NCBI Reference sequence: NP_001003370, Hartmann, K. et al., J. Biol. Chem. 266 (15) pp. 9924-9931 (1991).
NCBI Reference sequence: NP_001075413, Sep. 3, 2009.
NCBI Reference sequence: NP_001075518, Miyata, M., Circulation 104 (12) pp. 1407-1412 (2001).
NCBI Reference sequence: NP_001822, James, R. W. et al. Arterioscler. Thromb. 11 (3) pp. 645-652 (1991).
NCBI Reference sequence: NP_038520, Jenne, D.E. and Tschopp, J. Proc. natl. Acad. Sci. U.S.A. 86 (18), pp. 7123-7127 (1989).
NCBI Reference sequence: NP_444180, Collard, M. W. and Griswold, M. D., Biochemistry 26 (12) pp. 3297-3303 (1987).
NCBI Reference sequence: NP_999136, Diemer, V. et al. J. Biol. Chem. 267 (8), pp. 5257-5264 (1992).
NCBI Reference sequence: XP_001164036, Sep. 15, 2006.
NCBI Reference sequence: XP_001164195, Sep. 15, 2006.
NCBI Reference sequence: XP_001164234, Sep. 15, 2006.
NCBI Reference sequence: XP_001164274, Sep. 15, 2006.
NCBI Reference sequence: XP_001164305, Sep. 15, 2006.
NCBI Reference sequence: XP_001164341, Sep. 15, 2006.
NCBI Reference sequence: XP_001164378, Sep. 15, 2006.
NCBI Reference sequence: XP_001164413. Sep. 15, 2006.
NCBI Reference sequence: XP_001164451, Sep. 15, 2006.
NCBI Reference sequence: XP_001164491, Sep. 15, 2006.
NCBI Reference sequence: XP_001164530, Sep. 15, 2006.
NCBI Reference sequence: XP_001164568, Sep. 15, 2006.
NCBI Reference sequence: XP_001164607 Sep. 15, 2006.
NCBI Reference sequence: XP_001164647 Sep. 15, 2006.
NCBI Reference sequence: XP_001475661 Jun. 20, 2007.
NCBI Reference sequence: XP_519677 Sep. 15, 2006.
NCBI Reference sequence:NP_976084, James, R. W. et al. Arterioscler. Thromb. 11 (3) pp. 645-652 (1991).
Parczyk, K. et al., Gp80 (clusterin; TRPM-2) mRNA level is enhanced in human renal clear cell carcinomas, Journal of Cancer Research and Clinical Oncology, 120:186-188 (1994).
Park, D.C. et al. Clusterin confers paclitaxel resistance in cervical cancer, Gynecologic Oncology, 103(3):996-1000 (2006).
Park, D.C. et al., Clusterin Interacts with Paclitaxel and Confer Paclitaxel Resistance in Ovarian Cancer, Neoplasia Press, 10(9):964-972 (2008).
Paul, W.E., Fundamental Immunology, 3rd Edition, Raven Press, New York, pp. 292-295 (1993).
Pines, G. et al., Oncogenic Mutant Forms of EGFR: Lessons in Signal Transduction and Targets for Cancer Therapy, FEBS Letters, 584:2699-2706 (2010).
Portolano, S. et al., Lack of Promiscuity in Autoantigen-Specific H and L Chain Combinations as Revealed by Human H and L Chain "Roulette", The Journal of Immunology, 150:880-887 (1993).
Queen, C. et al., A humanized antibody that binds to the interleukin 2 receptor, Proceedings of the National Academy of Sciences of the United States of America, 86:10029-10033 (1989).
Redondo, M. et al., Anticlusterin treatment of breast cancer cells increases the sensitivities of chemotherapy and tamoxifen and counteracts the inhibitory action of dexamethasone on chemotherapy-induced cytotoxicity, Breast Cancer Research, 9(6):1465-5411 (2007).
Redondo, M. et al., Overexpression of Clusterin in Human Breast Carcinoma, American Journal of Pathology, 157(2):393-399 (2000).
Riechmann, L. et al., Reshaing human antibodies for therapy, Nature 332:323-327 (1988).
Ronquist, K.G. et al., Serum antibodies against prostasomal clusterin in prostate cancer patients, Scand. J. Clin. Lab Invest., 68(3):219-27 (2008).
Rost, B., Predicting One-Dimensional Protein Structure by Profile-Based Neural Networks, Methods in Enzymology, 266:525-539 (1996).
Rudikoff, S. et al., Single amino acid substitution altering antigen-binding specificity, Proceedings of the National Academy of Science of the United States of America, 79:1979-1983 (1982).
Saffer, H. et al., Clusterin Expression in Malignant Lymphomas: A Survey of 266 Cases, Modern Pathology, 15(11):1221-1226 (2002).
Sanders, M.L. et al., α-Specific Anti-clusterin Antibody: Development and Characterization, Molecular Biology of the Cell, American Society for Cell Biology, US, vol. 4, Suppl. p. 109A, 1993.
Santa Cruz Biotechnology, Inc. Clusterin-α (C-18): sc-6419, Santa Cruz Biotechnology Inc. Catalog, pp. 1 (1999).
Santa Cruz Biotechnology, Inc., Clustrein-α (B-5): sc-5289, Santa Cruz Biotechnology Inc. Catalog, pp. 1 (2004).
Scaltriti, M. et al., Clusterin (SGP-2, ApoJ) expression is downregulated in low- and high-grade human prostate cancer, International Journal of Cancer, 108(1):23-30 (2004).
Schade, B. et al., Cold Adaptation in Budding Yeast, Molecular Biology of the Cell, 15:5492-5502 (2004).
Schedule A submitted to European Patent Office Dec. 21, 2010.
Schedule B submitted to European Patent Office Sep. 2, 2011.
Schlapschy, M. et al., Functional humanization of an anti-CD30 Fab fragment for the immunotherapy of Hodgkin's lymphoma using an in vitro evolution approach, Protein Engineering, Design & Selection, 17(12):847-860 (2004).
Shigematsu, H. et al., Clinical and biological features associated with epidermal growth factor receptor gene mutations in lung cancers, Journal of the National Cancer Institute, 97:339-346 (2005).
Singh, J. et al., Transforming in the TGFβ pathway: Convergence of distinct lead generation strategies on a novel kinase pharmacophore for TβRI (ALK5), Current Opinion in Drug Discovery & Development, 74(4):437-445 (2004).
Sintich, S.M. et al., Cytotoxic Sensitivity to Tumor Necrosis Factor-α in PC3 and LNCaP Prostatic Cancer Cells Is Regulated by Extracellular Levels of SGP-2 (Clusterin), The Prostate 39:87-93 (1999).
Sintich, S.M. et al., Transforming Growth Factor-β1-Induced Proliferation of the Prostate Cancer Cell Line, TSU-Pr1: The Role of Platelet-Derived Growth Factor, Endocrinology, 140:(8):3411-3415 (1999).
So, A. et al., Antisense oligonucloetide therapy in the management of bladder cancer, Current Opinion in Urology, 15:320-327 (2005).

(56) References Cited

OTHER PUBLICATIONS

So, A. et al., Knockdown of the cytoprotective chaperone, clusterin, chemosensitizes human breast cancer cells both in vitro and in vivo, Molecular Cancer Therapy, 4(12):1837-1849 (2005).
Springate, C.M.K, et al., Efficacy of an intratumoral controlled release formulation of clusterin antisense oligonucleotide complexed with chitosan containing paclitaxel or docetaxel in prostate cancer xenograft models, Cancer Chemotherapy and Pharmacology, 56(3):239-247 (2005).
Staelens, S. et al., Humanization by variable domain resurfacing and grafting on a human IgG$_4$, using a new approach for determination of non-human like surface accessible framework residues based on homology modelling of variable domains, Molecular Immunology, 43:1243-1257 (2006).
Steinberg, J. et al., Intracellular Levels of SGP-2 (Clusterin) Correlate with Tumor Grade in Prostate Cancer, Clinical Cancer Research, 3:1707-1711 (1997).
SwissProt Accession No. P01625.2; submitted Aug. 1996.
Tamura, M. et al., Structural correlates of an anticarcinoma antibody: identification of specificity-determining residues (SDRs) and development of a minimally immunogenic antibody variant by retention of SDRs only, J. Immunol., 164(3):1432-41 (2000).
Tatusova, T. et al., Blast 2 sequences, a new tool for comparing protein and nucleotide sequences, FEMS Microbiology Letters, 174:247-250 (1999).
Thomas-Tikhonenko, A. et al., Myc-Transformed Epithelial Cells Down-Regulate Clusterin, Which Inhibits Their Growth in Vitro and Carcinogenesis in Vivo, Cancer Research, 64:3126-3136 (2004).
Tremblay, G. et al., Poster Presentations—Translational Metastasis Research, Abstract 1467: AB-1665, a therapeutic monoclonal antibody against human clusterin that blocks the epithelial-to-mesenchymal transition, Proceedings: AACR 101st Annual Meeting, 2010—Apr. 17-21, 2010 Washington, DC.
Trougakos, I.P. et al., Advances and Challenges in Basic and Translational Research on Clusterin, Cancer Research, 69(2):403-406 (2009) (including 4 pages of "Supplementary Data").
Trougakos, I.P. et al., Silencing Expression of the Clusterin/Apolipoprotein J Gene in Human Cancer Cells Using Small Interfering RNA Induces Spontaneous Apoptosis, Reduced Growth Ability, and Cell Sensitization to Genotoxic and Oxidative Stress, Cancer Research, 64(5):1834-1842 (2004).
Trougakos, I.P. et al., Differential effects of clusterin/apolipoprotein J on cellular growth and survival, Free Radical Biology & Medicine, 38:436-449 (2005).
Tsurushita, N. et al., Design of humanized antibodies: from anti-Tac to Zenapax, Methods, 36(1):69-83 (2005).
Uni-Prot/TrEMBL accession No. Q549A5_MOUSE, McLaughlin L. et al., J. Clin. Invest. 106:1105-1113 (2000) May 24, 2005.
Uni-Prot/TrEMBL accession No. Q5ISQ2_MACFA, Dorus S. et al., Cell 119:1027-1040 (2004).
Uni-Prot/TrEMBL accession No. Q6P7S6_RAT, Jul. 5, 2004.
Uni-Prot/TrEMBL accession No. Q9ERD1_RAT, Park J. H. et al., submitted Oct. 2000, Mar. 1, 2001.
UniProtKB/Swiss-Prot accession No. P05371 (CLUS_RAT), Collard M.W. and Grisworld M.D., Biochemistry 26:3297-3303 (1987).
UniProtKB/Swiss-Prot accession No. P10909 (CLUS_HUMAN), Jenne D.E. and Tschopp J., Proc. natl. Acad. Sci. U.S.A. 86:7123-7127 (1989), Jul. 1, 1989.
UniProtKB/Swiss-Prot accession No. P25473 (CLUS_CANFA), Hartmann K. et al., J. Biol. Chem, 266:9924-9931 (1991) May 1, 1992.
UniProtKB/Swiss-Prot accession No. Q06890 (CLUS_MOUSE), Lee K.-H. et al. Biochem. Biophys. Res. Commun. 194:1175-1180 (1993) PubMed: 8352774 Abstract, Feb. 1, 1995.
UniProtKB/Swiss-Prot accession No. Q29482 (CLUS_HORSE), Barber J. A. et al., submitted Nov. 1995, May 10, 2005.
UniProtKB/Swiss-Prot accession No. Q29549 (CLUS_PIG), Diemer V. et al., J. Biol. Chem. 267:5257-5264 (1992), Jul. 15, 1998.
UniProtKB/Swiss-Prot accession No. Q9XSC5 (CLUS_RABIT), Miyata M. et al., Circulation 104:1407-1412 (2001) Dec. 1, 2000.
Vajdos, F.F. et al., Comprehensive Functional Maps of the Antigen-binding Site of an Anti-ErbB2 Antibody Obtained with Shotgun Scanning Mutagenesis, The Journal of Molecular Biology, 320:415-428 (2002).
Van Der Keyl, H. et al., Disparity in the kinetics of onset of hypermutation in immunoglobulin heavy and light chains, Immunology and Cell Biology, 78:224-237 (2000).
Verhoeyen, M. et al., Reshaping Human Antibodies: Grafting an Antilysozyme Activity, Science, 239:1534-1536 (1988).
Wang, X., Expression and role of clusterin in apoptosis of prostatic epithelial cell, Journal of Modern Urology, 13(1):41-43 (2008). English Abstract.
Ward, E.S. et al., Binding activities of a repertoire of single immunoglobulin variable domains secreted from *Escherichia coli*, Nature, 341:544-546 (1989).
Wilson, M.R. et al., Clusterin binds by a multivalent mechanism to the Fc and Fab regions of IgG; Biochimica et Biophysica Acta; 1159:319-326 (1992).
Witta, S. et al., Restoring E-cadherin expression increases sensitivity to epidermal growth factor receptor inhibitors in lung cancer cell lines, Cancer Research, 66:944-950 (2006).
Written Opinion for PCT/CA2006/0001505, 9 pages (dated Dec. 27, 2006).
Wu, H. et al., Humanization of a Murine Monoclonal Antibody by Simultaneous Optimization of Framework and CDR Residues, The Journal of Molecular Biology, 294:151-162 (1999).
Wu, H., Simultaneous Humanization and Affinity Optimization of Monoclonal Antibodies, Methods in Molecular Biology, 207:197-212, Humana Press Inc., Totowa, New Jersey (2003).
Xie, D. et al., Oncogenic role of clusterin overexpression in multistage colorectal tumorigenesis and progression, World Journal of Gastroenterology, 11(21):3285-3289 (2005).
Xie, D. et al., Up-Regulated Expression of Cytoplasmic Clusterin in Human Ovarian Carcinoma, Cancer, 103(2):277-283 (2005).
Yauch, R. et al., Epithelial versus mesenchymal phenotype determines in vitro sensitivity and predicts clinical activity of erlotinib in lung cancer patients, Clinical Cancer Research, 5:8686-8698 (2005).
Zellweger, T. et al., Antitumor Activity of Antisense Clusterin Oligonucleotides Is Improved in Vitro and in Vivo by Incorporation of 2'-O-(2-Methoxy)Ethyl Chemistry, The Journal of Pharmacology and Experimental Therapeutics, 298(3):934-940 (2001).
Zellweger, T. et al., Chemosensitization of Human Renal Cell Cancer Using Antisense Oligonucleotides Targeting the Antiapoptotic Gene Clusterin, Neoplasia, 3(4):360-367 (2001).
Zhang, L-Y. et al., Loss of clusterin both in serum and tissue correlates with the tumorigenesis of esophageal squamous cell carcinoma via proteomics approaches, World Journal of Gastroenterology, 9(4):650-654 (2003).
Zhang, Y. et al., Preparation and characterization of antibodies against clusterin, Chinese Journal of Cellular and Molecular Immunology, 24(1):45-48 (2008).
Zhou, W. et al., A novel anti-proliferative property of clusterin in prostate cancer cells, Life Sciences, 72(1):11-21 (2002).
Zoubeidi, A. et al., Clusterin Facilitates COMMD1 and I-κB Degradation to Enhance NF-κB Activity in Prostate Cancer Cells, Molecular Cancer Research, 8:119-130 (2010).
Chi, K.N. et al., a phase I study of OGX-011, a 2'-methoxyethyl phosphorothioate antisense to clusterin, in combination with docetaxel in patients with advanced cancer, Clin. Cancer Res., 14(3):833-9 (2008).
Chowdhury, P.S. and Vasmatzis, G., Engineering scFvs for Improved Stability, Methods in Molecular Biology, Recombinant Antibodies for Cancer Therapy: Methods and Protocols, Welschof, M. and Krauss, J. ed., vol. 207, chapter 14, pp. 237-254 (2003).
International Search Report for PCT/CA2010/001882, 5 pages (Feb. 16, 2011).
Roguska, M.A. et al., A comparison of two murine monoclonal antibodies humanized by CDR-grafting and variable domain resurfacing, Protein. Eng., 9(10):895-904 (1996).

(56) References Cited

OTHER PUBLICATIONS

Roitt, I. et al., Immunology, Mosby, chapter 6, pp. 110-111 (2000) [with English translation].

Tremblay, G.B. et al., Abstract LB-33: Pre-clinical evaluation of AB-16B5, a monoclonal antibody specific for tumor-associated sCLU, demonstrates therapeutic potential as an inhibitor of EMT in prostate, pancreatic and lung cancer, Cancer Research, Abstract, 1 page (2011).

Tremblay, G.B. et al., Abstract LB-33: Pre-clinical evaluation of AB-16B5, a monoclonal antibody specific for tumor-associated sCLU, demonstrates therapeutic potential as an inhibitor of EMT in prostate, pancreatic and lung cancer, Cancer Research, Poster #LB-33, 1 page (2011).

Wei, L. et al., Roles of clusterin in progression, chemoresistance and metastasis of human ovarian cancer, Int. J. Cancer., 125(4):791-806 (2009).

Written Opinion for PCT/CA2010/001882, 7 pages (dated Feb. 16, 2011).

Written Opinion for PCT/CA2013/000167, 7 pages (dated Jun. 4, 2013).

Berx G, et al. Pre-EMTing metastasis? Recapitulation of morphogenetic processes in cancer. Chn. Exp. Metastasis. 24: 587, 2007.

Chi, K.N. et al., A Phase I Study of OGX-011, a 2'-Methoxyethyl Phosphorothioate Antisense to Clusterin, in Combination with Docetaxel in Patients with Advanced Cancer, Clin Cancer Res. 14(3):833-839, 2008.

Gupta GP, et al. Cancer metastasis: building a framework. Cell. 127: 679, 2006.

Mader, A. and R. Kunert, Humanization Strategies for an Anti-Idiotypic Antibody Mimicking HIV-1 gp41, Prot. Engin. Design & Select. 23(12): 947-954, 2010: published online Oct. 30, 2010.

Margreitter, C. et al., Antibody Humanization by Molecular Dynamics Simulations- In Silico Guided Selection of Critical Backmutations, J. Mol. Recognit 29(6), 266-275, 2016.

Massague J. TGFbeta in Cancer. (2008) Cell. 134: 215.

Mourra N, et al. (2007) Clusterin is highly expressed in pancreatic endocrine tumours but not in solid pseudopapillary tumours. Histopathology. 50: 331, 2007.

Nguyen, H.P. et al., Protein Data Bank No. 1Q9Q (now replaced by No. 3sy0), first referenced 2011 (2 pages).

Pirker, R., J. R., Peirera et al., (2012) "EGFR expression as a predictor of survival for first-line chemotherapy plus cetuximab in patients with advanced non-small-cell lung cancer: analysis of data from the phase 3 FLEX study." *Lancet* 13:33.

Ranney, M.K. et al., Multiple Pathways Regulating the Anti-Apoptotic Protein Clusterin in Breast Cancer, Biochimica et Biophysica Acta, 1772, 1103-1111, 2007.

Schmiedel, J. et al., Matuzumab Binding to EGFR Prevents the Conformational Rearrangement Required for Dimerization, Cancer Cell, 13(4): 365-373, 2008.

Springer T.A. et al., Protein Data Bank No. 1TY7 (now replaced by No. 2vc2), first referenced 2008 (4 pages).

Tan, P. et al, "Superhumanized" Antibodies: Reduction of Immunogenic Potential by Complementarrity-Determining Region Grafting with Human Germline Sequences: Application to an Anti-CD28, J. Immunol. 169:1119-1125, 2002.

Trougakos, I.P. et al., Intracellular Clusterin Inhibits Mitochondrial Apoptosis by Suppressing p53-Activating Stress Signals and Stabilizing the Cytosolic Ku70-Bax Protein Complex, Clin Cancer Res, 15(1) 48-59, 2009.

Watari H, et al. , Clusterin expression predicts survival of invasive cervical cancer patients treated with radical hysterectomy and systematic lymphadenectomy. Gynecol. Oncol. 108: 527, 2008.

Zhang S, et al., Clusterin expression and univariate analysis of overall survival in human breast cancer. Technol. Cancer Res. Treat. 5: 573, 2006.

\* cited by examiner

| Cell line | [sCLU] (ng/ml) |
|---|---|
| A549 | 71.9 |
| H226 | <10 |
| H292 | 40.8 |
| H460 | 103 |
| H1299 | 13.6 |

CO-USE OF A CLUSTERIN INHIBITOR WITH AN EGFR INHIBITOR TO TREAT CANCER

PRIORITY CLAIM

This patent application is a national stage filing under 35 U.S.C. §371 of international application No. PCT/CA2013/000167 filed on Feb. 22, 2013, which claimed priority to U.S. provisional application No. 61/601,786 filed Feb. 22, 2012. The entire contents of each of these priority applications are incorporated herein by reference.

SEQUENCE LISTING

In accordance with 37 C.F.R. §1,52(e)(5), a Sequence Listing in the form of a text file (entitled "Sequence Listing", created on Jul. 28, 2014 and of 78 kilobytes) is incorporated herein by reference in its entirety.

FIELD OF THE INVENTION

The invention relates to combination of a clusterin inhibitor with an inhibitor of epidermal growth factor receptor (EGFR) for use in treatment of cancer. More particularly, the present invention encompasses the use of a clusterin inhibitor, such as an anti-clusterin antibody, to restore the sensitivity of cancer cells to an EGFR inhibitor or to potentiate the effect of the EGFR inhibitor.

BACKGROUND OF THE INVENTION

Development of resistance to chemotherapy and invasion to other secondary sites are common features of solid tumor malignancies. It is well known that development of resistance to chemotherapeutic agents is caused by over-expression of proteins involved in drug and apoptosis resistance. The invasion process is also fairly well documented. Tumor invasion is caused by an increased motility of cancer cells and the expression of genes that cause degradation of the proteins in the extra-cellular matrix. There is growing evidence that resistance to chemotherapy and tumor invasion might share a common starting point through a biological process called the epithelial-to-mesenchymal transition (EMT). Recent studies have demonstrated that transforming growth factor beta (TGFβ) may be a critical mediator of EMT. Despite these advances, few therapeutic avenues are available to inhibit the development of chemo-resistance and the spread of cancer to other organs. It has also emerged in the recent literature that certain tumor cells undergoing EMT dedifferentiate and adopt stem cell-like properties (cancer stem cells or CSCs). As is the case for normal stem cells, CSCs are inherently refractory to chemotherapy and radiation therapy. Therefore, targeting a specific regulator of EMT and CSC maintenance represents a very promising therapeutic strategy to increase response to chemotherapeutic agents and to prevent recurrence of cancer.

Utilizing well characterized cell lines as models of EMT, proteins were identified that were up-regulated upon induction of EMT. One of these, a secreted protein termed clusterin (sCLU), was found to be stimulated during EMT and could, on its own, promote the EMT process (Lenferink et al., 2009). Several high-affinity antibodies were generated that interact with sCLU, which when tested in cell-based assays for their ability to block the EMT, those antibodies that neutralized EMT all bound to the same critical amino acid sequence in the sCLU protein. This discovery demonstrated that a specific region of sCLU was responsible for mediating its EMT-promoting activity. By blocking the EMT-epitope in sCLU, the antibodies, in particular an antibody designated 16B5 could block EMT as exemplified by the maintenance of the membrane expression of the epithelial cell marker, E-cadherin, when incubated with cancer cells. Furthermore, human xenograft animal studies using prostate cancer and pancreatic cancer tumors showed that blocking the activity of tumor-associated sCLU resulted in the increased response to standard chemotherapeutic drugs such as docetaxel and gemcitabine, as measured by a significant reduction in tumor growth. Taken together, these results demonstrated that blocking EMT with an antibody capable of interacting with a specific region in sCLU resulted in tumor growth inhibition and increased response to cytotoxic drugs (see international application No. PCT/CA2006/001505 published under No. WO2007/030930 and international application No. PCT/CA2010/0001882 published under No. WO2011/063523, the entire content of which is incorporated herein by reference Lung cancer is one of the most common cancers and a leading cause of death worldwide, with over a million cases diagnosed yearly and non-small cell lung cancer (NSCLC) accounts for more than 80% of all lung cancers. Despite recent improvements in diagnostic and therapeutic approaches, the majority of patients are diagnosed with advanced NSCLC where the median survival remains poor (Adamo et al., 2009).

One of the most important targets in NSCLC is the epidermal growth factor receptor (EGFR), a member of the ErbB family of receptor tyrosine kinases, that is a cell membrane receptor that plays an important role in proliferation and survival of cancer cells. It is a large transmembrane glycoprotein that serves as a receptor for EGF and several additional endogenous ligands. It has three domains consisting of an extracellular region, a transmembrane domain and an intracellular tyrosine kinase (TK) domain. Functionally, ligand binding to EGFR induces receptor dimerization leading to a structural change that promotes autophosphorylation and activation of the intracellular TK domain. Consequently, EGFR activation influences multiple downstream signaling pathways, including Ras/Raf/mitogen-activated protein kinase (MAPK) and the phosphatidylinositol-3'-kinase (PI3K)/Akt pathway, which influence cell proliferation, invasiveness, motility, survival and apoptosis (Shigematsu et al., 2005).

Although EGFR is ubiquitously expressed, it is often modified in tumors cells. These modifications include gene amplification, overexpression of ligands and/or receptors and activating mutations. Overexpression or dysregulation of EGFR or its primary ligands is characteristic of many solid human tumors, including lung cancer. In NSCLC, between 43 and 83% of tumors overexpress EGFR (Adamo et al., 2009). Several agents against EGFR such as monoclonal antibodies that target the extracellular domain or small molecules are able to inhibit the TK activity.

The status of EGFR in metastatic NSCLC and the response to chemotherapy is the subject of much debate. Despite the high proportion of tumors with increased expression of EGFR, some clinical studies have shown that this was a poor predictor of response in first-line therapy (Barr et al., 2008). Furthermore, despite a mild but significant response in patients treated first-line with cisplatin, vinorelbine and cetuximab (EGFR monoclonal antibody) compared to chemotherapy alone, there was no correlation between cetuximab and EGFR over-expression (Mirshahidi and Hsueh, 2010). Overall, an overwhelming amount of clinical results with EGRF inhibitors in NSCLC showed that the status of the receptor was not important in first-line therapy until a recent study reported results showing that patients with high EGFR expression that were treated with cetuximab and chemotherapy exhibited an increase in overall survival compared to chemotherapy alone (Pirker et al., 2012). It is clear from these results that there are other mechanisms involving EGFR in tumors that influence the response of NSCLC patients to EGFR inhibitors.

Additional characteristics of EGFR that likely influence the response of inhibitors are those that permit the binding of small molecules to the TK activity of the receptor. A few have been developed and approved for cancer indications including gefitinib and erlotinib, two small molecules that mimic ATP-binding to this region thus preventing intracellular signaling. Neither of these inhibitors was found to be active in NSCLC in first-line therapy but significant clinical responses were achieved in second- and third line settings (Mirshahidi and Hsueh, 2010). Interestingly, EGFR overexpression had no influence on patient response but it was discovered that activating mutations in EGFR and certain other genes were critical. For example, activating mutations were found to lead to significant increase in progression free survival in patients treated with gefitinib (Costanzo et al., 2011). In addition, NSCLC patients treated with erlotinib who also had mutations in a gene called KRAS, showed no response (Herbst and Sandler, 2008). Thus, patient selection is critical for attempting to understand if they will be responders to EGFR TK inhibitors.

As described above, EMT can have a tremendous influence on the way tumors cells will respond to therapy and the ability of cancer cells to remain epithelial is critical for this response. In cell-based studies, cells that have increased expression of the epithelial cell marker, E-cadherin, are more sensitive to EGFR inhibitors (Barr et al., 2008). In agreement with these observations, there was a correlation between E-cadherin expression and sensitivity to erlotinib (Yauch et al., 2005). At the tumor level, it has been shown that restoration of E-cadherin expression increases sensitivity to EGFR inhibitors (Witta et al., 2006). To date, however, the link between EMT and EGFR status in clinical trials has not been clearly examined. However, given the lack of correlation between EGFR overexpression and response to EGFR inhibitors and the influence of activating EGFR mutations on their response, it is probable that additional influences such as EMT might be directly involved in increasing the efficacy of EGFR inhibitors in NSCLC patients.

This present application provides a method of treatment with an antibody that blocks EMT by inhibiting sCLU in tumors that express EGFR. The EGFR status in these tumors might include EGFR gene amplifications or amplification in EGFR ligands. Furthermore, the tumors cells might include increased autocrine signaling through EGFR and EGFR protein partners. The EGFR status might also include activating mutations in EGFR that cause the receptor to exhibit increased activity. In another embodiment, the tumors might be sensitive or resistant to EGFR inhibitors, including monoclonal antibodies against EGFR or small molecule inhibitors that abrogate the activity of EGFR. Furthermore, EGFR status might also include tumors that were a priori negative for EGFR expression that have reacquired EGFR.

When NSCLC cell lines that express sCLU are exposed to an anti-clusterin antibody, both the expression and the activation of EGFR are increased. In parallel, by virtue of EMT inhibition by the anti-clusterin antibody, the NSCLC cell lines also show increased E-cadherin expression. Taken together, NSCLC patients treated with a clusterin inhibitor in combination with EGFR inhibitors may show an increased response to the EGFR inhibitors.

SUMMARY OF THE INVENTION

The present invention generally relates to a combination of a clusterin inhibitor and EGFR inhibitors for cancer treatment.

Methods of the present invention encompass administration of a clusterin inhibitor capable of inhibiting epithelial-to-mesenchymal transition (EMT) and an EGFR inhibitor to an individual in need. An EGFR inhibitor may also be administered separately, concurrently or sequentially with the clusterin inhibitor.

The clusterin inhibitor may be administered especially when EGFR resistance is observed, detected or suspected.

Methods of the present invention also comprise administering a clusterin inhibitor to prevent EGFR resistance or to sensitize cancer cells to an EGFR inhibitor.

DETAILED DESCRIPTION OF THE INVENTION

Figures 1, 2:
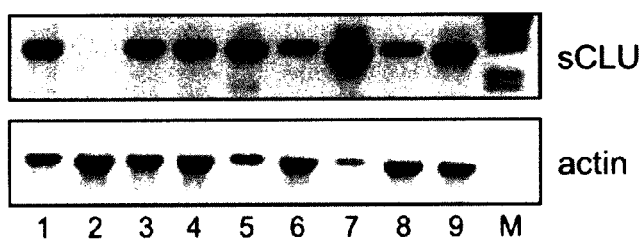
FIG. 1. Lung cancer cell lines express clusterin. This figure shows RT-PCR analysis of clusterin mRNA expression in several cell lines derived from NSCLC (upper panel). As a control, the mRNA from actin was also amplified (lower panel) to ensure equal amounts a starting material in each reaction.
FIG. 2. Lung cancer cell lines express clusterin (sCLU). This figure shows the quantification of sCLU that is secreted by lung cancer cell lines. The quantities were measured with a sCLU-specific ELISA and are expressed in ng/ml.

Epithelial growth factor receptor (EGFR) is overexpressed in several types of epithelial carcinomas. The existence of EGFR genetic alterations may render tumors more susceptible to EGFR inhibitors. However, patients with initial response to EGFR tyrosine kinase inibitors (TKIs) relapse within an average of one year. Although it has been shown that deletions in EGFR exon 9 or L858R mutations results in favorable clinical outcome, secondary molecular event such as mutations T790M, L747S and/or D761Y are associated with resistance and tumor relapse. Amplification of the MET receptor and activation of IGFR signaling that both activate the PI3/AKT pathway independently of EGFR have also been shown to drive secondary resistance.

The Applicant has come to the unexpected discovery that EGFR expression and phosphorylation is increased in cancer cells treated with a clusterin inhibitor. Treatment of cancer cells with the clusterin inhibitor is also accompanied with reappearance of an epithelial phenotype of the cancer cell, as illustrated by an increased E-cadherin expression at the cell surface.

Thus, not only may clusterin inhibitors induce reversal of the EMT phenotype, they may restore sensitivity of cancer cells to EGFR inhibitors.

The present invention generally relates to a combination of a clusterin inhibitor and EGFR inhibitors for use in cancer treatment.

The pharmaceutical combination may particularly comprise a clusterin inhibitor in association with a pharmaceutically acceptable carrier and an EGFR inhibitor in association with a pharmaceutically acceptable carrier.

Methods of the present invention encompass administration of a clusterin inhibitor and an EGFR inhibitor to an individual in need. The EGFR inhibitor may be administered separately, concurrently or sequentially with the clusterin inhibitor.

The clusterin inhibitor may be administered especially when EGFR resistance is observed, detected or suspected.

Methods of the present invention also comprise administering a clusterin inhibitor to prevent EGFR resistance or to sensitize cancer cells to an EGFR inhibitor.

In one aspect of the invention, the clusterin inhibitor may be administered prior to the EGFR inhibitor. For example, the clusterin inhibitor may be administered from a few hours to several days or months prior to administration of the EGFR inhibitor. In another aspect of the invention, the clusterin inhibitor may also be administered at the same time (e.g., same day) or between each treatment with the EGFR inhibitor.

In accordance with the present invention, the clusterin inhibitor may be administered in multiple doses prior to administration of the EGFR inhibitor, e.g., daily, every other day, once a week, twice a week, etc.

The method may also comprise testing for reversal of the epithelial-to-mesenchymal phenotype of the cancer cells before administration of the EGFR inhibitor. The EMT status may be determined, for example, by measuring expression levels of one or more genes/protein selected from E-cadherin, RAB25, integrin beta 6, vimentin, ZEBI and SIPI.

Clusterin inhibitors may be identified by their ability to impair clusterin expression, secretion or clusterin activity.

Exemplary embodiments of clusterin inhibitors include those identified, for example, by their ability to interfere with the EMT-promoting effect of secreted clusterin (sCLU) or of TGF-β. For example, carcinoma cells (e.g., 4T1: breast carcinoma cells, DU145: prostate cancer cells, etc.) may be treated with a putative clusterin inhibitor in the presence of TGF-β or sCLU and markers of EMT may be assessed as described below. A putative compound, which is capable of increasing the expression of epithelial markers and/or reducing the expression of mesenchymal markers, may be identified as a suitable clusterin inhibitor.

Alternatively, the motility of carcinoma cells in the presence of the putative clusterin inhibitor may be assessed. For example, carcinoma cells may be treated with a putative clusterin inhibitor in the presence of TGF-β or sCLU and a wound healing assay or a black ink motility assay may be carried out as described for example in PCT/CA2006/001505. A putative compound, which is capable of inhibiting or reducing the motility of carcinoma cells in these types of assays, may be identified as a suitable clusterin inhibitor. It is to be understood that other techniques may be used to identified suitable clusterin inhibitors.

Clusterin inhibitors particularly encompassed by the present invention include for example, anti-clusterin antibodies or antigen binding fragments thereof.

In accordance with the present invention, clusterin inhibitors include anti-clusterin antibodies or antigen binding fragment capable of inhibiting EMT (e.g., in carcinoma cells).

Commonly used molecular markers of EMT include, for example, a reduced expression of E-cadherin, cytokeratin and β-catenin (in the membrane) and/or an increased expression of Snail, Slug, Twist, ZEB1, ZEB2, N-cadherin, vimentin, a-smooth muscle actin, matrix metalloproteinases etc. (see for example, Kalluri and Weinberg, The Journal of Clinical Investigation, 119(6), p 1420-1428; 2009; Fassina et al., Modern Pathology, 25; p 86-99; 2012; Lee et al., JCB; 172; p 973-981; 2006). An EMT phenotype may also be distinguished by an increased capacity for migration, invasion of by resistance to anoikis/apoptosis. Cells that are undergoing epithelial-to-mesenchymal transition may thus be detected by a reduction of epithelial markers and apparition of mesenchymal markers or EMT phenotypes.

Expression of markers may generally be determined by comparing their level of cellular expression (at the genetic level or at the protein level (e.g., including cell surface expression) in one state in comparison with another state. For example, the level of expression of one or more specific markers may be determined in cancerous cells in comparison with non-cancerous cells. Alternatively, the level of expression of one or more specific markers may be determined in cancerous cells that are resistant to a EGFR inhibitor in comparison with cancerous cells that are sensitive to the EGFR inhibitor. Furthermore, level of expression of one or more specific markers may be evaluated over values that are statistically representative of controls.

Individuals who would benefit from such treatment include those having carcinoma (i.e., epithelial carcinoma) including, prostate cancer, breast cancer (e.g., triple negative or basal-like), endometrial carcinoma, ovarian carcinoma, hepatocellular carcinoma, colorectal carcinoma, head and neck carcinoma (e.g., head and neck squamous cell carcinoma), lung carcinoma (e.g., non-small cell lung cancer), pancreatic cancer, renal cell carcinoma, etc. (including advanced or metastatic forms of these cancers).

Exemplary embodiments of anti-clusterin antibodies that may be used to carry the present invention include those that are capable of binding to amino acids 421 and 443 of a C-terminal portion of a β-subunit of human clusterin. More particular embodiments of antibodies or antigen binding fragment encompassed by the present invention include those described in international application No. PCT/CA2006/001505 published under No. WO2007/030930 and international application No. PCT/CA2010/0001882 published under No. WO2011/063523.

The present invention especially encompasses antibodies and antigen binding fragment having at least one complementary determining region (CDRH1, CDRH2, CDRH3, CDRL1, CDRL2 and/or CDRL3) identical to those of the antibodies identified as 16B5, 21B12, 20E11, 16C11 and 11E2. More particularly, the present invention especially encompasses antibodies and antigen binding fragment having a light chain and/or heavy chain identical to those of identified as 16B5, 21B12, 20E11, 16C11 and 11E2 (see also PCT/CA2006/001505) or to those identified as humanized 16B5 (h16B5), humanized 21B12 (h21B12), h16B5 VL consensus 1, h16B5 VL consensus 2, h16B5 VL consensus 3, h16B5 VH consensus 1, h16B5 VH consensus 2, h16B5 VH consensus 3, h21B12 VL consensus 1, h21B12 VL consensus 2, h21B12 VL consensus 3, h21B12 VH consensus 1, h21B12 VH consensus 2 or h21B12 VH consensus 3 (see also PCT/CA2010/0001882).

The amino acid sequence of the light chain and/or heavy chain variable regions of the antibody identified as 20E11, 16C11 and 11E2 are presented in SEQ ID NOs.:62-67, where the predicted complementarity determining regions are shown in bold.

Other exemplary embodiments of antibodies and antigen binding fragments include those that can compete with the antibodies identified herein.

The invention encompasses monoclonal antibodies, polyclonal antibodies, chimeric antibodies, humanized antibodies and human antibodies (isolated) as well as antigen binding fragments having the characteristics described herein. Antibodies or antigen binding fragments encompassing permutations of the light and/or heavy chains between a monoclonal, chimeric, humanized or human antibody are also encompassed herewith.

The antibodies or antigen binding fragments of the present invention may thus comprise amino acids of a human constant region and/or framework amino acids of a human antibody.

The term "antibody" refers to intact antibody, monoclonal or polyclonal antibodies. The term "antibody" also encompasses multispecific antibodies such as bispecific antibodies.

Human antibodies are usually made of two light chains and two heavy chains each comprising variable regions and constant regions. The light chain variable region comprises 3 CDRs, identified herein as CDRL1, CDRL2 and CDRL3 flanked by framework regions. The heavy chain variable region comprises 3 CDRs, identified herein as CDRH1, CDRH2 and CDRH3 flanked by framework regions.

The term "antigen-binding fragment", as used herein, refers to one or more fragments of an antibody that retain the ability to bind to an antigen (e.g., KAAG1, secreted form of KAAG1 or variants thereof). It has been shown that the antigen-binding function of an antibody can be performed by fragments of an intact antibody. Examples of binding fragments encompassed within the term "antigen-binding fragment" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_H$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR), e.g., $V_H$CDR3. Furthermore, although the two domains of the Fv fragment, $V_L$ and $V_H$, are coded for by separate genes, they can be joined, using recombinant methods, by a synthetic linker that enables them to be made as a single polypeptide chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding fragment" of an antibody. Furthermore, the antigen-binding fragments include binding-domain immunoglobulin fusion proteins comprising (i) a binding domain polypeptide (such as a heavy chain variable region, a light chain variable region, or a heavy chain variable region fused to a light chain variable region via a linker peptide) that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The hinge region may be modified by replacing one or more cysteine residues with serine residues so as to prevent dimerization. Such binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

A typical antigen binding site is comprised of the variable regions formed by the pairing of a light chain immunoglobulin and a heavy chain immunoglobulin. The structure of the antibody variable regions is very consistent and exhibits very similar structures. These variable regions are typically comprised of relatively homologous framework regions (FR) interspaced with three hypervariable regions termed Complementarity Determining Regions (CDRs). The overall binding activity of the antigen binding fragment is often dictated by the sequence of the CDRs. The FRs often play a role in the proper positioning and alignment in three dimensions of the CDRs for optimal antigen binding.

Antibodies and/or antigen binding fragments of the present invention may originate, for example, from a mouse, a rat or any other mammal or from other sources such as through recombinant DNA technologies.

Other clusterin inhibitor may include for example and without limitation siRNAs (e.g., targeting clusterin RNA) and antisenses (e.g., targeting clusterin RNA).

Exemplary embodiments of antisense include for example, those described in U.S. Pat. No. 7,569,551 (the entire content of which is incorporated herein by reference) and especially include OGX-011 (a.k.a., custirsen sodium, OncoGenex, see also SEQ ID NO.:61).

Exemplary embodiment of EGFR inhibitors include tyrosine kinase inhibitors such as, for example, gefitinib, erlotinib, imatinib, lapatinib or semazinib. Other exemplary embodiments of EGFR inhibitors include for example, monoclonal antibodies such as cetuximab, panitumumab, nimotuzumab, or metuzumab.

Other individuals who would benefit from treatment with the pharmaceutical combinations of the present invention include those that have a tumor which is resistant to one or more EGFR inhibitors. Such individuals may be selected prior to administration of the pharmaceutical combination.

EGFR resistance may be determined by evaluating clinical parameters such as tumor relapse or by measuring molecular markers of resistance, e.g., mutations, amplifications in EGFR or in the EGFR pathway (RAS/MAPK, phospholipase C, phosphatidylinositol 3-kinase/AKT, SRC/FAK pathways, etc.) and/or EMT markers.

Testing for resistance to an EGFR inhibitor may thus includes determining the presence of mutation in EGFR (e.g., mutation in the tyrosine kinase domain, truncating mutations, insertions), determining EGFR amplification.

As used herein "pharmaceutically acceptable carrier" or "pharmaceutical carrier" are known in the art and include, but are not limited to, 0.01-0.1 M or 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's orfixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

The experiments described herein were carried out with a humanized form of 16B5 (h16B5).

EXAMPLES

Example 1

NSCLC Cell Lines Express sCLU

We wished to determine if clusterin was expressed in cell lines derived from NSCLC tumors. As a first step, total RNA was prepared from each cell line and used as a template to prepare cDNA with random primed oligonucleotides. RT-PCR was carried out using methods known to those skilled in the art with human clusterin gene-specific oligonucleotides. The 5'-primer (ogs1788) is encoded by the sequence shown in SEQ ID NO:57 and the 3'-primer (ogs1721) is encoded by the sequence shown in SEQ ID NO:58. The PCR product is 1412 by in length. As a control for the amount of total RNA in each reaction, a parallel RT-PCR reaction was performed with oligonucleotides specific for the human house-keeping gene actin. The 5'-primer (ogs387) is encoded by the sequence shown in SEQ ID NO:59 and the 3'-primer (ogs965) is encoded by the sequence shown in SEQ ID NO:60. The PCR product is 746 by in length. As shown in FIG. 1, all NSCLC cell lines analyzed except for one, contained mRNA encoding clusterin, which was detected at different levels. As expected, actin was present in all RNA samples indicating that there was an approximately equal amount of starting total RNA in each RT-PCR reaction. The cell lines used in this analysis were: lane 1, A549; lane 2, EKVX; lane 3, HOP-62; lane 4, HOP-92; lane 5, H322M; lane 6, H226; lane 7, H23; lane 8, H460; and lane 9, H522.

In parallel, we determined if sCLU was secreted by the NSCLC cell lines. A549, H226, H292, H460 and H1299 cells were purchased from ATCC (Manassas, Va.) and cultured according to the manufacturer's instructions. Following several days in culture and when the cells reached confluence, the conditioned medium from each cell line was collected for analysis. A commercial ELISA kit (BioVendor LLC, Candler, N.C.) designed to measure human clusterin was obtained and the analysis was conducted according to the manufacturer's instructions. As shown in the table of FIG. 2, all five media samples contained sCLU levels that ranged from 13.6 ng/ml to greater than 100 ng/ml, with the exception of the H226 cell line which had levels below 10 ng/ml.

Taken together, these results show that cancer cell lines derived from patients with NSCLC secrete sCLU in abundance and have the potential of responding to antibodies, such as h16B5, that inhibit the EMT-inducing activity of sCLU.

Example 2

Figure 3:
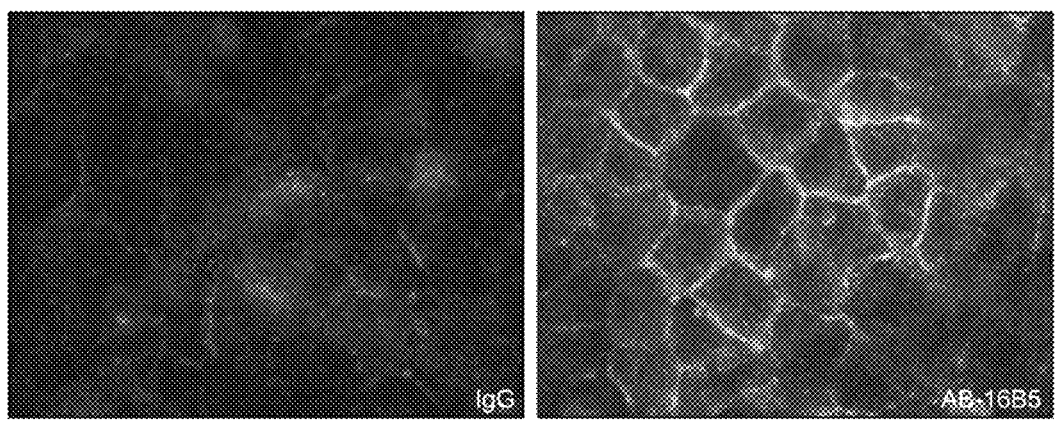
FIG. 3. h16B5 increases E-cadherin expression in lung cancer cell lines. This figure demonstrates the increase in the epithelial character of A549 NSCLC cells when incubated with the sCLU inhibitor, h16B5. The left panel shows the cells incubated with a control IgG for 48 h whereas the right panel shows cells incubated with h16B5 under identical conditions.

Incubation of NSCLC Cells with h16B5 Leads to an Increase in the Expression of the Epithelial Cell Marker, E-Cadherin We also examined the expression of E-cadherin by monitoring its expression on the surface of A549 cells using immunofluorescence. Briefly, the cells were seeded on coverslips and incubated with either a control IgG or h16B5 at 10 µg/ml for 48 h. Following this incubation, the cells were fixed with paraformaldehyde and incubated with a mouse anti-human E-cadherin antibody (manufacturer) for 1 h. After washing, the E-cadherin stained cells were incubated with a secondary antibody conjugated to Rhodamine Red-X. The slides were mounted and specific E-cadherin staining was visualized by fluorescence microscopy. As shown in FIG. 3, A549 cells have low expression of E-cadherin on their cell surface and incubation for 48 h with a non-specific IgG did not increase the level of this protein (see left panel). By contrast, incubation of the cells with h16B5 caused a marked increase in the intensity of E-cadherin staining on the surface of A549 cells (see right panel). This indicates that the epithelial character of the cells is very high.

Example 3

Figure 4:
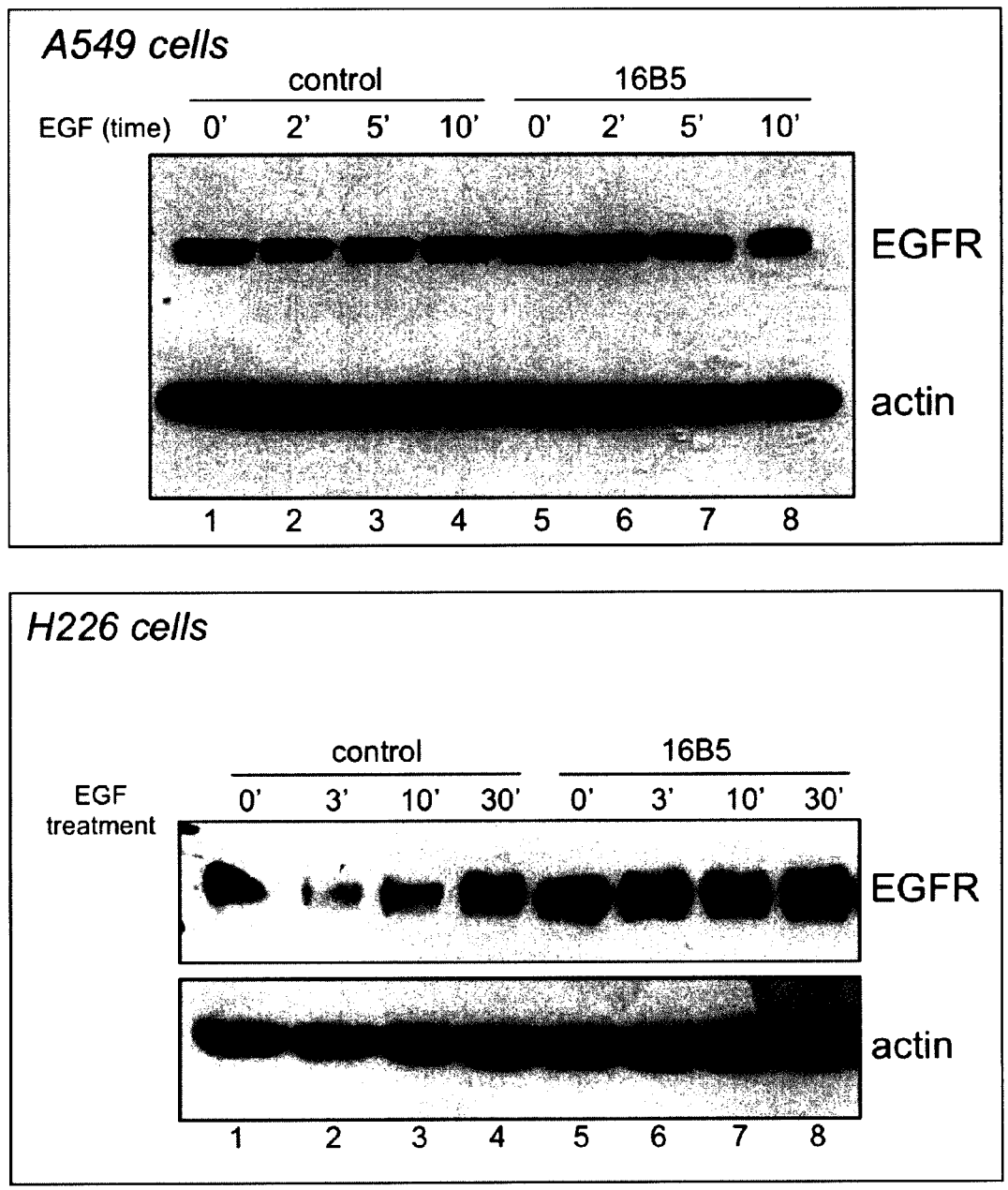
FIG. 4. Treatment of NSCLC cells with h16B5 results in increased EGFR expression. EGFR expression in the presence of control vehicle or h16B5 was measured using an EGFR-specific antibody in whole cell lysates prepared from either A549 or H226 cells.

Inhibition of sCLU with h16B5 Causes an Increase in EGFR Expression and Phosphorylation in NSCLC Cells In this example, we examine if inhibiting EMT using h16B5 resulted in any effect on the status of EGFR in NSCLC cell lines. In order to address this question, conditions were optimized to measure the expression and phosphorylation of the receptor in these cells. EGFR is known to be phosphorylated very rapidly following exposure to its ligands, including EGF. In parallel with this phosphorylation, the receptor is internalized and recycled and its presence is lost from the cell surface. Two cell lines, A549 and H226, which secreted relatively high levels of sCLU were selected for this analysis. The cells were seeded in multi-well plates and treated for 48 h with 10 µg/ml h16B5, 10 µg/ml control IgG or the vehicle, PBS. Following this incubation, the cells were treated with EGF (10 ng/ml) and the cells were harvested at different times and converted to lysates. These lysates were electrophoresed by SDS-PAGE, the proteins transferred to a nylon membrane and used in Western blots to examine the expression or phosphorylation of EGFR. To measure the expression of EGFR, a commercial antibody designated clone 1005 (Santa Cruz, Biotech, Santa Cruz, Calif.) was used whereas the phosphorylation of EGFR was monitored with an anti-phosphotyrosine antibody designated clone 4G10 (Millipore, Etobicoke, ON). As shown in FIG. 4, A549 cells that were treated with the vehicle control for 48 h followed by EGFR displayed a decrease in EGFR expression, as expected, which is rapidly restored after 10 min (upper panel: compare lane 1 with lane 2). By contrast, A549 cells treated with h16B5 anti-sCLU antibody protected the cells from the EGF-induced degradation of the receptor (upper panel: compare lane 5 with lane 6). To control for the amount of protein in each lane, the membrane was re-blotted with an anti-actin antibody (clone AC-15, Sigma, Oakville, ON) which was expressed equally among the different samples separated on the gel. The other NSCLC cell line H226 was examined using the same approach (lower panel) and the results that were observed were similar to those observed with A549 cells. In this case, the EGF-induced degradation of the EGFR was even more pronounced when the cells were treated with the control for 48 h (lower panel, lanes 1-4). In the case of the cells treated with h16B5, no decrease in EGFR was seen (lower panel, lanes 5-8). This again showed that inhibition of sCLU with an antibody results in the maintenance of EGFR expression. Thus, these findings suggest that the cells would display increased sensitivity to EGFR inhibitors.

Figure 5:
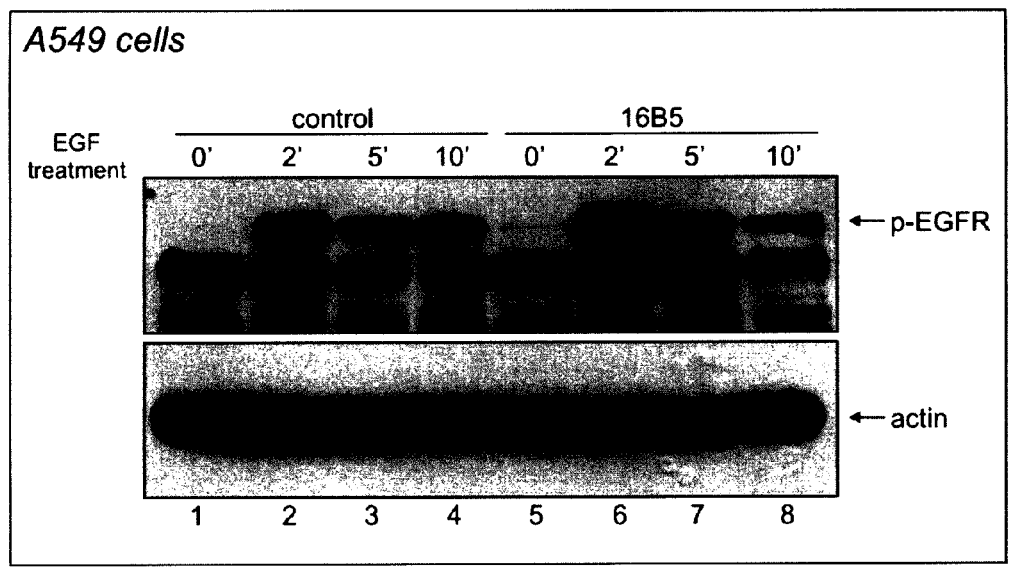
FIG. 5. Treatment of NSCLC cells with h16B5 results in increased EGFR phosphorylation. EGFR phosphorylation in the presence of control vehicle or h16B5 was measured using an phosphotyrosine-specific antibody in whole cell lysates prepared from either A549 or H226 cells.
Figure 5:
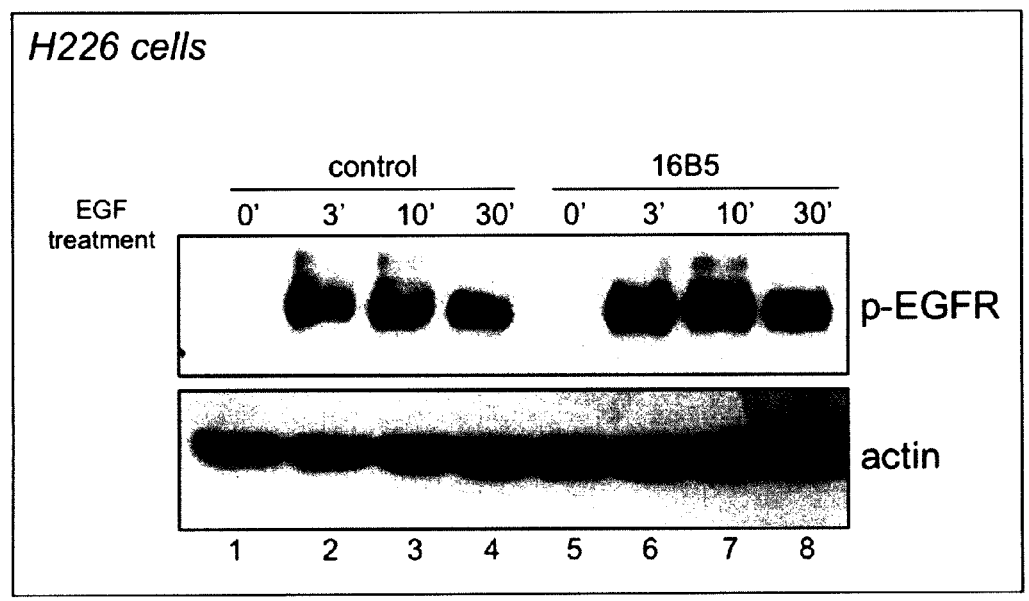
Figure 6:
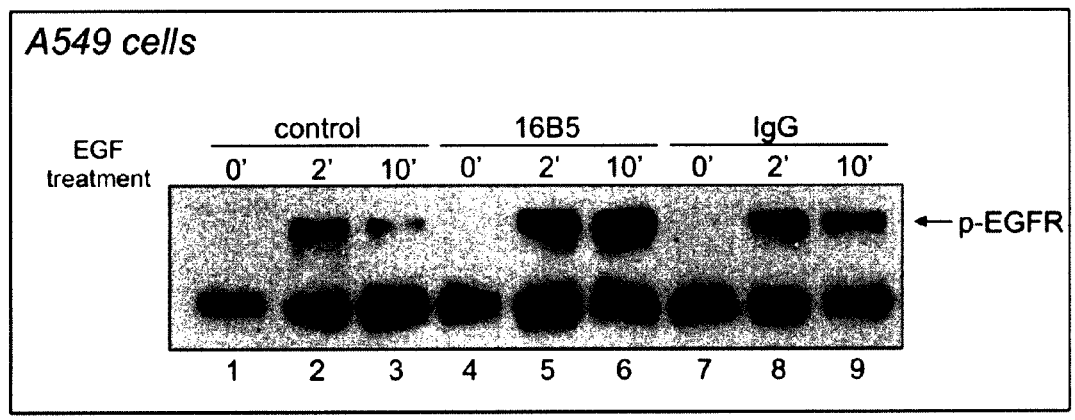
FIG. 6. Treatment of NSCLC cells with h16B5 results in increased EGFR phosphorylation. EGFR phosphorylation in the presence of control vehicle, h16B5 or a control IgG was measured using an phosphotyrosine-specific antibody in whole cell lysates prepared from either A549 or H226 cells.

The activation of EGFR in these cells was also examined. In this instance, the membranes were blotted with an antibody that interacts only with the tyrosine-phosphorylated form of the receptor. In A549 cells, no phosphorylation of EGFR was seen in the absence of EGF (see FIG. 5, upper panel, lane 1 and lane 5) as expected. However, when the cells were treated with EGF, the appearance of phosphorylated tyrosine residues was detected, even after 2 min (upper panel, lane 2 and lane 6). The cells treated with h16B5 for 48 h showed a higher amount of phosphorylated tyrosine residues on the EGFR compared to the cells that were left untreated. This difference in the phosphorylation of EGFR was reproduced in the H226 cells (see FIG. 5, lower panel, compare lanes 2-4 with lanes 6-8). As an additional control, the A549 cells were also treated with a control antibody for 48 h prior to being exposed to EGF (FIG. 6). Again, the change in the amount of phosphorylation of EGFR was only seen in the cells that were treated with h16B5 (compare lanes 2, 3 (control) and 8, 9 (IgG) with lanes 5, 6 (h16B5)).

Taken together our results show that blocking EMT in lung cancer cells influences the EGFR status in these cells. In particular, inhibition of sCLU EMT-inducing activity with a monoclonal antibody, such as h16B5, is one of the mechanisms by which the EGFR status in these cancer cells is altered. We showed that the lung cancer cells that were treated with h16B5 have increased expression of E-cadherin and are thus more epithelial. The combination of increased EGFR sensitivity with inhibition of EMT by blocking sCLU with an antibody, is expected to increase the efficacy of EGFR inhibitors. Finally, any cancer cells that express EGFR and undergo EMT, are expected to respond to an inhibitor of sCLU, such as a monoclonal antibody, in a similar manner to the lung cancer cells.

Example 4

A Method for Increasing the Sensitivity of Cancer Cells to EGFR Inhibitors in the Presence of h16B5

Inhibiting EMT in cancer cells by blocking sCLU with an anti-clusterin antibody leads to increased EGFR expression on the surface of the cells or increased EGFR phosphorylation or both. Thus inhibitors of EGFR are expected to have increased efficacy under conditions where EMT is inhibited with clusterin inhibitors.

For example, cancer cell lines are seeded in multiwell plates and when close to confluence, cells are treated with an anti-clusterin antibody (e.g., h16B5) to inhibit EMT. It may be useful to induce EMT, a priori, with known inducers such as sCLU, TGFβ, ligands of EGFR such as EGF or other similar molecules.

The EGFR inhibitor (e.g., monoclonal antibodies that block ligand binding to the receptor or that prevent the dimerization of EGFR, TK inhibitors, etc.) is also added to the wells either together with the anti-clusterin antibody or later (e.g., a few hours later). In some instance the EGFR inhibitor may be added to the wells prior to the anti-clusterin antibody.

The EGFR inhibitor may be added at different concentrations ranging from one fmol/L to one hundred micromol/L. To determine if the cytotoxicity of the EGFR inhibitors is increased when sCLU is inhibited with h16B5, the number of cells remaining is determined using standard protocols such as proliferation assays, invasion assays, apoptosis assays or migration assays. The cancer cells appropriate for this assay include EGFR inhibitor-resistant cancer cells or cancer cells that express wild type EGFR, EGFR containing activating mutations, EGFR gene amplifications and other situations where the status of EGFR might be altered.

The clusterin inhibitor and EGFR inhibitor combination may also be tested in vivo in well established models of cancer. For example, human cancer cell lines that express EGFR are injected in immunocompromised mice and allowed to grow until tumor xenografts are implanted. The animals are treated with an anti-clusterin antibody (e.g., 16B5, h16B5 or else) to block EMT in combination with a EGFR inhibitor (administered concurrently or sequentially). The growth of the tumors is monitored by various methods including direct size measurements with instruments such as a calliper. Other methods used to measure tumor growth might include fluorescence or bioluminescence in the case where the tumor cells are genetically modified to express fluorescent or bioluminescent molecules. In another instance, the tumors growth could be monitored using positron emission tomography (PET) or computed tomography (CT) scanning approaches. In these assays, The clusterin inhibitor and the EGFR inhibitor may be administered repeatedly by different routes including intravenous, subcutaneous, intra-muscular, intra-tumoral or orally. Typical doses would range from 1 microgram/kg to 100 mg/kg.

Based on the application of this method, it will be possible to demonstrate that treatment of an agent that blocks EMT, such as 16B5, h16B5 or else, in combination with an inhibitor of EGFR will result in an enhanced anti-tumor effect compared with either agent administered separately.

Figure 7:
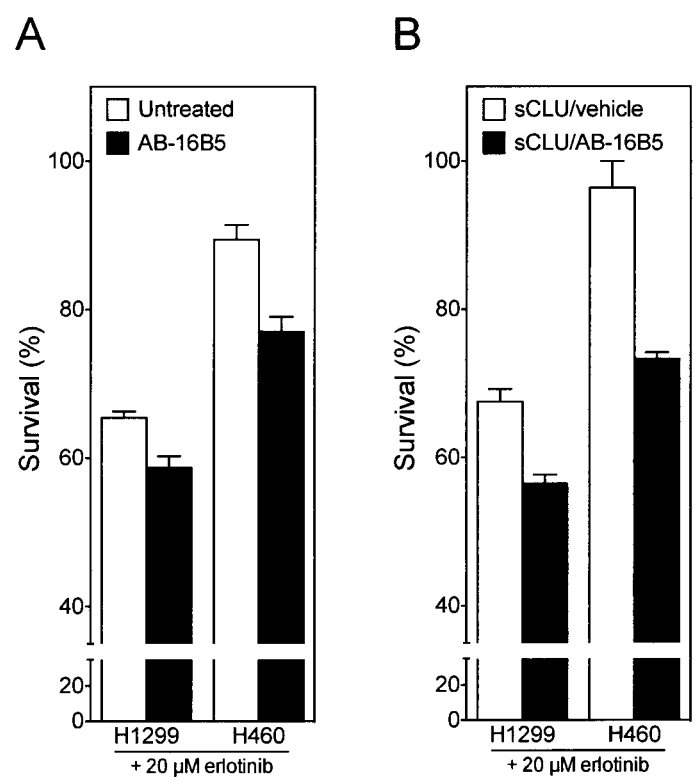
FIGS. 7A and B. Combination of h16B5 with erlotinib result in an enhanced anti-tumor effect. Survival of H1299 and H460 cancer cells was determined in the presence of a combination of h16B5 with erlotinib in the absence (A) or presence of recombinant clusterin (B).

In this example, we demonstrate that the response of cancer cells to EGFR inhibitors can be increased when administered in combination with an inhibitor of sCLU, such as h16B5. Two NCSLC cell lines, H1299 and H460, which are known to express wild type EGFR (Akashi et al., 2008), were treated with either sCLU (0.25 µg/ml), TGFβ (2 nM) or the combination of the two proteins for 48 h to stimulate EMT. Following this induction, the cells were treated with erlotinib (20 µM) for 96 h and the number of cells was determined using the CellTiter-Glo® Luminescent Cell Viability Assay (Promega, Madison, Wis.). As a control, additional cells were not induced with sCLU or TGFβ. As shown in FIG. 7A, H1299 cells were more sensitive to erlotinib than the H460 cells. Combination of erlotinib with h16B5 resulted in a further decrease in the cell number (10.2% and 13.8% less H1299 and H460 cells, respectively) indicating that blocking the activity of endogenously expressed sCLU (see FIG. 2) enhanced the ability of erlotinib to kill EGFR-positive lung cancer cells. We also compared the response to erlotinib in cells that were induced to undergo an EMT with either sCLU or TGFβ. As shown in FIG. 7B, stimulation of EMT did not change the responsiveness of the cells to erlotinib. However, the decrease in cell number was larger in the presence of h16B5 under these conditions compared to cells not undergoing EMT (16.1% and 24.0% for H1299 and H460 cells, respectively). This indicates that the increase of erlotinib-response is greater in cells when EMT is inhibited. It was noteworthy to observe that the increase in erlotinib responsiveness was greater in H460 cells, which are more resistant to this EGFR inhibitor. This last result illustrates the potential of sCLU inhibition with h16B5 as a strategy to treat lung cancer patients who become resistant to EGFR inhibitors.

Example 5

Pharmaceutical Combination for Use in Other Cancer Indications

The breast cancer cell line MDA-MB-231, which is known to be triple negative (i.e., lack of expression of the estrogen and progesterone receptors, and absence of HER2-expression) or basal-like was treated with an anti-clusterin antibody in combination with gefitinib or with gefitinib alone. Cell growth was measured over a period of several days by standard assays.

This experiment shows that the combination of the anti-clusterin antibody with gefitinib is more effective at inhibiting tumor cell growth that gefitinib alone (data not shown).

Other clusterin inhibitors and/or EGFR inhibitors combination may be tested using similar techniques as those described in Examples 1-5.

```
                        SEQUENCE LISTING

SEQ ID NO.: 1
16B5 CDRH1: GFNIKDIYMH

SEQ ID NO.: 2
16B5 CDRH2: RIDPAYGNTKYDPKFQG

SEQ ID NO.: 3
16B5 CDRH3: RYDTAMDY

SEQ ID NO.: 4
16B5 CDRL1: KSSQSLLNSRTRKNYLA

SEQ ID NO.: 5
16B5 CDRL2: WASTRES

SEQ ID NO.: 6
16B5 CDRL3: KQSYNLWT

SEQ ID NO.: 7
h16B5 Humanized heavy chain variable region
QVQLVQSGAEVKKPGATVKISCKVSGFNIKDIYMHWVQQAPGKGLEWMGRIDPAYGN
TKYDPKFQGRVTITADTSTDTAYMELSSLRSEDTAVYYCARRYDTAMDYWGQGTLVTVSS SEQ ID NO.: 8
h16B5 Humanized light chain variable region
DIVMTQSPDSLAVSLGERATINCKSSQSLLNSRTRKNYLAWYQQKPGQPPKLLIYWAST
RESGVPDRFSGSGSGTDFTLTISSLQAEDVAVYYCKQSYNLWTFGQGTKLEIK SEQ ID NO.: 9
Complete heavy chain immunoglobulin sequences for h16B5
QVQLVQSGAEVKKPGATVKISCKVSGFNIKDIYMHWVQQAPGKGLEWMGRIDPAYGN
TKYDPKFQGRVTITADTSTDTAYMELSSLRSEDTAVYYCArRYDTAMDYwgqgtlvtvsSAS
TKGPSVFPLAPCSRSTSESTAALGCLVKDYFPEPVTVSWNSGALTSGVHTFPAVLQSS
GLYSLSSVVTVPSSNFGTQTYTCNVDHKPSNTKVDKTVERKCCVECPPCPAPPVAGPS
VFLFPPKPKDTLMISRTPEVTCVVVDVSHEDPEVQFNWYVDGVEVHNAKTKPREEQFN
STFRVVSVLTVVHQDWLNGKEYKCKVSNKGLPAPIEKTISKTKGQPREPQVYTLPPSRE
EMTKNQVSLTCLVKGFYPSDIAVEWESNGQPENNYKTTPPMLDSDGSFFLYSKLTVDK
SRWQQGNVFSCSVMHEALHNHYTQKSLSLSPGK SEQ ID NO.: 10
Complete light chain immunoglobulin sequences for h16B5
DIVMTQSPDSLAVSLGERATINCKSSQSLLNSRTRKNYLAWYQQKPGQPPKLLIYWAST
RESGVPDRFSGSGSGTDFTLTISSLQAEDVAVYYCKQSYNLWTFGQGTKLEIKVAAPS
VFIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC

SEQ ID NO.: 11
21B12 CDRH1: GYTFTNYGMH

SEQ ID NO.: 12
21B12 CDRH2: WINTYTGEPTYADDFKG

SEQ ID NO.: 13
21B12 CDRH3: DGFLYFFDY

SEQ ID NO.: 14
21B12 CDRL1: KSSQSLLYSSNQKNYLA

SEQ ID NO.: 15
21B12 CDRL2: WASTRES

SEQ ID NO.: 16
21B12 CDRL3: QQYYIYPRT
```

SEQUENCE LISTING

SEQ ID NO.: 17
h21B12 Humanized heavy chain variable region
QVQLVQSGSELKKPGASVKVSCKASGYTFTNYGMHWVRQAPGQGLEWMGWINTYTG
EPTYADDFKGRFVFSLDTSVSTAYLQISSLKAEDTAVYYCARdGFLYFFDYWGQGTLVT
VSS SEQ ID NO.: 18
h21B12 Humanized light chain variable region
DIVMTQSPDSLAVSLGERATINCKSSQSLLYSSNQKNYLAWYQQKPGQPPKLLIYWAST
RESGVPDRFSGSGSGTDFTLTISSLQAEDVAVYYCQQYYIYPRTFGQGTKLEIK SEQ ID NO.: 19
Complete heavy chain immunoglobulin sequences for h21B12
QVQLVQSGSELKKPGASVKVSCKASGYTFTNYGMHWVRQAPGQGLEWMGWINTYTG
EPTYADDFKGRFVFSLDTSVSTAYLQISSLKAEDTAVYYCARdGFLYFFDYWGQGTLVT
VSSASTKGPSVFPLAPCSRSTSESTAALGCLVKDYFPEPVTVSWNSGALTSGVHTFPA
VLQSSGLYSLSSVVTVPSSNFGTQTYTCNVDHKPSNTKVDKTVERKCCVECPPCPAPP
VAGPSVFLFPPKPKDTLMISRTPEVTCVVVDVSHEDPEVQFNWYVDGVEVHNAKTKPR
EEQFNSTFRVVSVLTVVHQDWLNGKEYKCKVSNKGLPAPIEKTISKTKGQPREPQVYTL
PPSREEMTKNQVSLTCLVKGFYPSDIAVEWESNGQPENNYKTTPPMLDSDGSFFLYSK
LTVDKSRWQQGNVFSCSVMHEALHNHYTQKSLSLSPGK SEQ ID NO.: 20
Complete light chain immunoglobulin sequences for h21B12
DIVMTQSPDSLAVSLGERATINCKSSQSLLYSSNQKNYLAWYQQKPGQPPKLLIYWAST
RESGVPDRFSGSGSGTDFTLTISSLQAEDVAVYYCQQYYIYPRTFGQGTKLEIKRTVAA
PSVFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC SEQ ID NO.: 21
Complete nucleotide sequence of the heavy chain of h16B5
ATGGACTGGACCTGGCGGATCCTGTTCCTGGTGGCCGCTGCTACCGGCACCCACG
CCCAGGTGCAGCTGGTGCAGTCTGGCGCCGAGGTGAAGAAGCCTGGCGCCACCG
TCAAGATCAGCTGCAAGGTGTCCGGCTTCAACATCAAGGACATCTACATGCACTGG
GTGCAGCAGGCTCCAGGCAAGGGACTGGAGTGGATGGGCCGGATCGACCCTGCC
TACGGCAACACCAAGTACGACCCTAAGTTCCAGGGCCGGGTGACCATCACCGCCG
ACACCTCCACCGACACCGCCTACATGGAACTGTCCTCCCTGCGGTCCGAGGACAC
CGCCGTGTACTACTGCGCCCGGAGATACGACACCGCCATGGATTACTGGGGCCAG
GGCACCCTGGTGACCGTGTCCTCCGCTTCCACCAAGGGCCCATCGGTCTTCCCCC
TGGCGCCCTGCTCCAGGAGCACCTCCGAGAGCACAGCGGCCCTGGGCTGCCTGG
TCAAGGACTACTTCCCCGAACCGGTGACGGTGTCGTGGAACTCAGGCGCTCTGAC
CAGCGGCGTGCACACCTTCCCAGCTGTCCTACAGTCCTCAGGACTCTACTCCCTCA
GCAGCGTGGTGACCGTGCCCTCCAGCAACTTCGGCACCCAGACCTACACCTGCAA
CGTAGATCACAAGCCCAGCAACACCAAGGTGGACAAGACAGTTGAGCGCAAATGTT
GTGTCGAGTGCCCACCGTGCCCAGCACCACCTGTGGCAGGACCGTCAGTCTTCCT
CTTCCCCCCAAAACCCAAGGACACCCTCATGATCTCCCGGACCCCTGAGGTCACGT
GCGTGGTGGTGGACGTGAGCCACGAAGACCCCGAGGTCCAGTTCAACTGGTACGT
GGACGGCGTGGAGGTGCATAATGCCAAGACAAAGCCACGGGAGGAGCAGTTCAAC
AGCACGTTCCGTGTGGTCAGCGTCCTCACCGTTGTGCACCAGGACTGGCTGAACG
GCAAGGAGTACAAGTGCAAGGTCTCCAACAAAGGCCTCCCAGCCCCCATCGAGAA
AACCATCTCCAAAACCAAAGGGCAGCCCCGAGAACCACAGGTGTACACCCTGCCC
CCATCCCGGGAGGAGATGACCAAGAACCAGGTCAGCCTGACCTGCCTGGTCAAAG
GCTTCTACCCCAGCGACATCGCCGTGGAGTGGGAGAGCAATGGGCAGCCGGAGA
ACAACTACAAGACCACACCTCCCATGCTGGACTCCGACGGCTCCTTCTTCCTCTAC
AGCAAGCTCACCGTGGACAAGAGCAGGTGGCAGCAGGGGAACGTCTTCTCATGCT
CCGTGATGCATGAGGCTCTGCACAACCACTACACGCAGAAGAGCCTCTCCCTGTCT
CCGGGTAAATGA SEQ ID NO. : 22
Complete nucleotide sequence of the heavy chain of h21B12
ATGGACTGGACCTGGCGGATCCTGTTTCTGGTGGCCGCTGCTACCGGCACACACG
CCCAGGTGCAGCTGGTGCAGTCCGGCTCCGAGCTGAAGAAACCTGGCGCCTCCGT
GAAGGTGTCCTGCAAGGCCTCCGGCTACACCTTCACCAACTACGGCATGCACTGG
GTGCGCCAGGCACCTGGACAGGGACTGGAATGGATGGGCTGGATCAACACCTACA
CCGGCGAGCCTACCTACGCCGACGACTTCAAGGGCAGATTCGTGTTCTCCCTGGA
CACCTCCGTGTCCACCGCCTACCTGCAGATCTCCTCCCTGAAGGCCGAGGACACC
GCCGTGTACTACTGCGCCAGGGACGGCTTCCTGTACTTCTTCGACTACTGGGGCC
AGGGCACCCTGGTGACCGTGTCCTCTGCCTCCACCAAGGGCCCTTCCGTGTTCCC
TCTGGCCCCTTGCTCCCGGTCCACCTCTGAGTCTACCGCCGCTCTGGGCTGCCTG
GTGAAGGACTACTTCCCTGAGCCTGTGACAGTGTCCTGGAACTCTGGCGCCCTGA
CCTCTGGCGTGCACACCTTCCCTGCCGTGCTGCAGTCCTCCGGCCTGTACTCCCT
GTCCTCCGTGGTGACAGTGCCTTCCTCCAACTTCGGCACCCAGACCTACACCTGCA
ACGTGGACCACAAGCCTTCCAACACCAAGGTGGACAAGACCGTGGAGCGGAAGTG
CTGCGTGGAGTGCCCTCCTTGTCCTGCTCCTCCTGTGGCTGGCCCTAGCGTGTTC
CTGTTCCCTCCTAAGCCTAAGGACACCCTGATGATCTCCCGGACCCCTGAAGTGAC
CTGCGTGGTGGTGGACGTGTCCCACGAGGACCCTGAGGTGCAGTTCAATTGGTAC

SEQUENCE LISTING

```
GTGGACGGCGTGGAGGTGCACAACGCCAAGACCAAGCCTCGGGAGGAACAGTTC
AACTCCACCTTCCGGGTGGTGTCCGTGCTGACCGTGGTGCACCAGGACTGGCTGA
ACGGCAAAGAATACAAGTGCAAGGTGTCCAACAAGGGCCTGCCTGCCCCTATCGA
AAAGACCATCTCTAAGACCAAGGGCCAGCCTCGCGAGCCTCAGGTGTACACCCTG
CCTCCCTCCCGCGAGGAAATGACCAAGAACCAGGTGTCCCTGACCTGTCTGGTGA
AGGGCTTCTACCCTTCCGATATCGCCGTGGAGTGGGAGTCTAACGGCCAGCCTGA
GAACAACTACAAGACCACCCCTCCTATGCTGGACTCCGACGGCTCCTTCTTCCTGT
ACAGCAAGCTGACAGTGGACAAGTCCCGGTGGCAGCAGGGCAACGTGTTCTCCTG
CTCCGTGATGCACGAGGCCCTGCACAACCACTACACCCAGAAGTCCCTGTCCCTGT
CTCCTGGCAAGTGA

SEQ ID NO.: 23
Complete nucleotide sequence of the light chain of h16B5
ATGGTGCTGCAGACCCAGGTGTTCATCTCCCTGCTGCTGTGGATCTCCGGCGCCTA
CGGCGACATCGTGATGACCCAGTCCCCCGACTCCCTGGCCGTGTCCCTGGGCGAG
AGAGCCACCATCAACTGCAAGTCCTCCCAGTCCCTGCTGAACTCCCGGACCCGGA
AGAACTACCTGGCCTGGTATCAGCAGAAGCCTGGCCAGCCTCCTAAGCTGCTGATC
TACTGGGCCTCCACCCGGGAGTCCGGCGTGCCTGACCGGTTCTCCGGCTCCGGC
AGCGGCACCGACTTCACCCTGACCATCAGCTCCCTGCAGGCCGAGGACGTGGCCG
TGTACTACTGCAAGCAGTCCTACAACCTGTGGACTTTCGGCCAGGGCACCAAGCTG
GAGATCAAGCGGACTGTGGCTGCACCATCTGTCTTCATCTTCCCGCCATCTGATGA
GCAGTTGAAATCTGGAACTGCCTCTGTTGTGTGCCTGCTGAATAACTTCTATCCCAG
AGAGGCCAAAGTACAGTGGAAGGTGGATAACGCCCTCCAATGGGTAACTCCCAG
GAGAGTGTCACAGAGCAGGACAGCAAGGACAGCACCTACAGCCTCAGCAGCACCC
TGACGCTGAGCAAAGCAGACTACGAGAAACACAAAGTCTACGCCTGCGAAGTCACC
CATCAGGGCCTGAGCTCGCCCGTCACAAAGAGCTTCAACAGGGGAGAGTGTTAG SEQ ID NO.: 24
Complete nucleotide sequence of the light chain of h21B12
ATGGTGCTGCAGACCCAGGTGTTCATCTCCCTGCTGCTGTGGATCTCTGGCGCCTA
CGGCGACATCGTGATGACCCAGTCCCCCGACTCTCTGGCTGTGTCCCTGGGCGAG
CGGGCCACCATCAACTGCAAGTCCTCCCAGTCCCTGCTGTACTCCTCCAACCAGAA
GAACTACCTGGCCTGGTATCAGCAGAAGCCTGGCCAGCCTCCTAAGCTGCTGATCT
ACTGGGCCTCCACCCGGGAATCTGGCGTGCCTGACCGGTTCTCCGGCTCTGGCTC
CGGCACCGACTTCACCCTGACCATCAGCTCCCTGCAGGCCGAGGACGTGGCCGTG
TACTACTGCCAGCAGTACTACATCTACCCTCGGACCTTCGGCCAGGGCACCAAGCT
GGAAATCAAGCGGACCGTGGCCGCTCCTTCCGTGTTCATCTTCCCCCCTTCCGACG
AGCAGCTGAAGTCCGGCACCGCCTCTGTGGTGTGCCTGCTGAACAACTTCTACCC
CCGGGAGGCCAAGGTGCAGTGGAAGGTGGACAACGCCCTGCAGTCCGGCAACTC
CCAGGAATCCGTCACCGAGCAGGACTCCAAGGACTCTACCTACTCCCTGTCCTCCA
CCCTGACCCTGTCCAAGGCCGACTACGAGAAGCACAAGGTGTACGCCTGCGAAGT
GACCCACCAGGGCCTGTCCTCTCCCGTGACCAAGTCCTTCAACCGGGGCGAGTGC
TGA SEQ ID NO.: 25 (murine 16B5 VL)
DIVMSQSPSSLAVSAGEKVTMSCKSSQSLLNSRTRKNYLAWYQQKPGQSPKLLIY**WA
STRESGVPDRFTGSGSGTDFTLTISSVQAEDLAVYYCKQSYNLWT**FGGGTKLEFK SEQ ID NO.: 26 (h16B5 VL consensus1)
DIVMXQSPXSLAVSXGEXXTXXCKSSQSLLNSRTRKNYLAWYQQKPGQXPKLLIY**WA
STRESGVPDRFXGSGSGTDFTLTISSXQAEDXAVYYCKQSYNLW**TFGXGTKLEXK;
X is an amino acid substitution in comparison with a corresponding
amino acid in the polypeptide set forth in SEQ ID NO.: 25.

SEQ ID NO.: 27 (h16B5 VL consensus2)
DIVMX$_{a1}$QSPX$_{a2}$SLAVSX$_{a3}$GEX$_{a4}$X$_{a5}$TX$_{a6}$X$_{a7}$CKSSQSLLNSRTRKNYLAWYQQKPGQX$_{a8}$
PKLLIYWASTRESGVPDRFX$_{a9}$GSGSGTDFTLTISSX$_{a10}$QAEDX$_{a11}$AVYYC**KQSYNL-
WT**FGX$_{a12}$GTKLEX$_{a13}$K
X$_{a1}$ is a neutral hydrophilic amino acid such as for example, T or S;
X$_{a2}$ is D or S;
X$_{a3}$ is an hydrophobic amino acid such as for example, L or A;
X$_{a4}$ is a basic amino acid such as for example R or K;
X$_{a5}$ is an hydrophobic amino acid such as for example A or V;
X$_{a6}$ is an hydrophobic amino acid as for example I or M;
X$_{a7}$ is N or S;
X$_{a8}$ is P or S;
X$_{a9}$ is a neutral hydrophilic amino acid such as for example S or T;
X$_{a10}$ is an hydrophobic amino acid such as for example L or V;
X$_{a11}$ is an hydrophobic amino acid such as for example V or L;
X$_{a12}$ is Q or G and;
X$_{a13}$ is I or F.
```

SEQUENCE LISTING

SEQ ID NO.: 28 (h16B5 VL consensus3)
DIVMX$_{a1}$QSPX$_{a2}$SLAVSX$_{a3}$GEX$_{a4}$X$_{a5}$TX$_{a6}$X$_{a7}$CKSSQSLLNSRTRKNYLAWYQQKPGQX$_{a8}$
PKLLIYWASTRESGVPDRFX$_{a9}$GSGSGTDFTLTISSX$_{a10}$QAEDX$_{a11}$AVYYC**KQSYNL-
WTF**GX$_{a12}$GTKLEX$_{a13}$K
X$_{a1}$ is T or S; Xag is D or S; X$_{a3}$ is L or A; X$_{a4}$ is R or K; X$_{a5}$ is A or
V; X$_{a6}$ is I or M; X$_{a7}$ is N or S; X$_{a8}$ is P or S; X$_{a9}$ is S or T; X$_{a10}$ is L
or V; X$_{a11}$ is V or L; X$_{a12}$ is Q or G and; X$_{a13}$ is I or F.

SEQ ID NO.: 29 (murine 16B5 VH)
EVQLQQSGAELVKPGASVRLSCTTSGFNIKDIYMHWVKQRPEQGLEWIG**RIDPAYGNT
KYDPKFQGKATITADTSSNTAYLQLSSLTSEDTAVYYCARRYDTAMDY**WGQGTSVTVSS SEQ ID NO.: 30 (h16B5 VH consensus1)
XVQLXQSGAEXXKPGAXVXXSCXXSGFNIKDIYMHWVXQXPXXGLEWXG**RIDPAYGN
TKYDPKFQGXXTITADTSXXTAYXXLSSLXSEDTAVYYCARRYDTAMDY**WGQGTXVTVSS;
X is an amino acid substitution in comparison with a corresponding amino
acid in the polypeptide set forth in SEQ ID NO.: 29.

SEQ ID NO.: 31 (h16B5 VH consensus2)
X$_{b1}$VQLX$_{b2}$QSGAEX$_{b3}$X$_{b4}$KPGAX$_{b5}$VX$_{b6}$X$_{b7}$SCX$_{b8}$X$_{b9}$SGFNIKDIYMHWVX$_{b10}$QX$_{b11}$PX$_{b12}$X$_{b13}$
GLEWX$_{b14}$GRIDPAYGNTKYDPKFQGX$_{b15}$X$_{b16}$TITADTSX$_{b17}$X$_{b18}$TAYX$_{b19}$X$_{b20}$LSSLX$_{b21}$S
EDTAVYYCARRYDTAMDYWGQGTX$_{b22}$VTVSS;
X$_{b1}$ is Q or E;
X$_{b2}$ is V or Q;
X$_{b3}$ is an hydrophobic amino acid such as for example V or L;
X$_{b4}$ is K or V;
X$_{b5}$ is a neutral hydrophilic amino acid such as for example T or S;
X$_{b6}$ is a basic amino acid such as for example K or R;
X$_{b7}$ is an hydrophobic amino acid such as for example I or L;
X$_{b8}$ is K or T;
X$_{b9}$ is V or T;
X$_{b10}$ is a basic amino acid such as for example Q or K;
X$_{b11}$ is A or R;
X$_{b12}$ is G or E;
X$_{b13}$ is a basic amino acid such as for example K or Q;
X$_{b14}$ is an hydrophobic amino acid such as for example M or I;
X$_{b15}$ is a basic amino acid such as for example R or K;
X$_{b16}$ is an hydrophobic amino acid such as for example V or A;
X$_{b17}$ is a neutral hydrophilic amino acid such as for example T or S;
X$_{b18}$ is for example D or N;
X$_{b19}$ is an hydrophobic amino acid such as for example M or L;
X$_{b20}$ is E or Q;
X$_{b21}$ is R or T and;
X$_{b22}$ is L or S.

SEQ ID NO.: 32 (h16B5 VH consensus3)
X$_{b1}$VQLX$_{b2}$QSGAEX$_{b3}$X$_{b4}$KPGAX$_{b5}$VX$_{b6}$X$_{b7}$SCX$_{b8}$X$_{b9}$SGFNIKDIYMHWVX$_{b10}$QX$_{b11}$PX$_{b12}$X$_{b13}$
GLEWX$_{b14}$GRIDPAYGNTKYDPKFQGX$_{b15}$X$_{b16}$TITADTSX$_{b17}$X$_{b18}$TAYX$_{b19}$X$_{b20}$LSSLX$_{b21}$S
EDTAVYYCARRYDTAMDYWGQGTX$_{b22}$VTVSS;
X$_{b1}$ is Q or E; X$_{b2}$ is V or Q; X$_{b3}$ is V or L; X$_{b4}$ is K or V; X$_{b5}$ is T or S;
X$_{b6}$ is K or R; X$_{b7}$ is I or L; X$_{b8}$ is K or T; X$_{b9}$ is V or T; X$_{b10}$ is Q or K;
X$_{b11}$ is A or R; X$_{b12}$ is G or E; X$_{b13}$ is K or Q; X$_{b14}$ is M or I; X$_{b15}$ is R
or K; X$_{b16}$ is V or A; <<X$_{b17}$ is T or S; X$_{b18}$ is D or N; X$_{b19}$ is M or
L; X$_{b20}$ is E or Q; X$_{b21}$ is R or T and; X$_{b22}$ is L or S.

SEQ ID NO.: 33 (murine 21B12 VL)
DIVMSQSPSSLAVSVGEKVTMSCKSSQSLLYSSNQKNYLAWYQQRPGQSPKLLIYWAS
TRESGVPDRFTGSGSGTDFTLTISSVKAEDLAVYYCQQYYIYPRTFGGGTKLEIK SEQ ID NO.: 34 (h21B12 VL consensus1)
DIVMX$_{c}$QSPXSLAVSXGEXXTXXCKSSQSLLYSSNQKNYLAWYQQXPGQXPKLLIY**WA
STRESGVPDRFXGSGSGTDFTLTISSXXAEDXAVYYCQQYYIYPRT**FGXGTKLEIK
X is an amino acid substitution in comparison with a corresponding amino
acid in the polypeptide set forth in SEQ ID NO.: 33.

SEQ ID NO.: 35 (h21B12 VL consensus2)
DIVMX$_{c1}$QSPX$_{c2}$SLAVSX$_{c3}$GEX$_{c4}$X$_{c5}$TX$_{c6}$X$_{c7}$CKSSQSLLYSSNQKNYLAWYQQX$_{c8}$PGQX$_{c9}$
PKLLIYWASTRESGVPDRFX$_{c10}$GSGSGTDFTLTISSX$_{c11}$X$_{c12}$AEDX$_{c13}$AVYYC**QQYYIYP
RTF**GX$_{c14}$GTKLEIK;
X$_{c1}$ is a neutral hydrophilic amino acid such as for example T or S;
X$_{c2}$ is D or S;
X$_{c3}$ is an hydrophobic amino acid such as for example L or V;
X$_{c4}$ is a basic amino acid such as for example R or K;
X$_{c5}$ is an hydrophobic amino acid such as for example A or V;
X$_{c6}$ is an hydrophobic amino acid such as for example I or M;
X$_{c7}$ is N or S;

SEQUENCE LISTING $X_{c8}$ is a basic amino acid such as for example K or R;
$X_{c9}$ is P or S;
$X_{c10}$ is a neutral hydrophilic amino acid such as for example S or T;
$X_{c11}$ is an hydrophobic amino acid such as for example L or V;
$X_{c12}$ is a basic amino acid such as for example Q or K;
$X_{c13}$ is an hydrophobic amino acid such as for example V or L and;
$X_{c14}$ is Q or G.

SEQ ID NO.: 36 (h21B12 VL consensus3)
DIVMX$_{c1}$QSPX$_{c2}$SLAVSX$_{c3}$GEX$_{c4}$X$_{c5}$TX$_{c6}$X$_{c7}$CKSSQSLLYSSNQKNYLAWYQQX$_{c8}$PGQX$_{c9}$
PKLLIYWASTRESGVPDRFX$_{c10}$GSGSGTDFTLTISSX$_{c11}$X$_{c12}$AEDX$_{c13}$AVYYC**QQYYIYP
RTF**GX$_{c14}$GTKLEIK;
$X_{c1}$ is T or S; $X_{c2}$ is D or S; $X_{c3}$ is L or V; $X_{c4}$ is R or K; $X_{c5}$ is A or V;
$X_{c6}$ is I or M; $X_{c7}$ is N or S; $X_{c8}$ is K or R; $X_{c9}$ is P or S; $X_{c10}$ is S or T;
$X_{c11}$ is L or V; $X_{c12}$ is Q or K; $X_{c13}$ is V or L and; $X_{c14}$ is Q or G.

SEQ ID NO.: 37 (murine 21B12 VH)
QIQLVQSGPELKKPGETVKISCKASGYTFTNYGMHWVKQAPGKGLKWMGWINTYTGE
PTYADDFKGRFAFSLETSASTAYLQINNLKNEDTATYFCARDGFLYFFDYWGQGTTLTVSS SEQ ID NO.: 38 (h21B12 VH consensus1)
QXQLVQSGXELKKPGXXVKXSCKASGYTFTNYGMHWVXQAPGXGLXWMG**WINTYTG
EPTYADDFKGRFXFSLXTSXSTAYLQIXXLKXEDTAXYXCARDGFLYFFDY**WGQGTXXTVSS
X is an amino acid substitution in comparison with a corresponding amino acid in the polypeptide set forth in SEQ ID NO.: 37.

SEQ ID NO.: 39 (h21B12 VH consensus2)
QX$_{d1}$QLVQSGX$_{d2}$ELKKPGX$_{d3}$X$_{d4}$VKX$_{d5}$SCKASGYTFTNYGMHWVX$_{d6}$QAPGX$_{d7}$GLX$_{d8}$W
MGWINTYTGEPTYADDFKGRFX$_{d9}$FSLX$_{d10}$TSX$_{d11}$STAYLQIX$_{d12}$X$_{d13}$LKX$_{d14}$EDTAX$_{d15}$YX$_{d16}$
CARDGFLYFFDYWGQGTX$_{d17}$X$_{d18}$TVSS;
$X_{d1}$ is an hydrophobic amino acid such as for example V or I;
$X_{d2}$ is S or P;
$X_{d3}$ is A or E;
$X_{d4}$ is a neutral hydrophilic amino acid such as for example S or T;
$X_{d5}$ is an hydrophobic amino acid such as for example V or I;
$X_{d6}$ is a basic amino acid such as for example R or K;
$X_{d7}$ is a basic amino acid such as for example Q or K;
$X_{d8}$ is E or K;
$X_{d9}$ is an hydrophobic amino acid such as for example V or A;
$X_{d10}$ is an acidic amino acid such as for example D or E;
$X_{d11}$ is an hydrophobic amino acid such as for example V or A;
$X_{d12}$ is S or N;
$X_{d13}$ is S or N;
$X_{d14}$ is A or N;
$X_{d15}$ is V or T;
$X_{d16}$ is an aromatic amino acid such as for example Y or F;
$X_{d17}$ is L or T and;
$X_{d18}$ is hydrophobic amino acid such as for example V or L.

SEQ ID NO.: 40 (h21B12 VH consensus3)
QX$_{d1}$QLVQSGX$_{d2}$ELKKPGX$_{d3}$X$_{d4}$VKX$_{d5}$SCKASGYTFTNYGMHWVX$_{d6}$QAPGX$_{d7}$GLX$_{d8}$W
MGWINTYTGEPTYADDFKGRFX$_{d9}$FSLX$_{d10}$TSX$_{d11}$STAYLQIX$_{d12}$X$_{d13}$LKX$_{d14}$EDTAX$_{d15}$YX$_{d16}$
CARDGFLYFFDYWGQGTX$_{d17}$X$_{d18}$TVSS;
$X_{d1}$ is V or I; $X_{d2}$ is S or P; $X_{d3}$ is A or E; $X_{d4}$ is S or T; $X_{d5}$ is V or I;
$X_{d6}$ is R or K; $X_{d7}$ is Q or K; $X_{d8}$ is E or K; $X_{d9}$ is V or A; $X_{d10}$ is D or E;
$X_{d11}$ is V or A; $X_{d12}$ is S or N; $X_{d13}$ is S or N; $X_{d14}$ is A or N; $X_{d15}$ is V
or T; <<$X_{d16}$ is Y or F; $X_{d17}$ is L or T and; $X_{d18}$ is V or L.

SEQ ID NO.: 41 (human model of 16B5VL)
DIVMTQSPDSLAVSLGERATINCKSSQSVLYSSNSKNYLAWYQQKPGQPPKLLIYWAST
RESGVPDRFSGSGSGTDFTLTISSLQAEDVAVYYCQQYYSTPYSFGQGTKLEIK SEQ ID NO.: 42 (human model of 16B5VH)
QVQLVQSGAEVKKPGATVKISCKVSGYTFTDYYMHWVQQAPGKGLEWMGLVDPEDG
ETIYAEKFQGRVTITADTSTDTAYMELSSLRSEDTAVYYCARIPLFGRDHWGQGTLVTVSR SEQ ID NO.: 43 (human model of 21B12VL)
DIVMTQSPDSLAVSLGERATINCKSSQSVLYSSNSKNYLAWYQQKPGQPPKLLIYWAST
RESGVPDRFSGSGSGTDFTLTISSLQAEDVAVYYCQQYYSTPYS FGQGTKLEIK SEQ ID NO.: 44 (human model of 21B12VH)
QVQLVQSGSELKKPGASVKVSCKASGYTFTSYAMNWVRQAPGQGLEWMGWINTNTG
NPTYAQGFTGRVFSLDTSVSTAYLQISSLKAEDTAVYYCARDWGQGTLVTVSSVATID
ENWFDP

SEQUENCE LISTING

```
SEQ ID NO.: 45
16B5 CDRH1 (shorter version): GFNIKDIY

SEQ ID NO.: 46
16B5 CDRH2 (shorter version): IDPAYGNT

SEQ ID NO.: 47
16B5 CDRH3: ARRYDTAMDY

SEQ ID NO.: 48
16B5 CDRL1 (shorter version): QSLLNSRTRKNY

SEQ ID NO.: 49
16B5 CDRL2 (shorter version): WAS

SEQ ID NO.: 50
16B5 CDRL3: KQSYNLWT

SEQ ID NO.: 51
21B12 CDRH1: GYTFTNYG

SEQ ID NO.: 52
21B12 CDRH2: INTYTGEP

SEQ ID NO.: 53
21B12 CDRH3: X3X4DGFLYFFDY
X3 is A;
X4 is R;
or X3 and X4 are outside the CDRH3

SEQ ID NO.: 54
21B12 CDRL1: QSLLYSSNQKNY

SEQ ID NO.: 55
21B12 CDRL2: WAS

SEQ ID NO.: 56
21B12 CDRL3: QQYYIYPRT

SEQ ID NO: 57
GAGCAGAGCGCTATAAATACG

SEQ ID NO: 58
CACGGTCTCCATAAATTTAGG

SEQ ID NO: 59
TTGCGGCCGCAATACAATGAGCTGCGTGTGGC

SEQ ID NO: 60
GACTCATCGTACTCCTGCTTGCTG

SEQ ID NO.: 61
clusterin antisense: 5'-CAGCAGCAGAGTCTTCATCAT-3'

SEQ ID NO.: 62 (20E11 variable light chain)
DIVLTLSPASLAVSLGQRATISCRASQSVNSSNYSYMHWYQQKPGQPPKLLIKYASNLESGVP
ARFSGSGSGTHFTLNIHPVEEEDTATYYCQHSWEIPWTFGGGTKLEIK SEQ ID NO.: 63 (20E11 variable heavy chain)
QIQLVQSGPELKKPGETVKISCKASGYTFTDYSMHWVKQAPGKGLKWMGWINTETGEPTYA
DDFKGRFAFSLETSASTAYLQINNLKNEDTATYFCARTGSSGYFDCWGQGTTLTVSS SEQ ID NO.: 64 (11E2 variable light chain Gr1)
ENVLTQSPAIMSASPGEKVTMTCSASSSVSYMHWYQQKSSTSPKLWIYDTSKLASGVPGRFS
GSGSGNSYSLTISSMEAEDVATYYCFQGSGYPFTFGSGTKLEIK SEQ ID NO.: 65 (11E2 variable light chain GR2)
DIQMTQSPSSLSASLGGKVTITCKASQDINKYIAWYQHKPGKGPRLLIHYTSTLQPGIPSRFS
GSGSGRDYSFSISNLEPEDIATYYCLQYDNLLRTFGGGTKLEIK SEQ ID NO.: 66 (11E2 variable heavy chain)
EVQLQQSGPELEKPGASVKISCKASGYSFTGYNMNWVKQNNGKSLEWIGNIDPYYGTPNYN
QKFKGKATLTVDKSSSTAYMQLKSLTSEDSAVYYCALNSLLRLNAMDYWGQGTSVTVSS
```

SEQUENCE LISTING

SEQ ID NO.: 67 (16C11 variable heavy chain)
EVQLQQSGPELGKPGASVKISCKASGYSFTGYNMYWVKQSHRKSLEWIGYIDPYNGDTSYN
QKSKGKATLTADRSSSTAYMHLNSLTSEDSGIYYCARGAYGSSYAYWGQGTLVAVSA

REFERENCES

Lenferink, A. E., C. Cantin, et al. (2009). "Transcriptome profiling of a TGF-beta-induced epithelial-to-mesenchymal transition reveals extracellular clusterin as a target for therapeutic antibodies." *Oncogene* 29:831.

Adamo, V., T. Franchina, et al. (2009) "Gefitinib in lung cancer therapy." *Cancer Biol Ther* 8:206.

Shigematsu H., L. Lin L, et al., (2005) "Clinical and biological features associated with epidermal growth factor receptor gene mutations in lung cancers." *J Natl Cancer Inst* 97:339.

Barr, S., S. Thomson et al., (2008) "Bypassing cellular EGF receptor dependence through epithelial-to-mesenchymal-like transitions." *Clin Exp Metastasis* 25:685.

Mirshahidi, H. R., C. T., Hsueh (2010) "Updates in non-small cell lung cancer-insights from the 2009 45th annual meeting of the American Society of Clinical Oncology." *J Hemat & Oncol* 3:18.

Pirker, R., J. R., Peirera et al., (2012) "EGFR expression as a predictor of survival for first-line chemotherapy plus cetuximab in patients with advanced non-small-cell lung cancer: analysis of data from the phase 3 FLEX study." *Lancet* 13:33.

Costanzo, R., M. C., Piccirillo (2011) "Gefitinib in non small cell lung cancer." *J Biomed Biotechnol* 2011: 815269.

Herbst, R. S. and A. Sandler (2008) "Bevacizumab and erlotinib: A promising new approach to the treatment of advanced NSCLC." *Oncologist* 13:1166.

Yauch, R. L., T. Januario (2005) "Epithelial versus mesenchymal phenotype determines in vitro sensitivity and predicts clinical activity of erlotinib in lung cancer patients." *Clin Cancer Res* 5:8686.

Witta et al., Cancer Res. 66:944-950, 2006

Akashi, Y., Okamoto, T. et al., (2008), *Br J Cancer* 98:749.

The invention claimed is:

1. A method of treating carcinoma comprising administering an anti-clusterin antibody or an antigen binding fragment thereof that binds to amino acids 421 to 443 of human clusterin and that is capable of inhibiting epithelial-to-mesenchymal transition (EMT) and an epidermal growth factor receptor (EGFR) inhibitor to an individual having or suspected of having breast carcinoma, prostate carcinoma, colorectal carcinoma, head and neck carcinoma, lung carcinoma, pancreatic cancer or renal cell carcinoma wherein the EGFR inhibitor is an EGFR tyrosine kinase inhibitor selected from the group consisting of gefitinib, erlotinib, imatinib, lapatinib or semazinib.

2. The method of claim 1, wherein the anti-clusterin antibody or antigen binding fragment thereof and the EGFR inhibitor are administered sequentially.

3. The method of claim 1, wherein the anti-clusterin antibody or antigen binding fragment thereof is administered prior to the EGFR inhibitor.

4. The method of claim 1, wherein the anti-clusterin antibody or antigen binding fragment thereof is administered concurrently with the EGFR inhibitor.

5. The method of claim 1, wherein the breast carcinoma is triple negative breast cancer or basal-like breast cancer.

6. The method of claim 1, wherein the lung carcinoma is non-small cell lung cancer.

7. The method of claim 1, wherein the anti-clusterin antibody or antigen binding fragment thereof comprises a CDRH1 as set forth in SEQ ID NO:1 or as set forth in SEQ ID NO:45, a CDRH2 as set forth in SEQ ID NO:2 or in SEQ ID NO:46 and a CDRH3 as set forth in SEQ ID NO:3 or in SEQ ID NO:47; and/or a CDRL1 as set forth in SEQ ID NO:4 or in SEQ ID NO:48, a CDRL2 as set forth in SEQ ID NO:5 or in SEQ ID NO:49, and a CDRL3 as set forth in SEQ ID NO:6.

8. The method of claim 1, wherein the carcinoma comprises cells characterized by mesenchymal markers, by a loss of epithelial markers and/or by an epithelial-to-mesenchymal transition phenotype.

9. The method of claim 1, wherein the anti-clusterin antibody or antigen binding fragment thereof comprises a heavy chain variable domain comprising the amino acid sequence set forth in SEQ ID NO:7 and a light chain variable domain comprising the amino acid sequence set forth in SEQ ID NO:8.

10. The method of claim 1, wherein the anti-clusterin antibody or antigen binding fragment thereof comprises a heavy chain comprising the amino acid sequence set forth in SEQ ID NO:9 and a light chain comprising the amino acid sequence set forth in SEQ ID NO:10.

11. The method of claim 1, wherein the anti-clusterin antibody or antigen binding fragment thereof is encoded by nucleic acids comprising the nucleotide sequence set forth in SEQ ID NO:22 and SEQ ID NO:23.

12. The method of claim 1, wherein the carcinoma is metastatic.

13. A method for reducing the growth of carcinoma cells comprising administering an anti-clusterin antibody or an antigen binding fragment thereof that binds to amino acids 421 to 443 of human clusterin and that is capable of inhibiting epithelial-to-mesenchymal transition (EMT) and an epidermal growth factor receptor (EGFR) inhibitor to an individual having or suspected of having breast carcinoma, prostate carcinoma, colorectal carcinoma, head and neck carcinoma, lung carcinoma, pancreatic cancer or renal cell carcinoma wherein the EGFR inhibitor is an EGFR tyrosine kinase inhibitor selected from the group consisting of gefitinib, erlotinib, imatinib, lapatinib or semazinib.

14. The method of claim 13, wherein the anti-clusterin antibody or antigen binding fragment thereof comprises:
a) a heavy chain variable domain comprising a CDRH1 as set forth in SEQ ID NO:1 or as set forth in SEQ ID NO:45, a CDRH2 as set forth in SEQ ID NO:2 or in SEQ ID NO:46 and a CDRH3 as set forth in SEQ ID NO:3 or in SEQ ID NO:47; and/or a light chain variable domain comprising a CDRL1 as set forth in SEQ ID NO:4 or in SEQ ID NO:48, a CDRL2 as set forth in SEQ ID NO:5 or in SEQ ID NO:49, and a CDRL3 as set forth in SEQ ID NO:6;
b) a heavy chain variable domain comprising the amino acid sequence set forth in SEQ ID NO:7 and a light chain variable domain comprising the amino acid sequence set forth in SEQ ID NO:8, or;
c) a heavy chain comprising the amino acid sequence set forth in SEQ ID NO:9 and a light chain comprising the amino acid sequence set forth in SEQ ID NO:10.

15. The method of claim 13, wherein the anti-clusterin antibody or antigen binding fragment thereof and the EGFR inhibitor are administered sequentially or concurrently or wherein the anti-clusterin antibody or antigen binding fragment thereof is administered prior to the EGFR inhibitor.

16. The method of claim 13, wherein the lung carcinoma is non-small cell lung cancer.

17. The method of claim 13, wherein the carcinoma is metastatic.

* * * * *

SEQUENCE LISTING

```
<160> NUMBER OF SEQ ID NOS: 67

<210> SEQ ID NO 1
<211> LENGTH: 10
<212> TYPE: PRT
<213> ORGANISM: Artificial Sequence
<220> FEATURE:
<223> OTHER INFORMATION: 16B5 heavy chain CDR1

<400> SEQUENCE: 1

Gly Phe Asn Ile Lys Asp Ile Tyr Met His
1               5                   10

<210> SEQ ID NO 2
<211> LENGTH: 17
<212> TYPE: PRT
<213> ORGANISM: Artificial Sequence
<220> FEATURE:
<223> OTHER INFORMATION: 16B5 heavy chain CDR2

<400> SEQUENCE: 2

Arg Ile Asp Pro Ala Tyr Gly Asn Thr Lys Tyr Asp Pro Lys Phe Gln
1               5                   10                  15

Gly

<210> SEQ ID NO 3
<211> LENGTH: 8
<212> TYPE: PRT
<213> ORGANISM: Artificial Sequence
<220> FEATURE:
<223> OTHER INFORMATION: 16B5 heavy chain CDR3

<400> SEQUENCE: 3

Arg Tyr Asp Thr Ala Met Asp Tyr
1               5
```

```
<210> SEQ ID NO 4
<211> LENGTH: 17
<212> TYPE: PRT
<213> ORGANISM: Artificial Sequence
<220> FEATURE:
<223> OTHER INFORMATION: 16B5 light chain CDR1

<400> SEQUENCE: 4

Lys Ser Ser Gln Ser Leu Leu Asn Ser Arg Thr Arg Lys Asn Tyr Leu
1               5                   10                  15

Ala

<210> SEQ ID NO 5
<211> LENGTH: 7
<212> TYPE: PRT
<213> ORGANISM: Artificial Sequence
<220> FEATURE:
<223> OTHER INFORMATION: 16B5 light chain CDR2

<400> SEQUENCE: 5

Trp Ala Ser Thr Arg Glu Ser
1               5

<210> SEQ ID NO 6
<211> LENGTH: 8
<212> TYPE: PRT
<213> ORGANISM: Artificial Sequence
<220> FEATURE:
<223> OTHER INFORMATION: 16B5 light chain CDR3

<400> SEQUENCE: 6

Lys Gln Ser Tyr Asn Leu Trp Thr
1               5

<210> SEQ ID NO 7
<211> LENGTH: 117
<212> TYPE: PRT
<213> ORGANISM: Artificial Sequence
<220> FEATURE:
<223> OTHER INFORMATION: h16B5 humanized heavy chain variable region

<400> SEQUENCE: 7

Gln Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Ile
            20                  25                  30

Tyr Met His Trp Val Gln Gln Ala Pro Gly Lys Gly Leu Glu Trp Met
        35                  40                  45

Gly Arg Ile Asp Pro Ala Tyr Gly Asn Thr Lys Tyr Asp Pro Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Tyr Asp Thr Ala Met Asp Tyr Trp Gly Gln Gly Thr Leu
            100                 105                 110

Val Thr Val Ser Ser
        115

<210> SEQ ID NO 8
<211> LENGTH: 112
<212> TYPE: PRT
```

<213> ORGANISM: Artificial Sequence
<220> FEATURE:
<223> OTHER INFORMATION: h16B5 humanized light chain variable region

<400> SEQUENCE: 8

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Trp Thr Phe Gly Gln Gly Thr Lys Leu Glu Ile Lys
            100                 105                 110

<210> SEQ ID NO 9
<211> LENGTH: 443
<212> TYPE: PRT
<213> ORGANISM: Artificial Sequence
<220> FEATURE:
<223> OTHER INFORMATION: Complete heavy chain immunoglobulin sequence
      for h16B5

<400> SEQUENCE: 9

Gln Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Ile
            20                  25                  30

Tyr Met His Trp Val Gln Gln Ala Pro Gly Lys Gly Leu Glu Trp Met
        35                  40                  45

Gly Arg Ile Asp Pro Ala Tyr Gly Asn Thr Lys Tyr Asp Pro Lys Phe
50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Tyr Asp Thr Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser His Glu Asp Pro Glu Val Gln Phe Asn
                260                 265                 270

Trp Tyr Val Asp Gly Val Glu Val His Asn Ala Lys Thr Lys Pro Arg
            275                 280                 285

Glu Glu Gln Phe Asn Ser Thr Phe Arg Val Val Ser Val Leu Thr Val
        290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 10
<211> LENGTH: 217
<212> TYPE: PRT
<213> ORGANISM: Artificial Sequence
<220> FEATURE:
<223> OTHER INFORMATION: Complete light chain immunoglobulin sequence
      for h16B5

<400> SEQUENCE: 10

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Trp Thr Phe Gly Gln Gly Thr Lys Leu Glu Ile Lys
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro

```
                130                 135                 140
Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 11
<211> LENGTH: 10
<212> TYPE: PRT
<213> ORGANISM: Artificial Sequence
<220> FEATURE:
<223> OTHER INFORMATION: 21B12 heavy chain CDR1

<400> SEQUENCE: 11

Gly Tyr Thr Phe Thr Asn Tyr Gly Met His
1               5                   10

<210> SEQ ID NO 12
<211> LENGTH: 17
<212> TYPE: PRT
<213> ORGANISM: Artificial Sequence
<220> FEATURE:
<223> OTHER INFORMATION: 21B12 heavy chain CDR2

<400> SEQUENCE: 12

Trp Ile Asn Thr Tyr Thr Gly Glu Pro Thr Tyr Ala Asp Asp Phe Lys
1               5                   10                  15

Gly

<210> SEQ ID NO 13
<211> LENGTH: 9
<212> TYPE: PRT
<213> ORGANISM: Artificial Sequence
<220> FEATURE:
<223> OTHER INFORMATION: 21B12 heavy chain CDR3

<400> SEQUENCE: 13

Asp Gly Phe Leu Tyr Phe Phe Asp Tyr
1               5

<210> SEQ ID NO 14
<211> LENGTH: 17
<212> TYPE: PRT
<213> ORGANISM: Artificial Sequence
<220> FEATURE:
<223> OTHER INFORMATION: 21B12 light chain CDR1

<400> SEQUENCE: 14

Lys Ser Ser Gln Ser Leu Leu Tyr Ser Ser Asn Gln Lys Asn Tyr Leu
1               5                   10                  15

Ala

<210> SEQ ID NO 15
<211> LENGTH: 7
<212> TYPE: PRT
<213> ORGANISM: Artificial Sequence
<220> FEATURE:
```

<223> OTHER INFORMATION: 21B12 light chain CDR2

<400> SEQUENCE: 15

Trp Ala Ser Thr Arg Glu Ser
1               5

<210> SEQ ID NO 16
<211> LENGTH: 9
<212> TYPE: PRT
<213> ORGANISM: Artificial Sequence
<220> FEATURE:
<223> OTHER INFORMATION: 21B12 light chain CDR3

<400> SEQUENCE: 16

Gln Gln Tyr Tyr Ile Tyr Pro Arg Thr
1               5

<210> SEQ ID NO 17
<211> LENGTH: 118
<212> TYPE: PRT
<213> ORGANISM: Artificial Sequence
<220> FEATURE:
<223> OTHER INFORMATION: h21B12 humanized heavy chain variable region

<400> SEQUENCE: 17

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met His Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Gly Phe Leu Tyr Phe Phe Asp Tyr Trp Gly Gln Gly Thr
            100                 105                 110

Leu Val Thr Val Ser Ser
        115

<210> SEQ ID NO 18
<211> LENGTH: 113
<212> TYPE: PRT
<213> ORGANISM: Artificial Sequence
<220> FEATURE:
<223> OTHER INFORMATION: h21B12 humanized light chain variable region

<400> SEQUENCE: 18

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

```
Ile Ser Ser Leu Gln Ala Glu Asp Val Ala Val Tyr Tyr Cys Gln Gln
                85                  90                  95

Tyr Tyr Ile Tyr Pro Arg Thr Phe Gly Gln Gly Thr Lys Leu Glu Ile
            100                 105                 110

Lys

<210> SEQ ID NO 19
<211> LENGTH: 444
<212> TYPE: PRT
<213> ORGANISM: Artificial Sequence
<220> FEATURE:
<223> OTHER INFORMATION: Complete heavy chain immunoglobulin sequence
      for h21B12

<400> SEQUENCE: 19

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met His Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Gly Phe Leu Tyr Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320
```

```
Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
            435                 440

<210> SEQ ID NO 20
<211> LENGTH: 220
<212> TYPE: PRT
<213> ORGANISM: Artificial Sequence
<220> FEATURE:
<223> OTHER INFORMATION: complete light chain immunoglobulin sequence
      for h21B12

<400> SEQUENCE: 20

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ile Tyr Pro Arg Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 21
```

<211> LENGTH: 1389
<212> TYPE: DNA
<213> ORGANISM: Artificial Sequence
<220> FEATURE:
<223> OTHER INFORMATION: complete nucleotide sequence of the heavy chain of h16B5

<400> SEQUENCE: 21

| | |
|---|---|
| atggactgga cctggcggat cctgttcctg gtggccgctg ctaccggcac ccacgcccag | 60 |
| gtgcagctgg tgcagtctgg cgccgaggtg aagaagcctg gcgccaccgt caagatcagc | 120 |
| tgcaaggtgt ccggcttcaa catcaaggac atctacatgc actgggtgca gcaggctcca | 180 |
| ggcaagggac tggagtggat gggccggatc gaccctgcct acggcaacac caagtacgac | 240 |
| cctaagttcc agggccgggt gaccatcacc gccgacacct ccaccgacac cgcctacatg | 300 |
| gaactgtcct ccctgcggtc cgaggacacc gccgtgtact actgcgcccg agatacgac | 360 |
| accgccatgg attactgggg ccagggcacc ctggtgaccg tgtcctccgc ttccaccaag | 420 |
| ggcccatcgg tcttcccct ggcgccctgc tccaggagca cctccgagag cacagcggcc | 480 |
| ctgggctgcc tggtcaagga ctacttcccc gaaccggtga cggtgtcgtg gaactcaggc | 540 |
| gctctgacca gcggcgtgca caccttccca gctgtcctac agtcctcagg actctactcc | 600 |
| ctcagcagcg tggtgaccgt gccctccagc aacttcggca cccagaccta cacctgcaac | 660 |
| gtagatcaca agcccagcaa caccaaggtg gacaagacag ttgagcgcaa atgttgtgtc | 720 |
| gagtgcccac cgtgcccagc accacctgtg gcaggaccgt cagtcttcct cttccccca | 780 |
| aaacccaagg acaccctcat gatctcccgg acccctgagg tcacgtgcgt ggtggtggac | 840 |
| gtgagccacg aagaccccga ggtccagttc aactggtacg tggacggcgt ggaggtgcat | 900 |
| aatgccaaga caaagccacg ggaggagcag ttcaacagca cgttccgtgt ggtcagcgtc | 960 |
| ctcaccgttg tgcaccagga ctggctgaac ggcaaggagt acaagtgcaa ggtctccaac | 1020 |
| aaaggcctcc cagcccccat cgagaaaacc atctccaaaa ccaaagggca gccccgagaa | 1080 |
| ccacaggtgt acaccctgcc cccatcccgg gaggagatga ccaagaacca ggtcagcctg | 1140 |
| acctgcctgg tcaaaggctt ctaccccagc gacatcgccg tggagtggga gagcaatggg | 1200 |
| cagccggaga acaactacaa gaccacacct cccatgctgg actccgacgg ctccttcttc | 1260 |
| ctctacagca agctcaccgt ggacaagagc aggtggcagc aggggaacgt cttctcatgc | 1320 |
| tccgtgatgc atgaggctct gcacaaccac tacacgcaga gagcctctcc cctgtctccg | 1380 |
| ggtaaatga | 1389 |

<210> SEQ ID NO 22
<211> LENGTH: 1392
<212> TYPE: DNA
<213> ORGANISM: Artificial Sequence
<220> FEATURE:
<223> OTHER INFORMATION: complete nucleotide sequence of the heavy chain of h21B12

<400> SEQUENCE: 22

| | |
|---|---|
| atggactgga cctggcggat cctgtttctg gtggccgctg ctaccggcac acacgcccag | 60 |
| gtgcagctgg tgcagtccgg ctccgagctg aagaaacctg gcgcctccgt gaaggtgtcc | 120 |
| tgcaaggcct ccggctacac cttcaccaac tacggcatgc actgggtgcg ccaggcacct | 180 |
| ggacagggac tggaatggat gggctggatc aacacctaca ccggcgagcc tacctacgcc | 240 |
| gacgacttca agggcagatt cgtgttctcc ctggacacct ccgtgtccac cgcctacctg | 300 |
| cagatctcct ccctgaaggc cgaggacacc gccgtgtact actgcgccag ggacggcttc | 360 |

```
ctgtacttct tcgactactg gggccagggc accctggtga ccgtgtcctc tgcctccacc    420 aagggcccttt ccgtgttccc tctggccct tgctcccggt ccacctctga gtctaccgcc    480
gctctgggct gcctggtgaa ggactacttc cctgagcctg tgacagtgtc ctggaactct    540
ggcgccctga cctctggcgt gcacaccttc cctgccgtgc tgcagtcctc cggcctgtac    600
tccctgtcct ccgtggtgac agtgccttcc tccaacttcg gcacccagac ctacacctgc    660
aacgtggacc acaagccttc aacaccaag gtggacaaga ccgtggagcg gaagtgctgc    720
gtggagtgcc ctccttgtcc tgctcctcct gtggctggcc ctagcgtgtt cctgttccct    780
cctaagccta aggacaccct gatgatctcc cggacccctg aagtgacctg cgtggtggtg    840
gacgtgtccc acgaggaccc tgaggtgcag ttcaattggt acgtggacgg cgtggaggtg    900
cacaacgcca agaccaagcc tcgggaggaa cagttcaact ccaccttccg ggtggtgtcc    960
gtgctgaccg tggtgcacca ggactggctg aacggcaaag aatacaagtg caaggtgtcc   1020
aacaagggcc tgcctgcccc tatcgaaaag accatctcta agaccaaggg ccagcctcgc   1080
gagcctcagg tgtacacccctgcctccctcc cgcgaggaaa tgaccaagaa ccaggtgtcc   1140
ctgacctgtc tggtgaaggg cttctaccct tccgatatcg ccgtggagtg ggagtctaac   1200
ggccagcctg agaacaacta caagaccacc cctcctatgc tggactccga cggctccttc   1260
ttcctgtaca gcaagctgac agtggacaag tcccggtggc agcagggcaa cgtgttctcc   1320
tgctccgtga tgcacgaggc cctgcacaac cactacaccc agaagtccct gtccctgtct   1380
cctggcaagt ga                                                       1392

<210> SEQ ID NO 23
<211> LENGTH: 720
<212> TYPE: DNA
<213> ORGANISM: Artificial Sequence
<220> FEATURE:
<223> OTHER INFORMATION: complete nucleotide sequence of the light chain
      of h16B5

<400> SEQUENCE: 23
atggtgctgc agacccaggt gttcatctcc ctgctgctgt ggatctccgg cgcctacggc     60
gacatcgtga tgacccagtc ccccgactcc ctggccgtgt ccctgggcga gagagccacc    120
atcaactgca gtcctccca gtccctgctg aactcccgga cccggaagaa ctacctggcc    180
tggtatcagc agaagcctgg ccagcctcct aagctgctga tctactgggc ctccacccgg    240
gagtccggcg tgcctgaccg gttctccggc tccggcagcg gcaccgactt caccctgacc    300
atcagctccc tgcaggccga ggacgtggcc gtgtactact gcaagcagtc ctacaacctg    360
tggaccttcg gccagggcac caagctggag atcaagcgga ctgtggctgc accatctgtc    420
ttcatcttcc cgccatctga tgagcagttg aaatctggaa ctgcctctgt tgtgtgcctg    480
ctgaataact tctatcccag agaggccaaa gtacagtgga aggtggataa cgccctccaa    540
tcgggtaact cccaggagag tgtcacagag caggacagca aggacagcac ctacagcctc    600
agcagcaccc tgacgctgag caaagcagac tacgagaaac acaaagtcta cgcctgcgaa    660
gtcacccatc agggcctgag ctcgcccgtc acaaagagct tcaacagggg agagtgttag    720

<210> SEQ ID NO 24
<211> LENGTH: 723
<212> TYPE: DNA
<213> ORGANISM: Artificial Sequence
<220> FEATURE:
<223> OTHER INFORMATION: complete nucleotide sequence of the light chain
``` of h21B12

<400> SEQUENCE: 24

```
atggtgctgc agacccaggt gttcatctcc ctgctgctgt ggatctctgg cgcctacggc      60
gacatcgtga tgacccagtc ccccgactct ctggctgtgt ccctgggcga gcgggccacc     120
atcaactgca agtcctccca gtccctgctg tactcctcca accagaagaa ctacctggcc     180
tggtatcagc agaagcctgg ccagcctcct aagctgctga tctactgggc ctccacccgg     240
gaatctggcg tgcctgaccg gttctccggc tctggctccg gcaccgactt caccctgacc     300
atcagctccc tgcaggccga ggacgtggcc gtgtactact gccagcagta ctacatctac     360
cctcggacct tcggccaggg caccaagctg gaaatcaagc ggaccgtggc cgctccttcc     420
gtgttcatct ccccccttc cgacgagcag ctgaagtccg gcaccgcctc tgtggtgtgc      480
ctgctgaaca acttctaccc ccgggaggcc aaggtgcagt ggaaggtgga caacgccctg     540
cagtccggca actcccagga atccgtcacc gagcaggact ccaaggactc tacctactcc     600
ctgtcctcca ccctgaccct gtccaaggcc gactacgaga agcacaaggt gtacgcctgc     660
gaagtgaccc accagggcct gtcctctccc gtgaccaagt ccttcaaccg gggcgagtgc     720
tga                                                                    723
```

<210> SEQ ID NO 25
<211> LENGTH: 112
<212> TYPE: PRT
<213> ORGANISM: Artificial Sequence
<220> FEATURE:
<223> OTHER INFORMATION: murine 16B5 light chain variable region

<400> SEQUENCE: 25

Asp Ile Val Met Ser Gln Ser Pro Ser Ser Leu Ala Val Ser Ala Gly
1               5                  10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Trp Thr Phe Gly Gly Gly Thr Lys Leu Glu Phe Lys
            100                 105                 110

<210> SEQ ID NO 26
<211> LENGTH: 112
<212> TYPE: PRT
<213> ORGANISM: Artificial Sequence
<220> FEATURE:
<223> OTHER INFORMATION: 16B5 light chain variable region - consensus 1
<220> FEATURE:
<221> NAME/KEY: MISC_FEATURE
<222> LOCATION: (5)..(5)
<223> OTHER INFORMATION: Xaa is an amino acid substitution in comparison
      with SEQ ID NO.:25
<220> FEATURE:
<221> NAME/KEY: MISC_FEATURE
<222> LOCATION: (9)..(9)
<223> OTHER INFORMATION: Xaa is an amino acid substitution in comparison
      with SEQ ID NO.:25
<220> FEATURE:

```
<221> NAME/KEY: MISC_FEATURE
<222> LOCATION: (15)..(15)
<223> OTHER INFORMATION: Xaa is an amino acid substitution in comparison
      with SEQ ID NO.:25
<220> FEATURE:
<221> NAME/KEY: MISC_FEATURE
<222> LOCATION: (18)..(18)
<223> OTHER INFORMATION: Xaa is an amino acid substitution in comparison
      with SEQ ID NO.:25
<220> FEATURE:
<221> NAME/KEY: MISC_FEATURE
<222> LOCATION: (19)..(19)
<223> OTHER INFORMATION: Xaa is an amino acid substitution in comparison
      with SEQ ID NO.:25
<220> FEATURE:
<221> NAME/KEY: MISC_FEATURE
<222> LOCATION: (21)..(21)
<223> OTHER INFORMATION: Xaa is an amino acid substitution in comparison
      with SEQ ID NO.:25
<220> FEATURE:
<221> NAME/KEY: MISC_FEATURE
<222> LOCATION: (22)..(22)
<223> OTHER INFORMATION: Xaa is an amino acid substitution in comparison
      with SEQ ID NO.:25
<220> FEATURE:
<221> NAME/KEY: MISC_FEATURE
<222> LOCATION: (49)..(49)
<223> OTHER INFORMATION: Xaa is an amino acid substitution in comparison
      with SEQ ID NO.:25
<220> FEATURE:
<221> NAME/KEY: MISC_FEATURE
<222> LOCATION: (69)..(69)
<223> OTHER INFORMATION: Xaa is an amino acid substitution in comparison
      with SEQ ID NO.:25
<220> FEATURE:
<221> NAME/KEY: MISC_FEATURE
<222> LOCATION: (84)..(84)
<223> OTHER INFORMATION: Xaa is an amino acid substitution in comparison
      with SEQ ID NO.:25
<220> FEATURE:
<221> NAME/KEY: MISC_FEATURE
<222> LOCATION: (89)..(89)
<223> OTHER INFORMATION: Xaa is an amino acid substitution in comparison
      with SEQ ID NO.:25
<220> FEATURE:
<221> NAME/KEY: MISC_FEATURE
<222> LOCATION: (105)..(105)
<223> OTHER INFORMATION: Xaa is an amino acid substitution in comparison
      with SEQ ID NO.:25
<220> FEATURE:
<221> NAME/KEY: MISC_FEATURE
<222> LOCATION: (111)..(111)
<223> OTHER INFORMATION: Xaa is an amino acid substitution in comparison
      with SEQ ID NO.:25

<400> SEQUENCE: 26

Asp Ile Val Met Xaa Gln Ser Pro Xaa Ser Leu Ala Val Ser Xaa Gly
1               5                   10                  15

Glu Xaa Xaa Thr Xaa Xaa Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Xaa Pro Lys Leu Leu Ile Tyr Trp Ala Ser Thr Arg Glu Ser Gly Val
    50                  55                  60

Pro Asp Arg Phe Xaa Gly Ser Gly Ser Gly Thr Asp Phe Thr Leu Thr
65                  70                  75                  80

Ile Ser Ser Xaa Gln Ala Glu Asp Xaa Ala Val Tyr Tyr Cys Lys Gln
                85                  90                  95

Ser Tyr Asn Leu Trp Thr Phe Gly Xaa Gly Thr Lys Leu Glu Xaa Lys
            100                 105                 110
```

```
<210> SEQ ID NO 27
<211> LENGTH: 112
<212> TYPE: PRT
<213> ORGANISM: Artificial Sequence
<220> FEATURE:
<223> OTHER INFORMATION: 16B5 light chain variable region - consensus 2
<220> FEATURE:
<221> NAME/KEY: MISC_FEATURE
<222> LOCATION: (5)..(5)
<223> OTHER INFORMATION: Xaa may be a neutral hydrophilic amino acid
<220> FEATURE:
<221> NAME/KEY: MISC_FEATURE
<222> LOCATION: (9)..(9)
<223> OTHER INFORMATION: Xaa may be D or S
<220> FEATURE:
<221> NAME/KEY: MISC_FEATURE
<222> LOCATION: (15)..(15)
<223> OTHER INFORMATION: Xaa may be an hydrophobic amino acid
<220> FEATURE:
<221> NAME/KEY: MISC_FEATURE
<222> LOCATION: (18)..(18)
<223> OTHER INFORMATION: Xaa may be a basic  amino acid
<220> FEATURE:
<221> NAME/KEY: MISC_FEATURE
<222> LOCATION: (19)..(19)
<223> OTHER INFORMATION: Xaa may be an hydrophobic amino acid
<220> FEATURE:
<221> NAME/KEY: MISC_FEATURE
<222> LOCATION: (21)..(21)
<223> OTHER INFORMATION: Xaa may be an hydrophobic amino acid
<220> FEATURE:
<221> NAME/KEY: MISC_FEATURE
<222> LOCATION: (22)..(22)
<223> OTHER INFORMATION: Xaa may be N or S
<220> FEATURE:
<221> NAME/KEY: MISC_FEATURE
<222> LOCATION: (49)..(49)
<223> OTHER INFORMATION: Xaa may be P or S
<220> FEATURE:
<221> NAME/KEY: MISC_FEATURE
<222> LOCATION: (69)..(69)
<223> OTHER INFORMATION: Xaa may be a neutral hydrophilic amino acid
<220> FEATURE:
<221> NAME/KEY: MISC_FEATURE
<222> LOCATION: (84)..(84)
<223> OTHER INFORMATION: Xaa may be an hydrophobic amino acid
<220> FEATURE:
<221> NAME/KEY: MISC_FEATURE
<222> LOCATION: (89)..(89)
<223> OTHER INFORMATION: Xaa may be an hydrophobic amino acid
<220> FEATURE:
<221> NAME/KEY: MISC_FEATURE
<222> LOCATION: (105)..(105)
<223> OTHER INFORMATION: Xaa may be Q or G
<220> FEATURE:
<221> NAME/KEY: MISC_FEATURE
<222> LOCATION: (111)..(111)
<223> OTHER INFORMATION: Xaa may be I or F

<400> SEQUENCE: 27

Asp Ile Val Met Xaa Gln Ser Pro Xaa Ser Leu Ala Val Ser Xaa Gly
1               5                   10                  15

Glu Xaa Xaa Thr Xaa Xaa Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Xaa Pro Lys Leu Leu Ile Tyr Trp Ala Ser Thr Arg Glu Ser Gly Val
50                  55                  60

Pro Asp Arg Phe Xaa Gly Ser Gly Ser Gly Thr Asp Phe Thr Leu Thr
65                  70                  75                  80

Ile Ser Ser Xaa Gln Ala Glu Asp Xaa Ala Val Tyr Tyr Cys Lys Gln
                85                  90                  95
```

Ser Tyr Asn Leu Trp Thr Phe Gly Xaa Gly Thr Lys Leu Glu Xaa Lys
                100                 105                 110

<210> SEQ ID NO 28
<211> LENGTH: 112
<212> TYPE: PRT
<213> ORGANISM: Artificial Sequence
<220> FEATURE:
<223> OTHER INFORMATION: 16B5 light chain variable region - consensus 3
<220> FEATURE:
<221> NAME/KEY: MISC_FEATURE
<222> LOCATION: (5)..(5)
<223> OTHER INFORMATION: Xaa may be T or S
<220> FEATURE:
<221> NAME/KEY: MISC_FEATURE
<222> LOCATION: (9)..(9)
<223> OTHER INFORMATION: Xaa may be D or S
<220> FEATURE:
<221> NAME/KEY: MISC_FEATURE
<222> LOCATION: (15)..(15)
<223> OTHER INFORMATION: Xaa may be L or A
<220> FEATURE:
<221> NAME/KEY: MISC_FEATURE
<222> LOCATION: (18)..(18)
<223> OTHER INFORMATION: Xaa may be R or K
<220> FEATURE:
<221> NAME/KEY: MISC_FEATURE
<222> LOCATION: (19)..(19)
<223> OTHER INFORMATION: Xaa may be A or V
<220> FEATURE:
<221> NAME/KEY: MISC_FEATURE
<222> LOCATION: (21)..(21)
<223> OTHER INFORMATION: Xaa may be I or M
<220> FEATURE:
<221> NAME/KEY: MISC_FEATURE
<222> LOCATION: (22)..(22)
<223> OTHER INFORMATION: Xaa may be N or S
<220> FEATURE:
<221> NAME/KEY: MISC_FEATURE
<222> LOCATION: (49)..(49)
<223> OTHER INFORMATION: Xaa may be P or S
<220> FEATURE:
<221> NAME/KEY: MISC_FEATURE
<222> LOCATION: (69)..(69)
<223> OTHER INFORMATION: Xaa may be S or T
<220> FEATURE:
<221> NAME/KEY: MISC_FEATURE
<222> LOCATION: (84)..(84)
<223> OTHER INFORMATION: Xaa may be L or V
<220> FEATURE:
<221> NAME/KEY: MISC_FEATURE
<222> LOCATION: (89)..(89)
<223> OTHER INFORMATION: Xaa may be V or L
<220> FEATURE:
<221> NAME/KEY: MISC_FEATURE
<222> LOCATION: (105)..(105)
<223> OTHER INFORMATION: Xaa may be Q or G
<220> FEATURE:
<221> NAME/KEY: MISC_FEATURE
<222> LOCATION: (111)..(111)
<223> OTHER INFORMATION: Xaa may be I or F

<400> SEQUENCE: 28

Asp Ile Val Met Xaa Gln Ser Pro Xaa Ser Leu Ala Val Ser Xaa Gly
1               5                   10                  15

Glu Xaa Xaa Thr Xaa Xaa Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Xaa Pro Lys Leu Leu Ile Tyr Trp Ala Ser Thr Arg Glu Ser Gly Val
    50                  55                  60

Pro Asp Arg Phe Xaa Gly Ser Gly Ser Gly Thr Asp Phe Thr Leu Thr
65                  70                  75                  80

```
Ile Ser Ser Xaa Gln Ala Glu Asp Xaa Ala Val Tyr Tyr Cys Lys Gln
                85              90                  95

Ser Tyr Asn Leu Trp Thr Phe Gly Xaa Gly Thr Lys Leu Glu Xaa Lys
            100                 105                 110

<210> SEQ ID NO 29
<211> LENGTH: 117
<212> TYPE: PRT
<213> ORGANISM: Artificial Sequence
<220> FEATURE:
<223> OTHER INFORMATION: murine 16B5 heavy chain variable region

<400> SEQUENCE: 29

Glu Val Gln Leu Gln Gln Ser Gly Ala Glu Leu Val Lys Pro Gly Ala
1               5                   10                  15

Ser Val Arg Leu Ser Cys Thr Thr Ser Gly Phe Asn Ile Lys Asp Ile
            20                  25                  30

Tyr Met His Trp Val Lys Gln Arg Pro Glu Gln Gly Leu Glu Trp Ile
        35                  40                  45

Gly Arg Ile Asp Pro Ala Tyr Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Arg Tyr Asp Thr Ala Met Asp Tyr Trp Gly Gln Gly Thr Ser
            100                 105                 110

Val Thr Val Ser Ser
        115

<210> SEQ ID NO 30
<211> LENGTH: 117
<212> TYPE: PRT
<213> ORGANISM: Artificial Sequence
<220> FEATURE:
<223> OTHER INFORMATION: 16B5 heavy chain variable region - consensus 1
<220> FEATURE:
<221> NAME/KEY: MISC_FEATURE
<222> LOCATION: (1)..(1)
<223> OTHER INFORMATION: Xaa is an amino acid substitution in comparison
      with SEQ ID NO.:29
<220> FEATURE:
<221> NAME/KEY: MISC_FEATURE
<222> LOCATION: (5)..(5)
<223> OTHER INFORMATION: Xaa is an amino acid substitution in comparison
      with SEQ ID NO.:29
<220> FEATURE:
<221> NAME/KEY: MISC_FEATURE
<222> LOCATION: (11)..(11)
<223> OTHER INFORMATION: Xaa is an amino acid substitution in comparison
      with SEQ ID NO.:29
<220> FEATURE:
<221> NAME/KEY: MISC_FEATURE
<222> LOCATION: (12)..(12)
<223> OTHER INFORMATION: Xaa is an amino acid substitution in comparison
      with SEQ ID NO.:29
<220> FEATURE:
<221> NAME/KEY: MISC_FEATURE
<222> LOCATION: (17)..(17)
<223> OTHER INFORMATION: Xaa is an amino acid substitution in comparison
      with SEQ ID NO.:29
<220> FEATURE:
<221> NAME/KEY: MISC_FEATURE
<222> LOCATION: (19)..(19)
<223> OTHER INFORMATION: Xaa is an amino acid substitution in comparison
      with SEQ ID NO.:29
<220> FEATURE:
```

```
<221> NAME/KEY: MISC_FEATURE
<222> LOCATION: (20)..(20)
<223> OTHER INFORMATION: Xaa is an amino acid substitution in comparison
      with SEQ ID NO.:29
<220> FEATURE:
<221> NAME/KEY: MISC_FEATURE
<222> LOCATION: (23)..(23)
<223> OTHER INFORMATION: Xaa is an amino acid substitution in comparison
      with SEQ ID NO.:29
<220> FEATURE:
<221> NAME/KEY: MISC_FEATURE
<222> LOCATION: (24)..(24)
<223> OTHER INFORMATION: Xaa is an amino acid substitution in comparison
      with SEQ ID NO.:29
<220> FEATURE:
<221> NAME/KEY: MISC_FEATURE
<222> LOCATION: (38)..(38)
<223> OTHER INFORMATION: Xaa is an amino acid substitution in comparison
      with SEQ ID NO.:29
<220> FEATURE:
<221> NAME/KEY: MISC_FEATURE
<222> LOCATION: (40)..(40)
<223> OTHER INFORMATION: Xaa is an amino acid substitution in comparison
      with SEQ ID NO.:29
<220> FEATURE:
<221> NAME/KEY: MISC_FEATURE
<222> LOCATION: (42)..(42)
<223> OTHER INFORMATION: Xaa is an amino acid substitution in comparison
      with SEQ ID NO.:29
<220> FEATURE:
<221> NAME/KEY: MISC_FEATURE
<222> LOCATION: (43)..(43)
<223> OTHER INFORMATION: Xaa is an amino acid substitution in comparison
      with SEQ ID NO.:29
<220> FEATURE:
<221> NAME/KEY: MISC_FEATURE
<222> LOCATION: (48)..(48)
<223> OTHER INFORMATION: Xaa is an amino acid substitution in comparison
      with SEQ ID NO.:29
<220> FEATURE:
<221> NAME/KEY: MISC_FEATURE
<222> LOCATION: (67)..(67)
<223> OTHER INFORMATION: Xaa is an amino acid substitution in comparison
      with SEQ ID NO.:29
<220> FEATURE:
<221> NAME/KEY: MISC_FEATURE
<222> LOCATION: (68)..(68)
<223> OTHER INFORMATION: Xaa is an amino acid substitution in comparison
      with SEQ ID NO.:29
<220> FEATURE:
<221> NAME/KEY: MISC_FEATURE
<222> LOCATION: (76)..(76)
<223> OTHER INFORMATION: Xaa is an amino acid substitution in comparison
      with SEQ ID NO.:29
<220> FEATURE:
<221> NAME/KEY: MISC_FEATURE
<222> LOCATION: (77)..(77)
<223> OTHER INFORMATION: Xaa is an amino acid substitution in comparison
      with SEQ ID NO.:29
<220> FEATURE:
<221> NAME/KEY: MISC_FEATURE
<222> LOCATION: (81)..(81)
<223> OTHER INFORMATION: Xaa is an amino acid substitution in comparison
      with SEQ ID NO.:29
<220> FEATURE:
<221> NAME/KEY: MISC_FEATURE
<222> LOCATION: (82)..(82)
<223> OTHER INFORMATION: Xaa is an amino acid substitution in comparison
      with SEQ ID NO.:29
<220> FEATURE:
<221> NAME/KEY: MISC_FEATURE
<222> LOCATION: (87)..(87)
<223> OTHER INFORMATION: Xaa is an amino acid substitution in comparison
      with SEQ ID NO.:29
<220> FEATURE:
<221> NAME/KEY: MISC_FEATURE
<222> LOCATION: (112)..(112)
<223> OTHER INFORMATION: Xaa is an amino acid substitution in comparison
      with SEQ ID NO.:29
```

<400> SEQUENCE: 30

```
Xaa Val Gln Leu Xaa Gln Ser Gly Ala Glu Xaa Xaa Lys Pro Gly Ala
1               5                   10                  15
Xaa Val Xaa Xaa Ser Cys Xaa Xaa Ser Gly Phe Asn Ile Lys Asp Ile
            20                  25                  30
Tyr Met His Trp Val Xaa Gln Xaa Pro Xaa Xaa Gly Leu Glu Trp Xaa
        35                  40                  45
Gly Arg Ile Asp Pro Ala Tyr Gly Asn Thr Lys Tyr Asp Pro Lys Phe
50                  55                  60
Gln Gly Xaa Xaa Thr Ile Thr Ala Asp Thr Ser Xaa Xaa Thr Ala Tyr
65                  70                  75                  80
Xaa Xaa Leu Ser Ser Leu Xaa Ser Glu Asp Thr Ala Val Tyr Tyr Cys
            85                  90                  95
Ala Arg Arg Tyr Asp Thr Ala Met Asp Tyr Trp Gly Gln Gly Thr Xaa
                100                 105                 110
Val Thr Val Ser Ser
            115
```

<210> SEQ ID NO 31
<211> LENGTH: 117
<212> TYPE: PRT
<213> ORGANISM: Artificial Sequence
<220> FEATURE:
<223> OTHER INFORMATION: 16B5 heavy chain variable region - consensus 2
<220> FEATURE:
<221> NAME/KEY: MISC_FEATURE
<222> LOCATION: (1)..(1)
<223> OTHER INFORMATION: Xaa may be Q or E
<220> FEATURE:
<221> NAME/KEY: MISC_FEATURE
<222> LOCATION: (5)..(5)
<223> OTHER INFORMATION: Xaa may be V or Q
<220> FEATURE:
<221> NAME/KEY: MISC_FEATURE
<222> LOCATION: (11)..(11)
<223> OTHER INFORMATION: Xaa may be an hydrophobic amino acid
<220> FEATURE:
<221> NAME/KEY: MISC_FEATURE
<222> LOCATION: (12)..(12)
<223> OTHER INFORMATION: Xaa may be K or V
<220> FEATURE:
<221> NAME/KEY: MISC_FEATURE
<222> LOCATION: (17)..(17)
<223> OTHER INFORMATION: Xaa may be a neutral hydrophilic amino acid
<220> FEATURE:
<221> NAME/KEY: MISC_FEATURE
<222> LOCATION: (19)..(19)
<223> OTHER INFORMATION: Xaa may be a basic amino acid
<220> FEATURE:
<221> NAME/KEY: MISC_FEATURE
<222> LOCATION: (20)..(20)
<223> OTHER INFORMATION: Xaa may be an hydrophobic amino acid
<220> FEATURE:
<221> NAME/KEY: MISC_FEATURE
<222> LOCATION: (23)..(23)
<223> OTHER INFORMATION: Xaa may be K or T
<220> FEATURE:
<221> NAME/KEY: MISC_FEATURE
<222> LOCATION: (24)..(24)
<223> OTHER INFORMATION: Xaa may be V or T
<220> FEATURE:
<221> NAME/KEY: MISC_FEATURE
<222> LOCATION: (38)..(38)
<223> OTHER INFORMATION: Xaa may be a basic amino acid
<220> FEATURE:
<221> NAME/KEY: MISC_FEATURE
<222> LOCATION: (40)..(40)
<223> OTHER INFORMATION: Xaa may be A or R
<220> FEATURE:

```
<221> NAME/KEY: MISC_FEATURE
<222> LOCATION: (42)..(42)
<223> OTHER INFORMATION: Xaa may be G or E
<220> FEATURE:
<221> NAME/KEY: MISC_FEATURE
<222> LOCATION: (43)..(43)
<223> OTHER INFORMATION: Xaa may be a basic amino acid
<220> FEATURE:
<221> NAME/KEY: MISC_FEATURE
<222> LOCATION: (48)..(48)
<223> OTHER INFORMATION: Xaa may be an hydrophobic amino acid
<220> FEATURE:
<221> NAME/KEY: MISC_FEATURE
<222> LOCATION: (67)..(67)
<223> OTHER INFORMATION: Xaa may be a basic amino acid
<220> FEATURE:
<221> NAME/KEY: MISC_FEATURE
<222> LOCATION: (68)..(68)
<223> OTHER INFORMATION: Xaa may be an hydrophobic amino acid
<220> FEATURE:
<221> NAME/KEY: MISC_FEATURE
<222> LOCATION: (76)..(76)
<223> OTHER INFORMATION: Xaa may be a neutral hydrophilic amino acid
<220> FEATURE:
<221> NAME/KEY: MISC_FEATURE
<222> LOCATION: (77)..(77)
<223> OTHER INFORMATION: Xaa may be D or N
<220> FEATURE:
<221> NAME/KEY: MISC_FEATURE
<222> LOCATION: (81)..(81)
<223> OTHER INFORMATION: Xaa may be an hydrophobic amino acid
<220> FEATURE:
<221> NAME/KEY: MISC_FEATURE
<222> LOCATION: (82)..(82)
<223> OTHER INFORMATION: Xaa may be E or Q
<220> FEATURE:
<221> NAME/KEY: MISC_FEATURE
<222> LOCATION: (87)..(87)
<223> OTHER INFORMATION: Xaa may be R or T
<220> FEATURE:
<221> NAME/KEY: MISC_FEATURE
<222> LOCATION: (112)..(112)
<223> OTHER INFORMATION: Xaa may be L or S

<400> SEQUENCE: 31

Xaa Val Gln Leu Xaa Gln Ser Gly Ala Glu Xaa Xaa Lys Pro Gly Ala
  1               5                  10                  15

Xaa Val Xaa Xaa Ser Cys Xaa Xaa Ser Gly Phe Asn Ile Lys Asp Ile
             20                  25                  30

Tyr Met His Trp Val Xaa Gln Xaa Pro Xaa Xaa Gly Leu Glu Trp Xaa
         35                  40                  45

Gly Arg Ile Asp Pro Ala Tyr Gly Asn Thr Lys Tyr Asp Pro Lys Phe
     50                  55                  60

Gln Gly Xaa Xaa Thr Ile Thr Ala Asp Thr Ser Xaa Xaa Thr Ala Tyr
 65                  70                  75                  80

Xaa Xaa Leu Ser Ser Leu Xaa Ser Glu Asp Thr Ala Val Tyr Tyr Cys
                 85                  90                  95

Ala Arg Arg Tyr Asp Thr Ala Met Asp Tyr Trp Gly Gln Gly Thr Xaa
            100                 105                 110

Val Thr Val Ser Ser
        115

<210> SEQ ID NO 32
<211> LENGTH: 117
<212> TYPE: PRT
<213> ORGANISM: Artificial Sequence
<220> FEATURE:
<223> OTHER INFORMATION: 16B5 heavy chain variable region - consensus 3
<220> FEATURE:
<221> NAME/KEY: MISC_FEATURE
```

```
<222> LOCATION: (1)..(1)
<223> OTHER INFORMATION: Xaa may be Q or E
<220> FEATURE:
<221> NAME/KEY: MISC_FEATURE
<222> LOCATION: (5)..(5)
<223> OTHER INFORMATION: Xaa may be V or Q
<220> FEATURE:
<221> NAME/KEY: MISC_FEATURE
<222> LOCATION: (11)..(11)
<223> OTHER INFORMATION: Xaa may be V or L
<220> FEATURE:
<221> NAME/KEY: MISC_FEATURE
<222> LOCATION: (12)..(12)
<223> OTHER INFORMATION: Xaa may be K or V
<220> FEATURE:
<221> NAME/KEY: MISC_FEATURE
<222> LOCATION: (17)..(17)
<223> OTHER INFORMATION: Xaa may be T or S
<220> FEATURE:
<221> NAME/KEY: MISC_FEATURE
<222> LOCATION: (19)..(19)
<223> OTHER INFORMATION: Xaa may be K or R
<220> FEATURE:
<221> NAME/KEY: MISC_FEATURE
<222> LOCATION: (20)..(20)
<223> OTHER INFORMATION: Xaa may be I or L
<220> FEATURE:
<221> NAME/KEY: MISC_FEATURE
<222> LOCATION: (23)..(23)
<223> OTHER INFORMATION: Xaa may be K or T
<220> FEATURE:
<221> NAME/KEY: MISC_FEATURE
<222> LOCATION: (24)..(24)
<223> OTHER INFORMATION: Xaa may be V or T
<220> FEATURE:
<221> NAME/KEY: MISC_FEATURE
<222> LOCATION: (38)..(38)
<223> OTHER INFORMATION: Xaa may be Q or K
<220> FEATURE:
<221> NAME/KEY: MISC_FEATURE
<222> LOCATION: (40)..(40)
<223> OTHER INFORMATION: Xaa may be A or R
<220> FEATURE:
<221> NAME/KEY: MISC_FEATURE
<222> LOCATION: (42)..(42)
<223> OTHER INFORMATION: Xaa may be G or E
<220> FEATURE:
<221> NAME/KEY: MISC_FEATURE
<222> LOCATION: (43)..(43)
<223> OTHER INFORMATION: Xaa may be K or Q
<220> FEATURE:
<221> NAME/KEY: MISC_FEATURE
<222> LOCATION: (48)..(48)
<223> OTHER INFORMATION: Xaa may be M or I
<220> FEATURE:
<221> NAME/KEY: MISC_FEATURE
<222> LOCATION: (67)..(67)
<223> OTHER INFORMATION: Xaa may be R or K
<220> FEATURE:
<221> NAME/KEY: MISC_FEATURE
<222> LOCATION: (68)..(68)
<223> OTHER INFORMATION: Xaa may be V or A
<220> FEATURE:
<221> NAME/KEY: MISC_FEATURE
<222> LOCATION: (76)..(76)
<223> OTHER INFORMATION: Xaa may be T or S
<220> FEATURE:
<221> NAME/KEY: MISC_FEATURE
<222> LOCATION: (77)..(77)
<223> OTHER INFORMATION: Xaa may be D or N
<220> FEATURE:
<221> NAME/KEY: MISC_FEATURE
<222> LOCATION: (81)..(81)
<223> OTHER INFORMATION: Xaa may be M or L
<220> FEATURE:
<221> NAME/KEY: MISC_FEATURE
<222> LOCATION: (82)..(82)
<223> OTHER INFORMATION: Xaa may be E or Q
<220> FEATURE:
```

```
<221> NAME/KEY: MISC_FEATURE
<222> LOCATION: (87)..(87)
<223> OTHER INFORMATION: Xaa may be R or T
<220> FEATURE:
<221> NAME/KEY: MISC_FEATURE
<222> LOCATION: (112)..(112)
<223> OTHER INFORMATION: Xaa may be L or S

<400> SEQUENCE: 32

Xaa Val Gln Leu Xaa Gln Ser Gly Ala Glu Xaa Xaa Lys Pro Gly Ala
1               5                   10                  15

Xaa Val Xaa Xaa Ser Cys Xaa Xaa Ser Gly Phe Asn Ile Lys Asp Ile
            20                  25                  30

Tyr Met His Trp Val Xaa Gln Xaa Pro Xaa Xaa Gly Leu Glu Trp Xaa
        35                  40                  45

Gly Arg Ile Asp Pro Ala Tyr Gly Asn Thr Lys Tyr Asp Pro Lys Phe
    50                  55                  60

Gln Gly Xaa Xaa Thr Ile Thr Ala Asp Thr Ser Xaa Xaa Thr Ala Tyr
65              70                  75                  80

Xaa Xaa Leu Ser Ser Leu Xaa Ser Glu Asp Thr Ala Val Tyr Tyr Cys
                85                  90                  95

Ala Arg Arg Tyr Asp Thr Ala Met Asp Tyr Trp Gly Gln Gly Thr Xaa
            100                 105                 110

Val Thr Val Ser Ser
        115

<210> SEQ ID NO 33
<211> LENGTH: 113
<212> TYPE: PRT
<213> ORGANISM: Artificial Sequence
<220> FEATURE:
<223> OTHER INFORMATION: murine 21B12 light chain variable region

<400> SEQUENCE: 33

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Arg Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65              70                  75                  80

Ile Ser Ser Val Lys Ala Glu Asp Leu Ala Val Tyr Tyr Cys Gln Gln
                85                  90                  95

Tyr Tyr Ile Tyr Pro Arg Thr Phe Gly Gly Gly Thr Lys Leu Glu Ile
            100                 105                 110

Lys

<210> SEQ ID NO 34
<211> LENGTH: 113
<212> TYPE: PRT
<213> ORGANISM: Artificial Sequence
<220> FEATURE:
<223> OTHER INFORMATION: 21B12 light chain variable region - consensus 1
<220> FEATURE:
<221> NAME/KEY: MISC_FEATURE
<222> LOCATION: (5)..(5)
<223> OTHER INFORMATION: Xaa is a conservative amino acid substitution
      in comparison with SEQ ID NO.:33
```

```
<220> FEATURE:
<221> NAME/KEY: MISC_FEATURE
<222> LOCATION: (9)..(9)
<223> OTHER INFORMATION: Xaa is a conservative amino acid substitution
      in comparison with SEQ ID NO.:33
<220> FEATURE:
<221> NAME/KEY: MISC_FEATURE
<222> LOCATION: (15)..(15)
<223> OTHER INFORMATION: Xaa is a conservative amino acid substitution
      in comparison with SEQ ID NO.:33
<220> FEATURE:
<221> NAME/KEY: MISC_FEATURE
<222> LOCATION: (18)..(18)
<223> OTHER INFORMATION: Xaa is a conservative amino acid substitution
      in comparison with SEQ ID NO.:33
<220> FEATURE:
<221> NAME/KEY: MISC_FEATURE
<222> LOCATION: (19)..(19)
<223> OTHER INFORMATION: Xaa is a conservative amino acid substitution
      in comparison with SEQ ID NO.:33
<220> FEATURE:
<221> NAME/KEY: MISC_FEATURE
<222> LOCATION: (21)..(21)
<223> OTHER INFORMATION: Xaa is a conservative amino acid substitution
      in comparison with SEQ ID NO.:33
<220> FEATURE:
<221> NAME/KEY: MISC_FEATURE
<222> LOCATION: (22)..(22)
<223> OTHER INFORMATION: Xaa is a conservative amino acid substitution
      in comparison with SEQ ID NO.:33
<220> FEATURE:
<221> NAME/KEY: MISC_FEATURE
<222> LOCATION: (45)..(45)
<223> OTHER INFORMATION: Xaa is a conservative amino acid substitution
      in comparison with SEQ ID NO.:33
<220> FEATURE:
<221> NAME/KEY: MISC_FEATURE
<222> LOCATION: (49)..(49)
<223> OTHER INFORMATION: Xaa is a conservative amino acid substitution
      in comparison with SEQ ID NO.:33
<220> FEATURE:
<221> NAME/KEY: MISC_FEATURE
<222> LOCATION: (69)..(69)
<223> OTHER INFORMATION: Xaa is a conservative amino acid substitution
      in comparison with SEQ ID NO.:33
<220> FEATURE:
<221> NAME/KEY: MISC_FEATURE
<222> LOCATION: (84)..(84)
<223> OTHER INFORMATION: Xaa is a conservative amino acid substitution
      in comparison with SEQ ID NO.:33
<220> FEATURE:
<221> NAME/KEY: MISC_FEATURE
<222> LOCATION: (85)..(85)
<223> OTHER INFORMATION: Xaa is a conservative amino acid substitution
      in comparison with SEQ ID NO.:33
<220> FEATURE:
<221> NAME/KEY: MISC_FEATURE
<222> LOCATION: (89)..(89)
<223> OTHER INFORMATION: Xaa is a conservative amino acid substitution
      in comparison with SEQ ID NO.:33
<220> FEATURE:
<221> NAME/KEY: MISC_FEATURE
<222> LOCATION: (106)..(106)
<223> OTHER INFORMATION: Xaa is a conservative amino acid substitution
      in comparison with SEQ ID NO.:33

<400> SEQUENCE: 34

Asp Ile Val Met Xaa Gln Ser Pro Xaa Ser Leu Ala Val Ser Xaa Gly
1               5                   10                  15

Glu Xaa Xaa Thr Xaa Xaa Cys Lys Ser Ser Gln Ser Leu Leu Tyr Ser
            20                  25                  30

Ser Asn Gln Lys Asn Tyr Leu Ala Trp Tyr Gln Gln Xaa Pro Gly Gln
        35                  40                  45

Xaa Pro Lys Leu Leu Ile Tyr Trp Ala Ser Thr Arg Glu Ser Gly Val
    50                  55                  60
```

```
Pro Asp Arg Phe Xaa Gly Ser Gly Ser Gly Thr Asp Phe Thr Leu Thr
65                  70                  75                  80

Ile Ser Ser Xaa Xaa Ala Glu Asp Xaa Ala Val Tyr Tyr Cys Gln Gln
                85                  90                  95

Tyr Tyr Ile Tyr Pro Arg Thr Phe Gly Xaa Gly Thr Lys Leu Glu Ile
            100                 105                 110

Lys

<210> SEQ ID NO 35
<211> LENGTH: 113
<212> TYPE: PRT
<213> ORGANISM: Artificial Sequence
<220> FEATURE:
<223> OTHER INFORMATION: 21B12 light chain variable region - consensus 2
<220> FEATURE:
<221> NAME/KEY: MISC_FEATURE
<222> LOCATION: (5)..(5)
<223> OTHER INFORMATION: Xaa may be a neutral hydrophilic amino acid
<220> FEATURE:
<221> NAME/KEY: MISC_FEATURE
<222> LOCATION: (9)..(9)
<223> OTHER INFORMATION: Xaa may be D or S
<220> FEATURE:
<221> NAME/KEY: MISC_FEATURE
<222> LOCATION: (15)..(15)
<223> OTHER INFORMATION: Xaa may be an hydrophobic amino acid
<220> FEATURE:
<221> NAME/KEY: MISC_FEATURE
<222> LOCATION: (18)..(18)
<223> OTHER INFORMATION: Xaa may be a basic amino acid
<220> FEATURE:
<221> NAME/KEY: MISC_FEATURE
<222> LOCATION: (19)..(19)
<223> OTHER INFORMATION: Xaa may be an hydrophobic amino acid
<220> FEATURE:
<221> NAME/KEY: MISC_FEATURE
<222> LOCATION: (21)..(21)
<223> OTHER INFORMATION: Xaa may be an hydrophobic amino acid
<220> FEATURE:
<221> NAME/KEY: MISC_FEATURE
<222> LOCATION: (22)..(22)
<223> OTHER INFORMATION: Xaa may be N or S
<220> FEATURE:
<221> NAME/KEY: MISC_FEATURE
<222> LOCATION: (45)..(45)
<223> OTHER INFORMATION: Xaa may be a basic amino acid
<220> FEATURE:
<221> NAME/KEY: MISC_FEATURE
<222> LOCATION: (49)..(49)
<223> OTHER INFORMATION: Xaa may be P or S
<220> FEATURE:
<221> NAME/KEY: MISC_FEATURE
<222> LOCATION: (69)..(69)
<223> OTHER INFORMATION: Xaa may be neutral hydrophilic amino acid
<220> FEATURE:
<221> NAME/KEY: MISC_FEATURE
<222> LOCATION: (84)..(84)
<223> OTHER INFORMATION: Xaa may be an hydrophobic amino acid
<220> FEATURE:
<221> NAME/KEY: MISC_FEATURE
<222> LOCATION: (85)..(85)
<223> OTHER INFORMATION: Xaa may be a basic amino acid
<220> FEATURE:
<221> NAME/KEY: MISC_FEATURE
<222> LOCATION: (89)..(89)
<223> OTHER INFORMATION: Xaa may be an hydrophobic amino acid
<220> FEATURE:
<221> NAME/KEY: MISC_FEATURE
<222> LOCATION: (106)..(106)
<223> OTHER INFORMATION: Xaa may be Q or G

<400> SEQUENCE: 35

Asp Ile Val Met Xaa Gln Ser Pro Xaa Ser Leu Ala Val Ser Xaa Gly
```

```
               1               5                  10                 15
             Glu Xaa Xaa Thr Xaa Xaa Cys Lys Ser Ser Gln Ser Leu Leu Tyr Ser
                          20                  25                  30

Ser Asn Gln Lys Asn Tyr Leu Ala Trp Tyr Gln Gln Xaa Pro Gly Gln
                          35                  40                  45

Xaa Pro Lys Leu Leu Ile Tyr Trp Ala Ser Thr Arg Glu Ser Gly Val
                          50                  55                  60

Pro Asp Arg Phe Xaa Gly Ser Gly Ser Gly Thr Asp Phe Thr Leu Thr
              65              70                  75                  80

Ile Ser Ser Xaa Xaa Ala Glu Asp Xaa Ala Val Tyr Tyr Cys Gln Gln
                          85                  90                  95

Tyr Tyr Ile Tyr Pro Arg Thr Phe Gly Xaa Gly Thr Lys Leu Glu Ile
                          100                 105                 110

Lys
```

<210> SEQ ID NO 36
<211> LENGTH: 113
<212> TYPE: PRT
<213> ORGANISM: Artificial Sequence
<220> FEATURE:
<223> OTHER INFORMATION: 21B12 light chain variable region - consensus 3
<220> FEATURE:
<221> NAME/KEY: MISC_FEATURE
<222> LOCATION: (5)..(5)
<223> OTHER INFORMATION: Xaa may be T or S
<220> FEATURE:
<221> NAME/KEY: MISC_FEATURE
<222> LOCATION: (9)..(9)
<223> OTHER INFORMATION: Xaa may be D or S
<220> FEATURE:
<221> NAME/KEY: MISC_FEATURE
<222> LOCATION: (15)..(15)
<223> OTHER INFORMATION: Xaa may be L or V
<220> FEATURE:
<221> NAME/KEY: MISC_FEATURE
<222> LOCATION: (18)..(18)
<223> OTHER INFORMATION: Xaa may be R or K
<220> FEATURE:
<221> NAME/KEY: MISC_FEATURE
<222> LOCATION: (19)..(19)
<223> OTHER INFORMATION: Xaa may be A or V
<220> FEATURE:
<221> NAME/KEY: MISC_FEATURE
<222> LOCATION: (21)..(21)
<223> OTHER INFORMATION: Xaa may be I or M
<220> FEATURE:
<221> NAME/KEY: MISC_FEATURE
<222> LOCATION: (22)..(22)
<223> OTHER INFORMATION: Xaa may be N or S
<220> FEATURE:
<221> NAME/KEY: MISC_FEATURE
<222> LOCATION: (45)..(45)
<223> OTHER INFORMATION: Xaa may be K or R
<220> FEATURE:
<221> NAME/KEY: MISC_FEATURE
<222> LOCATION: (49)..(49)
<223> OTHER INFORMATION: Xaa may be P or S
<220> FEATURE:
<221> NAME/KEY: MISC_FEATURE
<222> LOCATION: (69)..(69)
<223> OTHER INFORMATION: Xaa may be S or T
<220> FEATURE:
<221> NAME/KEY: MISC_FEATURE
<222> LOCATION: (84)..(84)
<223> OTHER INFORMATION: Xaa may be L or V
<220> FEATURE:
<221> NAME/KEY: MISC_FEATURE
<222> LOCATION: (85)..(85)
<223> OTHER INFORMATION: Xaa may be Q or K
<220> FEATURE:
<221> NAME/KEY: MISC_FEATURE
<222> LOCATION: (89)..(89)
<223> OTHER INFORMATION: Xaa may be V or L
<220> FEATURE:
<221> NAME/KEY: MISC_FEATURE
<222> LOCATION: (106)..(106)
<223> OTHER INFORMATION: Xaa may be Q or G

<400> SEQUENCE: 36

Asp Ile Val Met Xaa Gln Ser Pro Xaa Ser Leu Ala Val Ser Xaa Gly
1               5                   10                  15

Glu Xaa Xaa Thr Xaa Xaa Cys Lys Ser Gln Ser Leu Leu Tyr Ser
            20                  25                  30

Ser Asn Gln Lys Asn Tyr Leu Ala Trp Tyr Gln Xaa Pro Gly Gln
        35                  40                  45

Xaa Pro Lys Leu Leu Ile Tyr Trp Ala Ser Thr Arg Glu Ser Gly Val
    50                  55                  60

Pro Asp Arg Phe Xaa Gly Ser Gly Ser Gly Thr Asp Phe Thr Leu Thr
65                  70                  75                  80

Ile Ser Ser Xaa Xaa Ala Glu Asp Xaa Ala Val Tyr Tyr Cys Gln Gln
                85                  90                  95

Tyr Tyr Ile Tyr Pro Arg Thr Phe Gly Xaa Gly Thr Lys Leu Glu Ile
            100                 105                 110

Lys

<210> SEQ ID NO 37
<211> LENGTH: 118
<212> TYPE: PRT
<213> ORGANISM: Artificial Sequence
<220> FEATURE:
<223> OTHER INFORMATION: murine 21B12 heavy chain variable region

<400> SEQUENCE: 37

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met His Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Asp Gly Phe Leu Tyr Phe Phe Asp Tyr Trp Gly Gln Gly Thr
            100                 105                 110

Thr Leu Thr Val Ser Ser
        115

<210> SEQ ID NO 38
<211> LENGTH: 118
<212> TYPE: PRT
<213> ORGANISM: Artificial Sequence
<220> FEATURE:
<223> OTHER INFORMATION: 21B12 heavy chain variable region - consensus 1
<220> FEATURE:
<221> NAME/KEY: MISC_FEATURE
<222> LOCATION: (2)..(2)
<223> OTHER INFORMATION: Xaa is an amino acid substitution in comparison
      with SEQ ID NO.:37
<220> FEATURE:

-continued

```
<221> NAME/KEY: MISC_FEATURE
<222> LOCATION: (9)..(9)
<223> OTHER INFORMATION: Xaa is an amino acid substitution in comparison
      with SEQ ID NO.:37
<220> FEATURE:
<221> NAME/KEY: MISC_FEATURE
<222> LOCATION: (16)..(16)
<223> OTHER INFORMATION: Xaa is an amino acid substitution in comparison
      with SEQ ID NO.:37
<220> FEATURE:
<221> NAME/KEY: MISC_FEATURE
<222> LOCATION: (17)..(17)
<223> OTHER INFORMATION: Xaa is an amino acid substitution in comparison
      with SEQ ID NO.:37
<220> FEATURE:
<221> NAME/KEY: MISC_FEATURE
<222> LOCATION: (20)..(20)
<223> OTHER INFORMATION: Xaa is an amino acid substitution in comparison
      with SEQ ID NO.:37
<220> FEATURE:
<221> NAME/KEY: MISC_FEATURE
<222> LOCATION: (38)..(38)
<223> OTHER INFORMATION: Xaa is an amino acid substitution in comparison
      with SEQ ID NO.:37
<220> FEATURE:
<221> NAME/KEY: MISC_FEATURE
<222> LOCATION: (43)..(43)
<223> OTHER INFORMATION: Xaa is an amino acid substitution in comparison
      with SEQ ID NO.:37
<220> FEATURE:
<221> NAME/KEY: MISC_FEATURE
<222> LOCATION: (46)..(46)
<223> OTHER INFORMATION: Xaa is an amino acid substitution in comparison
      with SEQ ID NO.:37
<220> FEATURE:
<221> NAME/KEY: MISC_FEATURE
<222> LOCATION: (69)..(69)
<223> OTHER INFORMATION: Xaa is an amino acid substitution in comparison
      with SEQ ID NO.:37
<220> FEATURE:
<221> NAME/KEY: MISC_FEATURE
<222> LOCATION: (73)..(73)
<223> OTHER INFORMATION: Xaa is an amino acid substitution in comparison
      with SEQ ID NO.:37
<220> FEATURE:
<221> NAME/KEY: MISC_FEATURE
<222> LOCATION: (76)..(76)
<223> OTHER INFORMATION: Xaa is an amino acid substitution in comparison
      with SEQ ID NO.:37
<220> FEATURE:
<221> NAME/KEY: MISC_FEATURE
<222> LOCATION: (84)..(84)
<223> OTHER INFORMATION: Xaa is an amino acid substitution in comparison
      with SEQ ID NO.:37
<220> FEATURE:
<221> NAME/KEY: MISC_FEATURE
<222> LOCATION: (85)..(85)
<223> OTHER INFORMATION: Xaa is an amino acid substitution in comparison
      with SEQ ID NO.:37
<220> FEATURE:
<221> NAME/KEY: MISC_FEATURE
<222> LOCATION: (88)..(88)
<223> OTHER INFORMATION: Xaa is an amino acid substitution in comparison
      with SEQ ID NO.:37
<220> FEATURE:
<221> NAME/KEY: MISC_FEATURE
<222> LOCATION: (93)..(93)
<223> OTHER INFORMATION: Xaa is an amino acid substitution in comparison
      with SEQ ID NO.:37
<220> FEATURE:
<221> NAME/KEY: MISC_FEATURE
<222> LOCATION: (95)..(95)
<223> OTHER INFORMATION: Xaa is an amino acid substitution in comparison
      with SEQ ID NO.:37
<220> FEATURE:
<221> NAME/KEY: MISC_FEATURE
<222> LOCATION: (113)..(113)
<223> OTHER INFORMATION: Xaa is an amino acid substitution in comparison
      with SEQ ID NO.:37
```

```
<220> FEATURE:
<221> NAME/KEY: MISC_FEATURE
<222> LOCATION: (114)..(114)
<223> OTHER INFORMATION: Xaa is an amino acid substitution in comparison
      with SEQ ID NO.:37

<400> SEQUENCE: 38

Gln Xaa Gln Leu Val Gln Ser Gly Xaa Glu Leu Lys Lys Pro Gly Xaa
1               5                   10                  15

Xaa Val Lys Xaa Ser Cys Lys Ala Ser Gly Tyr Thr Phe Thr Asn Tyr
            20                  25                  30

Gly Met His Trp Val Xaa Gln Ala Pro Gly Xaa Gly Leu Xaa Trp Met
            35                  40                  45

Gly Trp Ile Asn Thr Tyr Thr Gly Glu Pro Thr Tyr Ala Asp Asp Phe
50                  55                  60

Lys Gly Arg Phe Xaa Phe Ser Leu Xaa Thr Ser Xaa Ser Thr Ala Tyr
65                  70                  75                  80

Leu Gln Ile Xaa Xaa Leu Lys Xaa Glu Asp Thr Ala Xaa Tyr Xaa Cys
                85                  90                  95

Ala Arg Asp Gly Phe Leu Tyr Phe Phe Asp Tyr Trp Gly Gln Gly Thr
                100                 105                 110

Xaa Xaa Thr Val Ser Ser
        115

<210> SEQ ID NO 39
<211> LENGTH: 118
<212> TYPE: PRT
<213> ORGANISM: Artificial Sequence
<220> FEATURE:
<223> OTHER INFORMATION: 21B12 heavy chain variable region - consensus 2
<220> FEATURE:
<221> NAME/KEY: MISC_FEATURE
<222> LOCATION: (2)..(2)
<223> OTHER INFORMATION: Xaa may be an hydrophobic amino acid
<220> FEATURE:
<221> NAME/KEY: MISC_FEATURE
<222> LOCATION: (9)..(9)
<223> OTHER INFORMATION: Xaa may be S or P
<220> FEATURE:
<221> NAME/KEY: MISC_FEATURE
<222> LOCATION: (16)..(16)
<223> OTHER INFORMATION: Xaa may be A or E
<220> FEATURE:
<221> NAME/KEY: MISC_FEATURE
<222> LOCATION: (17)..(17)
<223> OTHER INFORMATION: Xaa may be neutral hydrophilic amino acid
<220> FEATURE:
<221> NAME/KEY: MISC_FEATURE
<222> LOCATION: (20)..(20)
<223> OTHER INFORMATION: Xaa may be an hydrophobic amino acid
<220> FEATURE:
<221> NAME/KEY: MISC_FEATURE
<222> LOCATION: (38)..(38)
<223> OTHER INFORMATION: Xaa may be basic amino acid
<220> FEATURE:
<221> NAME/KEY: MISC_FEATURE
<222> LOCATION: (43)..(43)
<223> OTHER INFORMATION: Xaa may be basic amino acid
<220> FEATURE:
<221> NAME/KEY: MISC_FEATURE
<222> LOCATION: (46)..(46)
<223> OTHER INFORMATION: Xaa may be E or K
<220> FEATURE:
<221> NAME/KEY: MISC_FEATURE
<222> LOCATION: (69)..(69)
<223> OTHER INFORMATION: Xaa may be an hydrophobic amino acid
<220> FEATURE:
<221> NAME/KEY: MISC_FEATURE
<222> LOCATION: (73)..(73)
<223> OTHER INFORMATION: Xaa may be an acidic amino acid
```

```
<220> FEATURE:
<221> NAME/KEY: MISC_FEATURE
<222> LOCATION: (76)..(76)
<223> OTHER INFORMATION: Xaa may be an hydrophobic amino acid
<220> FEATURE:
<221> NAME/KEY: MISC_FEATURE
<222> LOCATION: (84)..(84)
<223> OTHER INFORMATION: Xaa may be S or N
<220> FEATURE:
<221> NAME/KEY: MISC_FEATURE
<222> LOCATION: (85)..(85)
<223> OTHER INFORMATION: Xaa may be S or N
<220> FEATURE:
<221> NAME/KEY: MISC_FEATURE
<222> LOCATION: (88)..(88)
<223> OTHER INFORMATION: Xaa may be A or N
<220> FEATURE:
<221> NAME/KEY: MISC_FEATURE
<222> LOCATION: (93)..(93)
<223> OTHER INFORMATION: Xaa may be V or T
<220> FEATURE:
<221> NAME/KEY: MISC_FEATURE
<222> LOCATION: (95)..(95)
<223> OTHER INFORMATION: Xaa may be an aromatic amino acid
<220> FEATURE:
<221> NAME/KEY: MISC_FEATURE
<222> LOCATION: (113)..(113)
<223> OTHER INFORMATION: Xaa may be L or T
<220> FEATURE:
<221> NAME/KEY: MISC_FEATURE
<222> LOCATION: (114)..(114)
<223> OTHER INFORMATION: Xaa may be an hydrophobic amino acid

<400> SEQUENCE: 39

Gln Xaa Gln Leu Val Gln Ser Gly Xaa Glu Leu Lys Lys Pro Gly Xaa
1               5                   10                  15

Xaa Val Lys Xaa Ser Cys Lys Ala Ser Gly Tyr Thr Phe Thr Asn Tyr
            20                  25                  30

Gly Met His Trp Val Xaa Gln Ala Pro Gly Xaa Gly Leu Xaa Trp Met
        35                  40                  45

Gly Trp Ile Asn Thr Tyr Thr Gly Glu Pro Thr Tyr Ala Asp Asp Phe
    50                  55                  60

Lys Gly Arg Phe Xaa Phe Ser Leu Xaa Thr Ser Xaa Ser Thr Ala Tyr
65                  70                  75                  80

Leu Gln Ile Xaa Xaa Leu Lys Xaa Glu Asp Thr Ala Xaa Tyr Xaa Cys
                85                  90                  95

Ala Arg Asp Gly Phe Leu Tyr Phe Phe Asp Tyr Trp Gly Gln Gly Thr
            100                 105                 110

Xaa Xaa Thr Val Ser Ser
        115

<210> SEQ ID NO 40
<211> LENGTH: 118
<212> TYPE: PRT
<213> ORGANISM: Artificial Sequence
<220> FEATURE:
<223> OTHER INFORMATION: 21B12 heavy chain variable region - consensus 3
<220> FEATURE:
<221> NAME/KEY: MISC_FEATURE
<222> LOCATION: (2)..(2)
<223> OTHER INFORMATION: Xaa may be V or I
<220> FEATURE:
<221> NAME/KEY: MISC_FEATURE
<222> LOCATION: (9)..(9)
<223> OTHER INFORMATION: Xaa may be S or P
<220> FEATURE:
<221> NAME/KEY: MISC_FEATURE
<222> LOCATION: (16)..(16)
<223> OTHER INFORMATION: Xaa may be A or E
<220> FEATURE:
```

```
<221> NAME/KEY: MISC_FEATURE
<222> LOCATION: (17)..(17)
<223> OTHER INFORMATION: Xaa may be S or T
<220> FEATURE:
<221> NAME/KEY: MISC_FEATURE
<222> LOCATION: (20)..(20)
<223> OTHER INFORMATION: Xaa may be V or I
<220> FEATURE:
<221> NAME/KEY: MISC_FEATURE
<222> LOCATION: (38)..(38)
<223> OTHER INFORMATION: Xaa may be R or K
<220> FEATURE:
<221> NAME/KEY: MISC_FEATURE
<222> LOCATION: (43)..(43)
<223> OTHER INFORMATION: Xaa may be Q or K
<220> FEATURE:
<221> NAME/KEY: MISC_FEATURE
<222> LOCATION: (46)..(46)
<223> OTHER INFORMATION: Xaa may be E or K
<220> FEATURE:
<221> NAME/KEY: MISC_FEATURE
<222> LOCATION: (69)..(69)
<223> OTHER INFORMATION: Xaa may be V or A
<220> FEATURE:
<221> NAME/KEY: MISC_FEATURE
<222> LOCATION: (73)..(73)
<223> OTHER INFORMATION: Xaa may be D or E
<220> FEATURE:
<221> NAME/KEY: MISC_FEATURE
<222> LOCATION: (76)..(76)
<223> OTHER INFORMATION: Xaa may be V or A
<220> FEATURE:
<221> NAME/KEY: MISC_FEATURE
<222> LOCATION: (84)..(84)
<223> OTHER INFORMATION: Xaa may be S or N
<220> FEATURE:
<221> NAME/KEY: MISC_FEATURE
<222> LOCATION: (85)..(85)
<223> OTHER INFORMATION: Xaa may be S or N
<220> FEATURE:
<221> NAME/KEY: MISC_FEATURE
<222> LOCATION: (88)..(88)
<223> OTHER INFORMATION: Xaa may be A or N
<220> FEATURE:
<221> NAME/KEY: MISC_FEATURE
<222> LOCATION: (93)..(93)
<223> OTHER INFORMATION: Xaa may be V or T
<220> FEATURE:
<221> NAME/KEY: MISC_FEATURE
<222> LOCATION: (95)..(95)
<223> OTHER INFORMATION: Xaa may be Y or F
<220> FEATURE:
<221> NAME/KEY: MISC_FEATURE
<222> LOCATION: (113)..(113)
<223> OTHER INFORMATION: Xaa may be L or T
<220> FEATURE:
<221> NAME/KEY: MISC_FEATURE
<222> LOCATION: (114)..(114)
<223> OTHER INFORMATION: Xaa may be V or L

<400> SEQUENCE: 40

Gln Xaa Gln Leu Val Gln Ser Gly Xaa Glu Leu Lys Lys Pro Gly Xaa
1               5                   10                  15

Xaa Val Lys Xaa Ser Cys Lys Ala Ser Gly Tyr Thr Phe Thr Asn Tyr
            20                  25                  30

Gly Met His Trp Val Xaa Gln Ala Pro Gly Xaa Gly Leu Xaa Trp Met
        35                  40                  45

Gly Trp Ile Asn Thr Tyr Thr Gly Glu Pro Thr Tyr Ala Asp Asp Phe
    50                  55                  60

Lys Gly Arg Phe Xaa Phe Ser Leu Xaa Thr Ser Xaa Ser Thr Ala Tyr
65                  70                  75                  80

Leu Gln Ile Xaa Xaa Leu Lys Xaa Glu Asp Thr Ala Xaa Tyr Xaa Cys
                85                  90                  95
```

```
Ala Arg Asp Gly Phe Leu Tyr Phe Phe Asp Tyr Trp Gly Gln Gly Thr
            100                 105                 110

Xaa Xaa Thr Val Ser Ser
        115

<210> SEQ ID NO 41
<211> LENGTH: 113
<212> TYPE: PRT
<213> ORGANISM: Homo sapiens

<400> SEQUENCE: 41

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Ser Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Ser Phe Gly Gln Gly Thr Lys Leu Glu Ile
            100                 105                 110

Lys

<210> SEQ ID NO 42
<211> LENGTH: 117
<212> TYPE: PRT
<213> ORGANISM: Homo sapiens

<400> SEQUENCE: 42

Gln Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Pro Leu Phe Gly Arg Asp His Trp Gly Gln Gly Thr Leu
            100                 105                 110

Val Thr Val Ser Arg
        115

<210> SEQ ID NO 43
<211> LENGTH: 113
<212> TYPE: PRT
<213> ORGANISM: Homo sapiens

<400> SEQUENCE: 43

Asp Ile Val Met Thr Gln Ser Pro Asp Ser Leu Ala Val Ser Leu Gly
```

```
            1               5                  10                  15
        Glu Arg Ala Thr Ile Asn Cys Lys Ser Ser Gln Ser Val Leu Tyr Ser
                        20                  25                  30

Ser Asn Ser Lys Asn Tyr Leu Ala Trp Tyr Gln Gln Lys Pro Gly Gln
                        35                  40                  45

Pro Pro Lys Leu Leu Ile Tyr Trp Ala Ser Thr Arg Glu Ser Gly Val
                        50                  55                  60

Pro Asp Arg Phe Ser Gly Ser Gly Ser Gly Thr Asp Phe Thr Leu Thr
        65                      70                  75                  80

Ile Ser Ser Leu Gln Ala Glu Asp Val Ala Val Tyr Tyr Cys Gln Gln
                        85                  90                  95

Tyr Tyr Ser Thr Pro Tyr Ser Phe Gly Gln Gly Thr Lys Leu Glu Ile
                        100                 105                 110

Lys

<210> SEQ ID NO 44
<211> LENGTH: 121
<212> TYPE: PRT
<213> ORGANISM: Homo sapiens

<400> SEQUENCE: 44

Gln Val Gln Leu Val Gln Ser Gly Ser Glu Leu Lys Lys Pro Gly Ala
        1               5                   10                  15

Ser Val Lys Val Ser Cys Lys Ala Ser Gly Tyr Thr Phe Thr Ser Tyr
                        20                  25                  30

Ala Met Asn Trp Val Arg Gln Ala Pro Gly Gln Gly Leu Glu Trp Met
                        35                  40                  45

Gly Trp Ile Asn Thr Asn Thr Gly Asn Pro Thr Tyr Ala Gln Gly Phe
                        50                  55                  60

Thr Gly Arg Phe Val Phe Ser Leu Asp Thr Ser Val Ser Thr Ala Tyr
        65                      70                  75                  80

Leu Gln Ile Ser Ser Leu Lys Ala Glu Asp Thr Ala Val Tyr Tyr Cys
                        85                  90                  95

Ala Arg Asp Trp Gly Gln Gly Thr Leu Val Thr Val Ser Ser Val Ala
                        100                 105                 110

Thr Ile Asp Glu Asn Trp Phe Asp Pro
                        115                 120

<210> SEQ ID NO 45
<211> LENGTH: 8
<212> TYPE: PRT
<213> ORGANISM: Artificial Sequence
<220> FEATURE:
<223> OTHER INFORMATION: 16B5 heavy chain CDR1- shorter version

<400> SEQUENCE: 45

Gly Phe Asn Ile Lys Asp Ile Tyr
        1               5

<210> SEQ ID NO 46
<211> LENGTH: 8
<212> TYPE: PRT
<213> ORGANISM: Artificial Sequence
<220> FEATURE:
<223> OTHER INFORMATION: 16B5 heavy chain CDR2- shorter version

<400> SEQUENCE: 46

Ile Asp Pro Ala Tyr Gly Asn Thr
        1               5
```

<210> SEQ ID NO 47
<211> LENGTH: 10
<212> TYPE: PRT
<213> ORGANISM: Artificial Sequence
<220> FEATURE:
<223> OTHER INFORMATION: 16B5 heavy chain CDR3

<400> SEQUENCE: 47

Ala Arg Arg Tyr Asp Thr Ala Met Asp Tyr
1               5                   10

<210> SEQ ID NO 48
<211> LENGTH: 12
<212> TYPE: PRT
<213> ORGANISM: Artificial Sequence
<220> FEATURE:
<223> OTHER INFORMATION: 16B5 light chain CDR1- shorter version

<400> SEQUENCE: 48

Gln Ser Leu Leu Asn Ser Arg Thr Arg Lys Asn Tyr
1               5                   10

<210> SEQ ID NO 49
<211> LENGTH: 3
<212> TYPE: PRT
<213> ORGANISM: Artificial Sequence
<220> FEATURE:
<223> OTHER INFORMATION: 16B5 light chain CDR2- shorter version

<400> SEQUENCE: 49

Trp Ala Ser
1

<210> SEQ ID NO 50
<211> LENGTH: 8
<212> TYPE: PRT
<213> ORGANISM: Artificial Sequence
<220> FEATURE:
<223> OTHER INFORMATION: 16B5 light chain CDR3

<400> SEQUENCE: 50

Lys Gln Ser Tyr Asn Leu Trp Thr
1               5

<210> SEQ ID NO 51
<211> LENGTH: 8
<212> TYPE: PRT
<213> ORGANISM: Artificial Sequence
<220> FEATURE:
<223> OTHER INFORMATION: 21B12 heavy chain CDR1

<400> SEQUENCE: 51

Gly Tyr Thr Phe Thr Asn Tyr Gly
1               5

<210> SEQ ID NO 52
<211> LENGTH: 8
<212> TYPE: PRT
<213> ORGANISM: Artificial Sequence
<220> FEATURE:
<223> OTHER INFORMATION: 21B12 heavy chain CDR2

<400> SEQUENCE: 52

Ile Asn Thr Tyr Thr Gly Glu Pro
1               5

```
<210> SEQ ID NO 53
<211> LENGTH: 11
<212> TYPE: PRT
<213> ORGANISM: Artificial Sequence
<220> FEATURE:
<223> OTHER INFORMATION: 21B12 heavy chain CDR3 consensus
<220> FEATURE:
<221> NAME/KEY: MISC_FEATURE
<222> LOCATION: (1)..(1)
<223> OTHER INFORMATION: Xaa is A
<220> FEATURE:
<221> NAME/KEY: MISC_FEATURE
<222> LOCATION: (2)..(2)
<223> OTHER INFORMATION: Xaa is R

<400> SEQUENCE: 53

Xaa Xaa Asp Gly Phe Leu Tyr Phe Phe Asp Tyr
1               5                   10

<210> SEQ ID NO 54
<211> LENGTH: 12
<212> TYPE: PRT
<213> ORGANISM: Artificial Sequence
<220> FEATURE:
<223> OTHER INFORMATION: 21B12 light chain CDR1

<400> SEQUENCE: 54

Gln Ser Leu Leu Tyr Ser Ser Asn Gln Lys Asn Tyr
1               5                   10

<210> SEQ ID NO 55
<211> LENGTH: 3
<212> TYPE: PRT
<213> ORGANISM: Artificial Sequence
<220> FEATURE:
<223> OTHER INFORMATION: 21B12 light chain CDR2

<400> SEQUENCE: 55

Trp Ala Ser
1

<210> SEQ ID NO 56
<211> LENGTH: 9
<212> TYPE: PRT
<213> ORGANISM: Artificial Sequence
<220> FEATURE:
<223> OTHER INFORMATION: 21B12 light chain CDR3

<400> SEQUENCE: 56

Gln Gln Tyr Tyr Ile Tyr Pro Arg Thr
1               5

<210> SEQ ID NO 57
<211> LENGTH: 21
<212> TYPE: DNA
<213> ORGANISM: Artificial Sequence
<220> FEATURE:
<223> OTHER INFORMATION: primer

<400> SEQUENCE: 57
gagcagagcg ctataaatac g                                               21

<210> SEQ ID NO 58
<211> LENGTH: 21
<212> TYPE: DNA
<213> ORGANISM: Artificial Sequence
<220> FEATURE:
<223> OTHER INFORMATION: primer
```

```
<400> SEQUENCE: 58
cacggtctcc ataaatttag g                                              21

<210> SEQ ID NO 59
<211> LENGTH: 32
<212> TYPE: DNA
<213> ORGANISM: Artificial Sequence
<220> FEATURE:
<223> OTHER INFORMATION: primer

<400> SEQUENCE: 59
ttgcggccgc aatacaatga gctgcgtgtg gc                                  32

<210> SEQ ID NO 60
<211> LENGTH: 24
<212> TYPE: DNA
<213> ORGANISM: Artificial Sequence
<220> FEATURE:
<223> OTHER INFORMATION: primer

<400> SEQUENCE: 60
gactcatcgt actcctgctt gctg                                           24

<210> SEQ ID NO 61
<211> LENGTH: 21
<212> TYPE: DNA
<213> ORGANISM: Artificial Sequence
<220> FEATURE:
<223> OTHER INFORMATION: primer

<400> SEQUENCE: 61
cagcagcaga gtcttcatca t                                              21

<210> SEQ ID NO 62
<211> LENGTH: 111
<212> TYPE: PRT
<213> ORGANISM: Artificial Sequence
<220> FEATURE:
<223> OTHER INFORMATION: 20E11 light chain variable region

<400> SEQUENCE: 62

Asp Ile Val Leu Thr Leu Ser Pro Ala Ser Leu Ala Val Ser Leu Gly
1               5                   10                  15

Gln Arg Ala Thr Ile Ser Cys Arg Ala Ser Gln Ser Val Asn Ser Ser
            20                  25                  30

Asn Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr His Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Trp Thr Phe Gly Gly Gly Thr Lys Leu Glu Ile Lys
            100                 105                 110

<210> SEQ ID NO 63
<211> LENGTH: 118
<212> TYPE: PRT
<213> ORGANISM: Artificial Sequence
<220> FEATURE:
<223> OTHER INFORMATION: 20E11 heavy chain variable region
```

<400> SEQUENCE: 63

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Thr Gly Ser Ser Gly Tyr Phe Asp Cys Trp Gly Gln Gly Thr
            100                 105                 110

Thr Leu Thr Val Ser Ser
            115

<210> SEQ ID NO 64
<211> LENGTH: 106
<212> TYPE: PRT
<213> ORGANISM: Artificial Sequence
<220> FEATURE:
<223> OTHER INFORMATION: 11E2 light chain variable region-Gr1

<400> SEQUENCE: 64

Glu Asn Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Ser Thr Ser Pro Lys Leu Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Met Glu Ala Glu
65                  70                  75                  80

Asp Val Ala Thr Tyr Tyr Cys Phe Gln Gly Ser Gly Tyr Pro Phe Thr
                85                  90                  95

Phe Gly Ser Gly Thr Lys Leu Glu Ile Lys
            100                 105

<210> SEQ ID NO 65
<211> LENGTH: 107
<212> TYPE: PRT
<213> ORGANISM: Artificial Sequence
<220> FEATURE:
<223> OTHER INFORMATION: 11E2 light chain variable region-Gr2

<400> SEQUENCE: 65

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Ala Trp Tyr Gln His Lys Pro Gly Lys Gly Pro Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Leu Arg
                85                  90                  95

Thr Phe Gly Gly Gly Thr Lys Leu Glu Ile Lys
            100                 105

<210> SEQ ID NO 66
<211> LENGTH: 120
<212> TYPE: PRT
<213> ORGANISM: Artificial Sequence
<220> FEATURE:
<223> OTHER INFORMATION: 11E2 heavy chain variable region

<400> SEQUENCE: 66

Glu Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
                20                  25                  30

Asn Met Asn Trp Val Lys Gln Asn Gly Lys Ser Leu Glu Trp Ile
            35                  40                  45

Gly Asn Ile Asp Pro Tyr Tyr Gly Thr Pro Asn Tyr Asn Gln Lys Phe
    50                  55                  60

Lys Gly Lys Ala Thr Leu Thr Val Asp Lys Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Leu Asn Ser Leu Leu Arg Leu Asn Ala Met Asp Tyr Trp Gly Gln
            100                 105                 110

Gly Thr Ser Val Thr Val Ser Ser
            115                 120

<210> SEQ ID NO 67
<211> LENGTH: 118
<212> TYPE: PRT
<213> ORGANISM: Artificial Sequence
<220> FEATURE:
<223> OTHER INFORMATION: 16C11 heavy chain variable region

<400> SEQUENCE: 67

Glu Val Gln Leu Gln Gln Ser Gly Pro Glu Leu Gly Lys Pro Gly Ala
1               5                   10                  15

Ser Val Lys Ile Ser Cys Lys Ala Ser Gly Tyr Ser Phe Thr Gly Tyr
                20                  25                  30

Asn Met Tyr Trp Val Lys Gln Ser His Arg Lys Ser Leu Glu Trp Ile
            35                  40                  45

Gly Tyr Ile Asp Pro Tyr Asn Gly Asp Thr Ser Tyr Asn Gln Lys Ser
    50                  55                  60

Lys Gly Lys Ala Thr Leu Thr Ala Asp Arg Ser Ser Thr Ala Tyr
65                  70                  75                  80

Met His Leu Asn Ser Leu Thr Ser Glu Asp Ser Gly Ile Tyr Tyr Cys
                85                  90                  95

Ala Arg Gly Ala Tyr Gly Ser Ser Tyr Ala Tyr Trp Gly Gln Gly Thr
            100                 105                 110

Leu Val Ala Val Ser Ala
            115